US008933021B2

(12) United States Patent
Hubalek et al.

(10) Patent No.: US 8,933,021 B2
(45) Date of Patent: Jan. 13, 2015

(54) INSULIN DERIVATIVE

(75) Inventors: Frantisek Hubalek, Copenhagen (DK); Thomas Hoeg-Jensen, Klampenborg (DK); Ib Jonassen, Valby (DK); Patrick William Garibay, Holte (DK); Palle Jakobsen, Vaerløse (DK); Svend Havelund, Bagsvaerd (DK); Janos Tibor Kodra, Cophenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 990 days.

(21) Appl. No.: 12/297,911

(22) PCT Filed: May 8, 2007

(86) PCT No.: PCT/EP2007/054444
§ 371 (c)(1),
(2), (4) Date: Dec. 15, 2008

(87) PCT Pub. No.: WO2007/128817
PCT Pub. Date: Nov. 15, 2007

(65) Prior Publication Data
US 2009/0239785 A1   Sep. 24, 2009

Related U.S. Application Data

(60) Provisional application No. 60/801,122, filed on May 17, 2006, provisional application No. 60/835,354, filed on Aug. 3, 2006.

(30) Foreign Application Priority Data

May 9, 2006 (EP) ..................................... 06113709
Aug. 1, 2006 (EP) ..................................... 06118260

(51) Int. Cl.
*C07K 14/62*   (2006.01)
*A61K 38/00*   (2006.01)

(52) U.S. Cl.
CPC *C07K 14/62* (2013.01); *A61K 38/00* (2013.01)
USPC ........................................................ 514/5.9

(58) Field of Classification Search
None
See application file for complete search history.

(56) References Cited

U.S. PATENT DOCUMENTS

| | | | |
|---|---|---|---|
| 3,528,960 A | 9/1970 | Haas | |
| 5,359,030 A | 10/1994 | Ekwuribe | |
| 5,750,497 A | 5/1998 | Havelund et al. | |
| 5,898,067 A | 4/1999 | Balschmidt et al. | |
| 5,905,140 A | 5/1999 | Hansen | |
| 5,922,675 A | 7/1999 | Baker et al. | |
| 6,011,007 A | 1/2000 | Havelund et al. | |
| 6,174,856 B1 | 1/2001 | Langballe et al. | |
| 6,335,316 B1* | 1/2002 | Hughes et al. ................. 514/6.3 |
| 6,869,930 B1 | 3/2005 | Havelund et al. | |
| 7,615,532 B2 | 11/2009 | Jonassen et al. | |
| 8,003,605 B2 | 8/2011 | Bayer et al. | |
| 8,067,362 B2 | 11/2011 | Kodra et al. | |
| 8,710,000 B2 | 4/2014 | Garibay et al. | |
| 2004/0138099 A1 | 7/2004 | Draeger | |
| 2004/0254119 A1 | 12/2004 | West et al. | |
| 2008/0171695 A1 | 7/2008 | Garibay et al. | |
| 2010/0167990 A1 | 7/2010 | Poulsen et al. | |
| 2010/0227796 A1 | 9/2010 | Garibay et al. | |
| 2013/0143803 A1 | 6/2013 | Andresen et al. | |

FOREIGN PATENT DOCUMENTS

| | | |
|---|---|---|
| EP | 0712861 | 5/1996 |
| JP | 01254699 | 10/1989 |
| JP | H3-204823 | 9/1991 |
| JP | H6-506444 | 7/1994 |
| JP | H09502867 A | 3/1997 |
| JP | 2008-528658 | 7/2008 |
| JP | 2008-528659 | 7/2008 |
| JP | 2009-522231 | 6/2009 |
| JP | 2009-528325 | 8/2009 |
| JP | 2009-530242 | 8/2009 |
| WO | WO 95/07931 | 3/1995 |
| WO | WO 96/29344 | 9/1996 |
| WO | WO 97/31022 | 8/1997 |
| WO | WO 98/02460 | 1/1998 |
| WO | 9922754 A1 | 5/1999 |
| WO | WO 03/013573 | 2/2003 |
| WO | WO 2005/005477 | 1/2005 |
| WO | WO 2005/012346 | 2/2005 |
| WO | WO 2005/012347 | 2/2005 |
| WO | 2005/047508 A1 | 5/2005 |
| WO | 2005/047509 A2 | 5/2005 |
| WO | 2006/008238 A1 | 1/2006 |
| WO | 2006/008239 A2 | 1/2006 |
| WO | WO 2006/082204 | 8/2006 |
| WO | WO 2006/082205 | 8/2006 |
| WO | 2007/074134 A1 | 7/2007 |
| WO | WO 2007/074133 | 7/2007 |
| WO | WO 2007/096431 | 8/2007 |
| WO | WO 2007/104737 | 9/2007 |
| WO | WO 2007/128815 | 11/2007 |
| WO | 2008/152106 A1 | 12/2008 |
| WO | 2009/060071 A1 | 5/2009 |
| WO | 2009/060072 A1 | 5/2009 |
| WO | 2010/049488 A1 | 5/2010 |
| WO | 2011/141407 A1 | 11/2011 |
| WO | 2011/141408 A2 | 11/2011 |

* cited by examiner

*Primary Examiner* — Christina Bradley
(74) *Attorney, Agent, or Firm* — Rosemarie R. Wilk-Orescan

(57) ABSTRACT

The present invention relates to novel human insulin derivatives which are soluble at physiological pH values and have a prolonged profile of action. The invention also relates to methods of providing such derivatives, to pharmaceutical compositions containing them, to methods of treating diabetes and hyperglycaemia using the insulin derivatives of the invention and to the use of such insulin derivatives in the treatment of diabetes and hyperglycaemia.

14 Claims, 4 Drawing Sheets

SEC analysis of a mixture of the insulin derivative of example 2 with insulin aspart in ratio 70/30 with 2.1 Zn(II) per 6 insulin derivatives
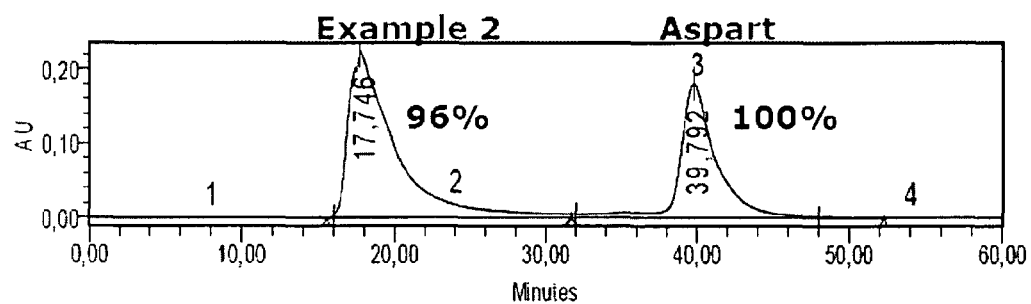
SEC analysis of a mixture of the insulin derivative of example 2 with insulin aspart in ratio 70/30 with 6 Zn(II) per 6 insulin derivatives
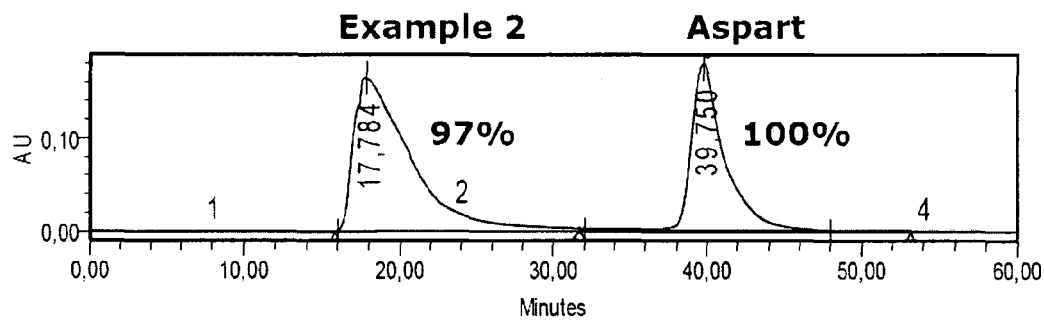
Fig. 1

Action profile of the insulin derivative of example 2 in different concentrations and Zn-formulations.

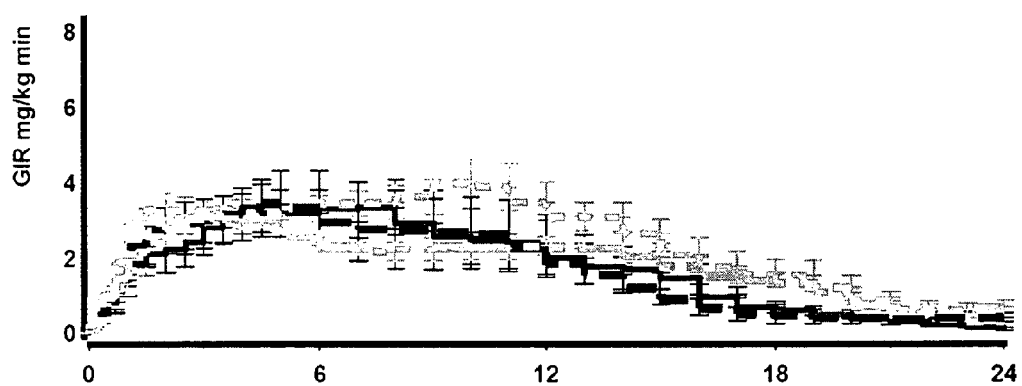

— Insulin derivative of example 2: 216nmol, 360µl, 600µM, 2.3 Zn/6 insulin derivatives. N=6

Insulin derivative of example 2: 216nmol, 360µl, 600µM, 6 Zn/6 insulin derivatives N=5

■ ■ Insulin derivative of example 2: 216nmol, 180µl, 1200µM, 2.3 Zn/6 insulin derivatives. N=6

⋯ ⋯ Insulin derivative of example 2: 216nmol, 180µl, 1200µM, 6 Zn/6 insulin derivatives, n=5

Fig. 2

Clamp after subcutaneous injection in pigs of example 2 in three different doses.

▬▬▬ Dose 648nmol, concentration 1200μM, insulin derivative of example 2 with 3 Zn/ 6 insulin derivatives ▪▪▪▪ Dose 432nmol, concentration 1200μM, insulin derivative of example 2 with 3 Zn/ 6 insulin derivatives ▬ ▬ Dose 216nmol, concentration 1200μM, 3 Zn/ 6 insulin derivatives

INSULIN DERIVATIVE

CROSS-REFERENCE TO RELATED APPLICATIONS

This application is a 35 U.S.C. §371 national stage application of International Patent Application PCT/EP2007/054444 (published as WO 2007/128817 A2), filed May 8, 2007, which claimed priority of European Patent Application 06113709.7, filed May 9, 2006 and European Patent Application 06118260.6, filed Aug. 1, 2006; this application further claims priority under 35 U.S.C. §119 of U.S. Provisional Application 60/801,122, filed May 16, 2006 and U.S. Provisional Application 60/835,354, filed Aug. 3, 2006.

FIELD OF THE INVENTION

The present invention relates to novel human insulin derivatives which are soluble at physiological pH values and have a prolonged profile of action. The invention also relates to methods of providing such derivatives, to pharmaceutical compositions containing them, to methods of treating diabetes and hyperglycaemia using the insulin derivatives of the invention and to the use of such insulin derivatives in the treatment of diabetes and hyperglycaemia.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies. Also, evidence has been found that the protamine-insulin complex is itself immunogenic. Therefore, with some patients the use of long acting insulin compositions containing protamines must be avoided.

Another type of long acting insulin compositions are solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

International patent application published under number WO 2005/012347 (Novo Nordisk A/S) concerns insulin derivatives which have a sidechain attached to either the α-amino group of the N-terminal amino acid residue of the B-chain or the ε-amino group of a Lys residue present in the B chain.

International patent application No. EP2006/050593 (Novo Nordisk A/S) discloses insulin derivatives having an aromatic group in the side chain.

Patent application no. EP2006/050594 (Novo Nordisk A/S), disclose insulin derivatives having a PEG in the side chain.

Other insulin derivatives are disclosed in JP laid-open patent application No. 1-254699 (Kodama Co., Ltd.) and WO 95/07931 (Novo Nordisk A/S).

However, there is still a need for insulin having a more prolonged profile of action than the insulin derivatives known up till now.

SUMMARY OF THE INVENTION

In one aspect of the invention an insulin derivative is having a formula

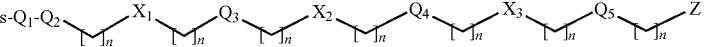

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—$Z$ is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$ is:
  an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
  a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or
  a bond $Q_2$ is:
  —COCH(CONH$_2$)—
  —COCH$_2$N(CH$_2$CONH$_2$)—
  —COCH$_2$N(CH$_2$CONH$_2$)COCH$_2$N(CH$_2$CONH$_2$)

—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—;
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or
a bond
provided that
at least one of Q$_1$ or Q$_2$ is not a bond, and
that Q$_2$ is not —CO—(CH$_2$)$_2$—CO—NH— when n is 0 or 1, X$_1$ is a bond and Q$_3$ is (CH$_2$CH$_2$O)$_2$—, (CH$_2$CH$_2$O)$_3$— or (CH$_2$CH$_2$OCH$_2$CH$_2$CH$_2$O)— and
that if an amine in Q$_1$ or Q$_2$ forms a bond with the rest of the substituent, the amine must be bound to the rest of the substituent via a carbonyl group;
Q$_3$, Q$_4$, and Q$_5$ independently of each other can be
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 4 to 32;
—CO—((CR$^5$R$^6$)$_{1-6}$—NH—CO)—;
—(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;
—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$ independently of each other can be H, —CH$_3$ or —(CH)$_{1-6}$—CH$_3$;
(CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—; —(CH$_2$OCH$_2$)$_y$— where y is 1-20;
arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$;
a chain of the formula —(CH$_2$)$_s$—Y$_1$—(Ar)$_{v1}$—Y$_2$—(CH$_2$)$_w$—Y$_3$—(Ar)$_{v2}$—Y$_4$—(CH$_2$)$_t$—Y$_5$—(Ar)$_{v3}$—Y$_6$—(CH$_2$)$_z$— wherein Ar is defined as above, Y$_1$-Y$_6$ independently of each other can be O, S, S═O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other and that the structure —O—(CH$_2$)$_1$—O— does not occur; or
a bond;
with the proviso that at least one of Q$_3$-Q$_5$ is not a bond;
X$_1$, X$_2$ and X$_3$ are independently of each other
O;
—C═O
a bond;
NCOR$^1$, where R$^1$ can be H, —CH$_3$ or —(CH)$_{1-6}$—CH$_3$; or

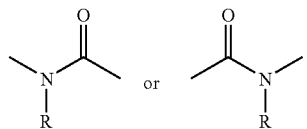

where R is hydrogen, C$_{1-3}$-alkyl, C$_{2-3}$-alkenyl or C$_{2-3}$-alkynyl;
with the proviso that X$_1$, X$_2$ and X$_3$ cannot bind to Z and when X$_1$, X$_2$ and X$_3$ are O, then X$_1$, X$_2$ and X$_3$ do not bind directly to O in Q$_3$, Q$_4$, and Q$_5$
and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—OSO$_3$H
—OPO3H$_2$
—PO$_3$H$_2$ or
-tetrazol-5-yl or
—O—W$_1$,
where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$ where R$^3$ and R$^4$, independently of each other can be H, —(CH$_2$)$_{1-6}$—SO$_3$H, or —(CH$_2$)$_{1-6}$—O—PO$_3$H$_2$; provided that when Z is —O—W$_1$ then Q$_1$ must be present
and any Zn$^{2+}$ complex thereof
In one aspect of the invention Q$_2$ of the insulin derivative is selected from the group consisting of
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—;
—CO—((CR$^5$R$^6$)$_{1-6}$—NH—CO)$_{1-4}$—; or
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$
In one aspect of the invention Q$_3$ is —(CH$_2$)$_m$— where m is an integer in the range of 6 to 32 or from 8 to 20 or m is 12, 13, 14, 15 or 16.
In one aspect of the invention Q$_1$, Q$_4$, Q$_5$, X$_1$, X$_2$ and X$_3$ is bonds and n is zero.
In one aspect of the invention Q$_3$ is —(CH$_2$)$_m$— where m is an integer in the range of 6 to 32 or from 8 to 20 or m is 12, 13, 14, 15 or 16, Q$_1$, Q$_4$, Q$_5$, X$_1$, X$_2$ and X$_3$ is bonds, n is zero and Z is —COOH.
In one aspect of the invention one of Q$_3$, Q$_4$, or Q$_5$ is (CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—; —(CH$_2$OCH$_2$)$_y$— where y is 1-20.
In one aspect of the invention Q$_3$ is
—CO—((CR$^5$R$^6$)$_{1-6}$—NH—CO)—;

—(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;

—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$ independently of each other can be H, —CH$_3$ or —(CH)$_{1-6}$—CH$_3$; or a bond Q$_4$ is —(CH$_2$)$_m$— where m is an integer from 4 to 22;

a divalent hydrocarbon chain comprising 1, 2 or 3 —CH=CH— groups and a number of —CH$_2$— groups sufficient to give a total number of carbon atoms in the chain in the range of 4 to 22;

arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$; or a chain of the formula

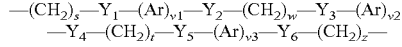

wherein Ar is defined as above, Y$_1$-Y$_6$ independently of each other can be O, S, S=O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other and that the structure —O—(CH$_2$)$_1$—O— does not occur;

X$_1$ is

O;

—C=O

NCOR$^1$, where R$^1$ can be H, —CH$_3$ or —(CH)$_{1-6}$—CH$_3$; or

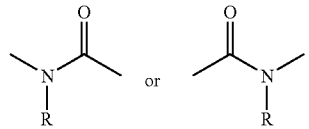

where R is hydrogen, C$_{1-3}$-alkyl, C$_{2-3}$-alkenyl or C$_{2-3}$-alkynyl;

with the proviso that when X$_1$ is O then X$_1$ does not bind directly to O in Q$_4$;

X$_2$, X$_3$ and Q$_5$ are bonds;

All values of n are zero; and

Z is:

—COOH;

—CO-Asp;

—CO-Glu;

—CO-Gly;

—CO-Sar;

—CH(COOH)$_2$;

—N(CH$_2$COOH)$_2$;

—SO$_3$H

—OSO$_3$H

—OPO$_3$H$_2$

—PO$_3$H$_2$ or

-tetrazol-5-yl or

—O—W$_1$, where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$ where R$^3$ and R$^4$ independently of each other can be H, —(CH$_2$)$_{1-6}$—SO$_3$H, or —(CH$_2$)$_{1-6}$—O—PO$_3$H$_2$; and any Zn$^{2+}$ complex thereof.

In one aspect of the invention Z is —COOH.

In one aspect of the invention the parent insulin of the insulin derivative is an insulin analogue.

In one aspect of the invention the parent insulin is selected from the group consisting of: desB30 human insulin, GlyA21 human insulin, GlyA21desB30 human insulin, GlyA21ArgB31ArgB32 human insulin, LysB3GluB29 human insulin, LysB28ProB29 human insulin and ThrB29LysB30 human insulin.

In one aspect of the invention there is provided a pharmaceutical composition for the treatment of diabetes in a patient in need of such treatment, comprising a therapeutically effective amount of an insulin derivative according to the invention.

In one aspect of the invention there is provided a method for producing a pharmaceutical composition comprising a therapeutically effective amount of an insulin derivative according to the invention, wherein up to about 10 zinc atoms per 6 molecules of insulin derivative are added to the pharmaceutical composition.

In one aspect of the invention there is provided a method of treating diabetes in a patient in need of such a treatment, comprising administering to the patient a therapeutically effective amount of an insulin derivative according to the invention.

In one aspect of the invention the insulin derivative is administered pulmonary.

In one aspect of the invention there is provided a mixture of an insulin derivative according to the invention and a rapid acting insulin analogue selected from the group consisting of AspB28 human insulin; LysB28ProB29 human insulin and LysB3GluB29 human insulin.

In one aspect of the invention the insulin derivative is selected from the group consisting of:

N$^{\epsilon B29}$-ω-carboxy-pentadecanoyl-γ-L-glutamylamide desB30 human insulin, N$^{\epsilon B29}$-ω-carboxy-pentadecanoyl-γ-amino-butanoyl desB30 human insulin, N$^{\epsilon B29}$-ω-carboxy-tetradecanoyl-γ-L-glutamylamide desB30 human insulin, N$^{\epsilon B29}$-ω-carboxy-tridecanoyl-γ-L-glutamylamide desB30 human insulin, N$^{\epsilon B29}$-ω-carboxy-pentadecanoyl-β-alanyl desB30 human insulin, N$^{\epsilon B29}$-ω-carboxy-pentadecanoyl-γ-L-aspartylamide desB30 human insulin, N$^{\epsilon B29}$-ω-carboxy-pentadecanoyl-ε-aminohexanoyl desB30 human insulin, N$^{\epsilon B29}$-ω-carboxy-pentadecanoyl-δ-aminopentanoyl desB30 human insulin, N$^{\epsilon B29}$-10-(4-carboxyphenoxy)-decanoyl-γ-L-glutamylamide desB30 human insulin, N$^{\epsilon B29}$-4-[11-(4-Carboxyphenyl)undecanoylamino]butyryl desB30 human insulin, N$^{\epsilon B29}$-(3-(3-{4-[3-(7-carboxyheptanoylamino)propoxy]butoxy}propylcarbamoyl)-propionyl-γ-glutamylamide) desB30 human Insulin, N$^{\epsilon B29}$-ω-carboxy-tridecanoyl-γ-amino-butanoyl desB30 human insulin, N$^{\epsilon B29}$-ω-carboxy-undecanoyl-γ-amino-butanoyl desB30 human insulin, $N^{\epsilon B29}$-ω-carboxy-tetradecanoyl-γ-amino-butanoyl desB30 human insulin,
$N^{\epsilon B29}$-{4-[10-(4-Carboxy-phenoxy)-decanoylamino]-butyryl}desB30 insulin,
$N^{\epsilon B29}$-{4-[(14-Carboxy-tetradecanoylamino)-methyl]-benzoyl}desB30 insulin,
$N^{\epsilon B29}$-[16-(4-Carboxy-phenoxy)-hexadecanoyl]desB30 insulin,
$N^{\epsilon B29}$-{4-[(15-carboxypentadecanoylamino)benzoyl]-desB30 human insulin and
$N^{\epsilon B29}$-{4-[(15-Carboxy-pentadecanoylamino)-methyl]-benzoyl}-desB30 insulin

DEFINITIONS

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues.

In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

With "desB30 insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin, porcine insulin or bovine insulin with disulfide bridges between CysA7 and CysB7 and between CysA20 and CysB19 and an internal disulfide bridge between CysA6 and CysA11.

By "parent insulin" is meant a naturally occurring insulin such as human insulin or porcine insulin. Alternatively, the parent insulin can be an insulin analogue.

The expression "uncharged" means that no group or groups that would assume a charge at pH interval 4 to 9 are present. For example no free carboxylic acids are present.

With "fatty difunctionalized moiety" is meant a carbon chain of 6 to 32 carbon atoms comprising two functional groups selected from carboxy, amino or hydroxyl.

The term "non-linking amide" is meant to describe an amide function present in a side chain or side group of a residue present in the substituent, such that said amide bond is not used to connect the residues of the substituent together. It should be understood that a residue of the substituent in addition to the non-linking amide can comprise further amide groups, eg. amides that bind to other residues of the substituent.

"Amino acid amide residue" means the alpha-carboxy amide of an amino acid, or if the amino acid contains a carboxylic acid in the side-chain, "amino acid amide" means amide of either the alpha-carboxy group, or amide of the side-chain carboxy group, as specified.

When an insulin derivative according to the invention is stated to be "soluble at physiological pH values" it means that the insulin derivative can be used for preparing insulin compositions that are fully dissolved at physiological pH values. Such favourable solubility may either be due to the inherent properties of the insulin derivative alone or a result of a favourable interaction between the insulin derivative and one or more ingredients contained in the vehicle.

The term "no blunting" as used herein means that when formulated in one formulation both the rapid acting insulin and the acylated insulin has profile of action which is identical or substantially identical with the profile of action, when administering the rapid acting insulin and the acylated insulin in separate formulations.

The expression "high molecular weight insulin" or "hmw" means that the molecular weight of a complex of human insulin, of an insulin analogue or of an insulin derivative is above human serum albumin, above a dodecameric complex of an insulin analogue or of an insulin derivative or more than about 72 kDalton.

The expression "medium molecular weight insulin" or "mmw" means that the molecular weight of a complex of human insulin, of an insulin analogue or of an insulin derivative is from about an insulin hexamer to about an insulin dodecamer between 24 and 80 kDalton.

The expression "low molecular weight insulin" or "lmw" means that the molecular weight of a human insulin, an insulin analogue or an insulin derivative is below 24 kDalton.

The following abbreviations have been used in the specification and examples:
Cv column volume
HPLC High Performance Liquid Chromatography
HSA human serum albumin
LC liquid chromatography
MALDI Matrix Assisted Laser Desorption Ionization
MS mass spectrometry
RT room temperature
SEC size exclusion chromatography
SPA Scitillation Proximity Assay
Tris tris(hydroxymethyl)aminomethane
O.D. optical density=absorbance
X2 monomer AspB9 GluB27 human insulin
DIEA: N,N-diisopropylethylamine
DMF: N,N-dimethylformamide
Sar: Sarcosine (N-methyl-glycine)
tBu: tert-butyl
TSTU: O—(N-succinimidyl)-1,1,3,3-tetramethyluronium tetrafluoroborate
THF: Tetrahydrofuran
EtOAc: Ethyl acetate
DIPEA: Diisopropylethylamine TEA: triethyl amine
TFA: trifluoracetic acid
DCM: dichloromethane
RT: room temperature
PEG: polyethyleneglycol
GIR: Glucose infusion rate All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

DESCRIPTION OF THE INVENTION

The present invention is based on the recognition that having a substituent in an insulin derivative molecule where only the terminal group is charged, plays an important role for the in vivo duration of action of prolonged-acting insulins, and for the mixability of prolonged-acting insulin with fast-acting insulin with no blunting.

Advantageously, insulin derivatives according to the invention are soluble at physiological pH values, have a potency which is comparable to that of human insulin, and are mixable with fast-acting insulins with no blunting. The individual profiles of action of mixed basal and bolus insulins are retained in formulations containing Zn(II) concentrations of up to or less than approximately 3 Zn(II) per insulin hexamer which limits the risk of precipitations in the formulation, compared to formulations containing more than 3 Zn (II) per insulin hexamer.

The invention is summarized in the following paragraphs:
An insulin derivative having a formula

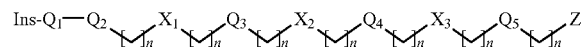

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$ is:
  an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or a bond $Q_2$ is:
  —COCH(CONH$_2$)—
  —COCH$_2$N(CH$_2$CONH$_2$)—
  —COCH$_2$N(CH$_2$CONH$_2$)COCH$_2$N(CH$_2$CONH$_2$)
  —COCH$_2$CH$_2$N(CH$_2$CH$_2$CONH$_2$)—
  —COCH$_2$CH$_2$N(CH$_2$CH$_2$CONH$_2$)—COCH$_2$CH$_2$N(CH$_2$CH$_2$CONH$_2$)—
  —COCH$_2$N(CH$_2$CH$_2$CONH$_2$)—
  —COCH$_2$CH$_2$N(CH$_2$CONH$_2$)—
  —COCH$_2$OCH$_2$CONH—
  —CO—((CR$^5$R$^6$)$_{1-6}$—NH—CO)$_{1-4}$—;
  —CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or
  a bond
  provided that
    at least one of $Q_1$ or $Q_2$ is not a bond, and
    that $Q_2$ is not —CO—(CH$_2$)$_2$—CO—NH— when n is 0 or 1, $X_1$ is a bond and $Q_3$ is (CH$_2$CH$_2$O)$_2$—, (CH$_2$CH$_2$O)$_3$— or (CH$_2$CH$_2$OCH$_2$CH$_2$CH$_2$CH$_2$O)— and
    that if an amine in $Q_1$ or $Q_2$ forms a bond with the rest of the substituent, the amine must be bound to the rest of the substituent via a carbonyl group;

$Q_3$, $Q_4$, and $Q_5$ independently of each other can be
  —(CH$_2$)$_m$— where m is an integer in the range of 6 to 32;
  a divalent hydrocarbon chain comprising 1, 2 or 3 —CH═CH— groups and a number of —CH$_2$— groups sufficient to give a total number of carbon atoms in the chain in the range of 4 to 32;
  —CO—((CR$^5$R$^6$)$_{1-6}$—NH—CO)—;
  —(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;
  —CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$;
  (CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$O)$_y$—;
  —(CH$_2$OCH$_2$)$_y$— where y is 1-20;
  arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$; or
  a chain of the formula

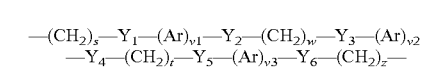

wherein Ar is defined as above, $Y_1$-$Y_6$ independently of each other can be O, S, S═O, SO$_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—(CH$_2$)$_1$—O— does not occur; or a bond;
with the proviso that at least one of $Q_3$-$Q_5$ is not a bond;
$X_1$, $X_2$ and $X_3$ are independently of each other
  O;
  —C═O
  a bond;
  NCOR$^1$, where R$^1$ can be H, —CH$_3$ or —(CH)$_{1-6}$—CH$_3$; or

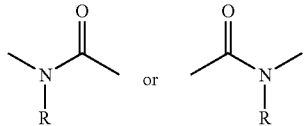

where R is hydrogen, C$_{1-3}$-alkyl, C$_{2-3}$-alkenyl or C$_{2-3}$-alkynyl;
  with the proviso that
    —$X_1$, $X_2$ and $X_3$ cannot bind to Z and
    when $X_1$, $X_2$ and $X_3$ are O then $X_1$, $X_2$ and $X_3$ do not bind directly to O in $Q_3$, $Q_4$, and $Q_5$
and
Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H
  —OSO$_3$H
  —OPO3H$_2$
  —PO$_3$H$_2$ or
  -tetrazol-5-yl or
  —O—W$_1$,
where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$ where R$^3$ and R$^4$ independently of each other can be H, —(CH$_2$)$_{1-6}$—SO$_3$H, or —(CH$_2$)$_{1-6}$—O—PO$_3$H$_2$; provided that when Z is —O—W$_1$ then $Q_1$ must be present;
and any Zn$^{2+}$ complex thereof.

2. An insulin derivative having a formula

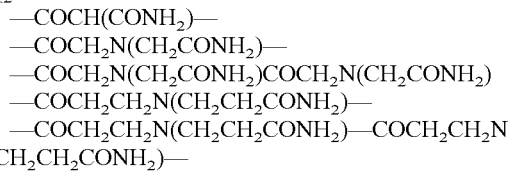

wherein Ins is a parent insulin moiety and $Q_1$-$Q_2$-[CH$_2$]$_n$-$X_1$-[CH$_2$]$_n$-$Q_3$-[CH$_2$]$_n$-$X_2$-[CH$_2$]$_n$-$Q_4$-[CH$_2$]$_n$-$X_3$-[CH$_2$]$_n$-$Q_5$-[CH$_2$]$_n$-Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;
each n is independently 0, 1, 2, 3, 4, 5 or 6;
$Q_1$ is:
  an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
  a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or
  a bond
$Q_2$ is:
  —COCH(CONH$_2$)—
  —COCH$_2$N(CH$_2$CONH$_2$)—
  —COCH$_2$N(CH$_2$CONH$_2$)COCH$_2$N(CH$_2$CONH$_2$)—
  —COCH$_2$CH$_2$N(CH$_2$CH$_2$CONH$_2$)—
  —COCH$_2$CH$_2$N(CH$_2$CH$_2$CONH$_2$)—COCH$_2$CH$_2$N(CH$_2$CH$_2$CONH$_2$)—
  —COCH$_2$N(CH$_2$CH$_2$CONH$_2$)—
  —COCH$_2$CH$_2$N(CH$_2$CONH$_2$)—
  —COCH$_2$OCH$_2$CONH—
  —CO—((CR$^5$R$^6$)$_{1-6}$—NH—CO)$_{1-4}$—;
  —CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or
  a bond
  provided that
    at least one of $Q_1$ or $Q_2$ is not a bond, and
    that $Q_2$ is not —CO—(CH$_2$)$_2$—CO—NH— when n is 0 or 1, $X_1$ is a bond and $Q_3$ is (CH$_2$CH$_2$O)$_2$—, (CH$_2$CH$_2$O)$_3$— or (CH$_2$CH$_2$OCH$_2$CH$_2$CH$_2$CH$_2$O)— and
    that if an amine in $Q_1$ or $Q_2$ forms a bond with the rest of the substituent, the amine must be bound to the rest of the substituent via a carbonyl group;
$Q_3$, $Q_4$, and $Q_5$ independently of each other can be
  —(CH$_2$)$_m$— where m is an integer in the range of 6 to 32;
  a divalent hydrocarbon chain comprising 1, 2 or 3 —CH═CH— groups and a number of —CH$_2$— groups sufficient to give a total number of carbon atoms in the chain in the range of 4 to 32;
  —CO—((CR$^5$R$^6$)$_{1-6}$—NH—CO)—;
  —(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;
  —CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$ independently of each other can be H, —CH$_3$ or —(CH)$_{1-6}$—CH$_3$;
  (CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$O)$_y$—; —(CH$_2$OCH$_2$)$_y$— where y is 1-20;
  arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$; or
  a chain of the formula
  —(CH$_2$)$_s$—Y$_1$—(Ar)$_{v1}$—Y$_2$—(CH$_2$)$_w$—Y$_3$—(Ar)$_{v2}$—Y$_4$—(CH$_2$)$_t$—Y$_5$—(Ar)$_{v3}$—Y$_6$—(CH$_2$)$_z$—
  wherein Ar is defined as above, Y$_1$-Y$_6$ independently of each other can be O, S, S═O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that $Y_1$-$Y_6$ do not link to each other and that the structure —O—$(CH_2)_1$—O— does not occur; or
a bond;
with the proviso that
at least one of $Q_3$-$Q_5$ is not a bond and
$Q_2$ is not —CO—$((CH_2)_{1-6}$—NH—CO$)_{1-4}$— when one of $Q_3$-$Q_5$ is arylene or heteroarylene or a chain of the formula —$(CH_2)_s$—$Y_1$—$(C_6H_4)_{v1}$—$Y_2$—$(CH_2)_w$—$Y_3$—$(C_6H_4)_{v2}$—$Y_4$—$(CH_2)_t$—$Y_5$—$(C_6H_4)_{v3}$—$Y_6$—$(CH_2)_z$—;
$X_1$, $X_2$ and $X_3$ are independently of each other
O;
—C=O
a bond;
NCOR$^1$, where R$^1$ can be H, —CH$_3$ or —(CH)$_{1-6}$—CH$_3$; or

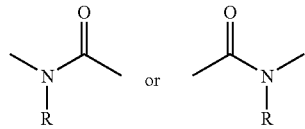

where R is hydrogen, $C_{1-3}$-alkyl, $C_{2-3}$-alkenyl or $C_{2-3}$-alkynyl;
with the proviso that
—$X_1$, $X_2$ and $X_3$ cannot bind to Z and
when $X_1$, $X_2$ and $X_3$ are O then $X_1$, $X_2$ and $X_3$ do not bind directly to O in $Q_3$, $Q_4$, and $Q_5$
and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—OSO$_3$H
—OPO3H$_2$
—PO$_3$H$_2$ or
-tetrazol-5-yl or
—O—W$_1$,
where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$ where R$^3$ and R$^4$, independently of each other can be H, —(CH$_2$)$_{1-6}$—SO$_3$H, or —(CH$_2$)$_{1-6}$—O—PO$_3$H$_2$; provided that when Z is —O—W$_1$ then Q$_1$ must be present;
and any Zn$^{2+}$ complex thereof.
3. An insulin derivative having a formula

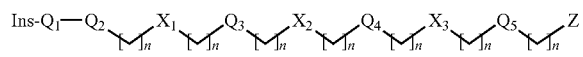

wherein Ins is a parent insulin moiety and Q$_1$-Q$_2$-[CH$_2$]$_n$—X$_1$—[CH$_2$]$_n$-Q$_3$-[CH$_2$]$_n$—X$_2$—[CH$_2$]$_n$-Q$_4$-[CH$_2$]$_n$—X$_3$—[CH$_2$]$_n$-Q$_5$-[CH$_2$]$_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in Q$_1$ or Q$_2$ of the substituent;

each n is independently 0, 1, 2, 3, 4, 5 or 6;
Q$_1$ is:
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or
a bond
Q$_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)—
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—;
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or
a bond
provided that
at least one of Q$_1$ or Q$_2$ is not a bond, and
that Q$_2$ is not —CO—(CH$_2$)$_2$—CO—NH— when n is 0 or 1, X$_1$ is a bond and Q$_3$ is (CH$_2$CH$_2$O)$_2$—, (CH$_2$CH$_2$O)$_3$— or (CH$_2$CH$_2$OCH$_2$CH$_2$CH$_2$O)— and
that if an amine in Q$_1$ or Q$_2$ forms a bond with the rest of the substituent, the amine must be bound to the rest of the substituent via a carbonyl group;
Q$_3$, Q$_4$, and Q$_5$ independently of each other can be
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 4 to 32;
—CO—((CR$^5$R$^6$)$_{1-6}$—NH—CO)—;
—(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;
—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$;
(CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—; —(CH$_2$OCH$_2$)$_y$— where y is 1-20;
arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$, where R$^1$ and R$^2$, independently of each other can be H, —CH$_3$ or —(CH)$_{1-6}$—CH$_3$; or a chain of the formula

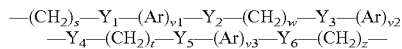

wherein Ar is defined as above, $Y_1$-$Y_6$ independently of each other can be O, S, S=O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur; or
a bond;
with the proviso that
at least one of $Q_3$-$Q_5$ is not a bond and
that $Q_1$ or $Q_2$ comprises a non-linking amide when one of $Q_3$-$Q_5$ is arylene, heteroarylene or a chain of the formula —$(CH_2)_s$—$Y_1$—$(C_6H_4)_{v1}$—$Y_2$—$(CH_2)_w$—$Y_3$—$(C_6H_4)_{v2}$—$Y_4$—$(CH_2)_t$—$Y_5$—$(C_6H_4)_{v3}$—$Y_6$—$(CH_2)_z$—.
$X_1$, $X_2$ and $X_3$ are independently of each other
O;
—C=O
a bond;
$NCOR^1$, where $R^1$ can be H, —$CH_3$ or —$(CH)_{1-6}$—$CH_3$; or

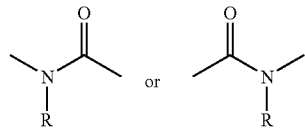

where R is hydrogen, $C_{1-3}$-alkyl, $C_{2-3}$-alkenyl or $C_{2-3}$-alkynyl;
with the proviso that
$X_1$, $X_2$ and $X_3$ cannot bind to Z and
when $X_1$, $X_2$ and $X_3$ are O then $X_1$, $X_2$ and $X_3$ do not bind directly to O in $Q_3$, $Q_4$, and $Q_5$
and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—OSO$_3$H
—OPO3H$_2$
—PO$_3$H$_2$ or
-tetrazol-5-yl or
—O—$W_1$,
where $W_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$ where $R^3$ and $R^4$ independently of each other can be H, —(CH$_2$)$_{1-6}$—SO$_3$H, or —(CH$_2$)$_{1-6}$—O—PO$_3$H$_2$; provided that when Z is —O—$W_1$ then $Q_1$ must be present
and any $Zn^{2+}$ complex thereof.

4. An insulin derivative having a formula

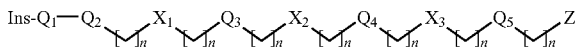

wherein Ins is a parent insulin moiety and $Q_1$-$Q_2$-[CH$_2$]$_n$—$X_1$—[CH$_2$]$_n$-$Q_3$-[CH$_2$]$_n$—$X_2$—[CH$_2$]$_n$-$Q_4$-[CH$_2$]$_n$—$X_3$—[CH$_2$]$_n$-$Q_5$-[CH$_2$]$_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;
each n is independently 0, 1, 2, 3, 4, 5 or 6;
$Q_1$ is:
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or
a bond
$Q_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—CO—NH)$_{1-4}$—, where $R^5$ independently can be H, —CH$_3$, —(CH$_2$)$_{1-6}$CH$_3$ or —CONH$_2$ and $R^6$ independently can be H, —CH$_3$, —(CH$_2$)$_{1-6}$CH$_3$; or
a bond
provided that
at least one of $Q_1$ or $Q_2$ is not a bond, and
that $Q_2$ is not —CO—(CH$_2$)$_2$—CO—NH— when n is 0 or 1, $X_1$ is a bond and $Q_3$ is (CH$_2$CH$_2$O)$_2$—, (CH$_2$CH$_2$O)$_3$— or (CH$_2$CH$_2$OCH$_2$CH$_2$CH$_2$CH$_2$O)— and
that if an amine in $Q_1$ or $Q_2$ forms a bond with the rest of the substituent, the amine must be bound to the rest of the substituent via a carbonyl group;
$Q_3$, $Q_4$, and $Q_5$ independently of each other can be
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 4 to 32;
—CO—((CR$^5$R$^6$)$_{1-6}$—NH—CO)—;
—(CO—(CR$^5$R$^6$)$_{1-6}$—CO—NH)$_{1-4}$—, where $R^5$ independently can be H, —CH$_3$, —(CH$_2$)$_{1-6}$CH$_3$ or —CONH$_2$ and $R^6$ independently can be H, —CH$_3$, —(CH$_2$)$_{1-6}$CH$_3$;
—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$;
(CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$O)$_y$—; —(CH$_2$OCH$_2$)$_y$— where y is 1-20;

arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$; or a chain of the formula

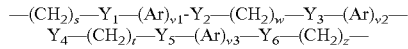

wherein Ar is defined as above, Y$_1$-Y$_6$ independently of each other can be O, S, S=O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other and that the structure —O—(CH$_2$)$_1$—O— does not occur; or a bond;

with the proviso that at least one of Q$_3$-Q$_5$ is not a bond;

X$_1$, X$_2$ and X$_3$ are independently of each other

O;
—C=O
a bond;
NCOR$^1$, where R$^1$ can be H, —CH$_3$ or —(CH)$_{1-6}$—CH$_3$; or

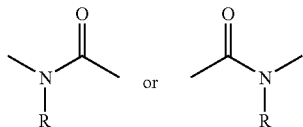

where R is hydrogen, C$_{1-3}$-alkyl, C$_{2-3}$-alkenyl or C$_{2-3}$-alkynyl;

with the proviso that
—X$_1$, X$_2$ and X$_3$ cannot bind to Z and
when X$_1$, X$_2$ and X$_3$ are O then X$_1$, X$_2$ and X$_3$ do not bind directly to O in Q$_3$, Q$_4$, and Q$_5$ and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H
OSO$_3$H
—OPO3H$_2$
—PO$_3$H$_2$ or
-tetrazol-5-yl or
—O—W$_1$,
where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$ where R$^3$ and R$^4$, independently of each other can be H, —(CH$_2$)$_{1-6}$—SO$_3$H, or —(CH$_2$)$_{1-6}$—O—PO$_3$H$_2$; provided that when Z is —O—W$_1$ then Q$_1$ must be present and any Zn$^{2+}$ complex thereof.

5. Insulin derivative according to paragraph 1-4, wherein Q$_1$ is an amino acid amide of an amino acid with a carboxylic acid in the side chain, or an amino acid with an uncharged side chain, the amino acid amide residue or amino acid residue having from 2 to 10 carbon atoms.

6. Insulin derivative according to any of paragraphs 1-5, wherein Q$_1$ is selected from the group consisting of β-D-Asp-amide, β-L-Asp-amide, γ-L-Glu-amide and γ-D-Glu-amide.

7. Insulin derivative according to paragraphs 1-4, wherein Q$_1$ is a chain composed of two, three or four α-amino acid amide residues or amino acid residues with an uncharged side chain.

8. Insulin derivative according to paragraphs 1-4 or 7, wherein Q$_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

9. Insulin derivative according to any of paragraphs 1-8, wherein Q$_2$ is a bond 10. Insulin derivative according to any of paragraphs 1-3 or 5-8, wherein Q$_2$ is —CO—((CR$^5$R$^6$)$_{1-6}$—NH—CO)$_{1-4}$—.

11. Insulin derivative according to paragraph 10, where Q$_2$ is selected from the group consisting of —CO—((CH$_2$)$_2$—NH—CO)$_1$—, —CO—((CH$_2$)$_3$—NH—CO)$_1$— and —CO—((CH$_2$)$_4$—NH—CO)$_1$—, —CO—((CH$_2$)$_5$—NH—CO)$_1$—.

12. Insulin derivative according to paragraphs 1, 3 or 10-11, wherein Q$_1$ is a bond.

13. Insulin derivative according to paragraphs 1-3 wherein Q$_1$ is:

an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid amide or amino acid residues as specified above linked together via amide bonds, in which the chain—via an amide bond—is linked to the α-amino group of the N-terminal amino acid residue of the B chain of Ins or to the ε-amino group of a Lys residue present in the A or B chain of Ins, or a bond Q$_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—;
—(CO—(CR$^5$R$^6$)$_{1-6}$—CO—NH)$_{1-4}$—, where R$^5$ can be H, —CH$_3$, —(CH$_2$)$_{1-6}$CH$_3$ or —CONH$_2$ and R$^6$ can be H, —CH$_3$, —(CH$_2$)$_{1-6}$CH$_3$; or a bond
provided that at least one of $Q_1$ or $Q_2$ is not a bond and that if an amine in $Q_1$ or $Q_2$ forms a bond with the rest of the substituent, the amine must be bound to the rest of the substituent via a carbonyl group;

$Q_3$ is
—$(CH_2)_m$— where m is an integer in the range of 6 to 32;
a divalent hydrocarbon chain comprising 1, 2 or 3 —CH=CH— groups and a number of —$CH_2$— groups sufficient to give a total number of carbon atoms in the chain in the range of 4 to 32; or
a divalent hydrocarbon chain of the formula —$(CH_2)_s$$C_6H_4(CH_2)_w$— wherein v and w are integers or one of them is zero so that the sum of s and w is in the range of 6 to 30;
$X_1$, can be —C=O or a bond;
$Q_4$, $Q_5$, $X_2$ and $X_3$ are bonds;
All values of n are zero; and
Z is:
—COOH;
—CO-Asp;
—CO-Glu;
—CO-Gly;
—CO-Sar;
—$CH(COOH)_2$;
—$N(CH_2COOH)_2$;
—$SO_3H$
—$OSO_3H$
—$OPO3H_2$
—$PO_3H_2$ or
-tetrazol-5-yl
and any $Zn^{2+}$ complex thereof 14. Insulin derivative according to paragraph 13, wherein $Q_1$ is an amino acid amide of an amino acid with a carboxylic acid in the side chain, or an amino acid with an uncharged side chain, the amino acid amide residue or amino acid residue having from 2 to 10 carbon atoms.

15. Insulin derivative according to any of paragraphs 13-14, wherein $Q_1$ is selected from the group consisting of β-D-Asp-amide, β-L-Asp-amide, γ-L-Glu-amide and γ-D-Glu-amide.

16. Insulin derivative according to paragraph 13, wherein $Q_1$ is a chain composed of two, three or four α-amino acid amide residues and/or amino acid residues with an uncharged side chain.

17. Insulin derivative according to paragraphs 13 or 16, wherein $Q_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

18. Insulin derivative according to any of paragraphs 13-17, wherein $Q_2$ is a bond.

19. Insulin derivative according to paragraphs 13-17, wherein $Q_2$ is selected from the group consisting of
—$COCH(CONH_2)$—
—$COCH_2N(CH_2CONH_2)$—
—$COCH_2N(CH_2CONH_2)COCH_2N(CH_2CONH_2)$
—$COCH_2CH_2N(CH_2CH_2CONH_2)$—
—$COCH_2CH_2N(CH_2CH_2CONH_2)$—$COCH_2CH_2N(CH_2CH_2CONH_2)$—
—$COCH_2N(CH_2CH_2CONH_2)$—
—$COCH_2CH_2N(CH_2CONH_2)$—
—$COCH_2OCH_2CONH$—;
—CO—$((CR^5R^6)_{1-6}$—NH—CO$)_{1-4}$—; or
—CO—$((CR^5R^6)_{1-6}$—CO—NH$)_{1-4}$—, where $R^5$ independently can be H, —$CH_3$, —$(CH_2)_{1-6}CH_3$ or —$CONH_2$ and $R^6$ independently can be H, —$CH_3$, —$(CH_2)_{1-6}CH_3$ 20. Insulin derivative according to paragraph 19, wherein $Q_2$ is selected from the group consisting of —$COCH_2OCH_2CONH$—, —CO—$((CH_2)_2$—NH—CO$)_1$—, —CO—$((CH_2)_3$—NH—CO$)_1$—, —CO—$((CH_2)_4$—NH—CO$)_1$— and —CO—$((CH_2)_5$—NH—CO$)_1$—.

21. Insulin derivative according to paragraphs 13 or 19-21, wherein $Q_1$ is a bond.

22. Insulin derivative according to any of paragraphs 13-21, wherein $X_1$ is —C=O.

23. Insulin derivative according to any of paragraphs 13-22, wherein $Q_3$ is —$(CH_2)_m$— where m is an integer in the range of 6 to 32 or from 8 to 20.

24. Insulin derivative according to paragraph 23, where m is 12, 13, 14, 15 or 16.

25. Insulin derivative according to paragraphs 13-22, wherein $Q_3$ is a divalent hydrocarbon chain comprising 1, 2 or 3 —CH=CH— groups and a number of —$CH_2$— groups sufficient to give a total number of carbon atoms in the chain in the range of 4 to 32.

26. Insulin derivative according to any of paragraphs 13-25, wherein Z is —COOH.

27. Insulin derivative according to any of paragraphs 13-25, wherein Z is —$CH(COOH)_2$.

28. An insulin derivative according to any of paragraphs 13-25, wherein Z is —$N(CH_2COOH)_2$.

29. An insulin derivative according to any of paragraphs 13-25, wherein Z is —$SO_3H$.

30. An insulin derivative according to any of paragraphs 13-25, wherein Z is —$PO_3H$.

31. Insulin derivative according to any of paragraphs 13-30 wherein the insulin derivative is selected from the group consisting of
$N^{\epsilon B29}$-ω-carboxy-pentadecanoyl-γ-L-glutamylamide desB30 human insulin,
$N^{\epsilon B29}$-ω-carboxy-pentadecanoyl-γ-amino-butanoyl desB30 human insulin,
$N^{\epsilon B29}$-ω-carboxy-tetradecanoyl-γ-L-glutamylamide desB30 human insulin,
$N^{\epsilon B29}$-ω-carboxy-tridecanoyl-γ-L-glutamylamide desB30 human insulin,
$N^{\epsilon B29}$-ω-carboxy-pentadecanoyl-β-alanyl desB30 human insulin,
$N^{\epsilon B29}$-ω-carboxy-pentadecanoyl-γ-L-aspartylamide desB30 human insulin,
$N^{\epsilon B29}$-ω-carboxy-pentadecanoyl-ε-aminohexanoyl desB30 human insulin,
$N^{\epsilon B29}$-ω-carboxy-pentadecanoyl-δ-aminopentanoyl desB30 human insulin,
$N^{\epsilon B29}$-ω-carboxy-tridecanoyl-γ-amino-butanoyl desB30 human insulin
$N^{\epsilon B29}$-ω-carboxy-undecanoyl-δ-amino-butanoyl desB30 human insulin and
$N^{\epsilon B29}$-ω-carboxy-tetradecanoyl-γ-amino-butanoyl desB30 human insulin 32. Insulin derivative according to paragraph 2 or 4, wherein
$Q_3$ is:
—CO—$((CR^5R^6)_{1-6}$—NH—CO$)$—;
—(CO—$(CR^5R^6)_{1-6}$—CO—NH$)_{1-4}$—, where $R^5$ independently can be H, —$CH_3$, —$(CH_2)_{1-6}CH_3$ or —$CONH_2$ and $R^6$ independently can be H, —$CH_3$, —$(CH_2)_{1-6}CH_3$;

—CO—$(CH_2)_{0-3}$—Ar—$(CH_2)_{0-3}$— where Ar can be arylene or heteroarylene, which may be substituted with one or two groups selected from the group consisting of —$CH_3$, —$(CH)_{1-6}$—$CH_3$, —$CONR^1R^2$ or —$SO_2NR^1R^2$ where $R^1$ and $R^2$ independently of each other can be H, —$CH_3$ or —$(CH)_{1-6}$—$CH_3$; or a bond $Q_4$ is:
—$(CH_2)_m$— where m is an integer from 4 to 22;

a divalent hydrocarbon chain comprising 1, 2 or 3 —CH═CH— groups and a number of —$CH_2$— groups sufficient to give a total number of carbon atoms in the chain in the range of 4 to 22;

arylene or heteroarylene, which may be substituted with one or two groups selected from the group consisting of —$CH_3$, —$(CH)_{1-6}$—$CH_3$, —$CONR^1R^2$ or —$SO_2NR^1R^2$, where $R^1$ and $R^2$, independently of each other can be H, —$CH_3$ or —$(CH)_{1-6}$—$CH_3$; or a chain of the formula

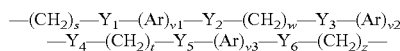

wherein Ar is defined as above, $Y_1$-$Y_6$ independently of each other can be O, S, S═O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur;

$X_1$ is:
O;
—C═O
$NCOR^1$, where $R^1$ can be H, —$CH_3$ or —$(CH)_{1-6}$—$CH_3$; or

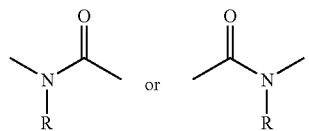

where R is hydrogen, $C_{1-3}$-alkyl, $C_{2-3}$-alkenyl or $C_{2-3}$-alkynyl;
with the proviso that when $X_1$ is O, then $X_1$ does not bind directly to O in $Q_4$;

$X_2$, $X_3$ and $Q_5$ are bonds;
All values of n are zero; and
Z is:
—COOH;
—CO-Asp;
—CO-Glu;
—CO-Gly;
—CO-Sar;
—$CH(COOH)_2$;
—$N(CH_2COOH)_2$;
—$SO_3H$
—$OSO_3H$
—$OPO3H_2$
—$PO_3H_2$ or
-tetrazol-5-yl or
—O—$W_1$,
where $W_1$ is arylene or heteroarylene, which may be substituted with one or two groups selected from the group consisting of tetrazo-5-lyl, —COOH, —$SO_3H$, —$(CH_2)_{1-6}$—$SO_3H$, —$(CH_2)_{1-6}$—O—$PO_3H_2$, —$CONR^3R^4$ or —$SO_2NR^3R^4$, where $R^3$ and $R^4$ independently of each other can be H, —$(CH_2)_{1-6}$—$SO_3H$, or —$(CH_2)_{1-6}$—O—$PO_3H_2$; and any $Zn^{2+}$ complex thereof.

33. Insulin derivative according to paragraphs 2, 4 or 32, wherein $Q_1$ is an amino acid amide of an amino acid with a carboxylic acid in the side chain, or an amino acid with an uncharged side chain, the amino acid amide residue or amino acid residue having from 2 to 10 carbon atoms.

34. Insulin derivative according to paragraphs 2, 4 or 33, wherein $Q_1$ is selected from the group consisting of β-D-Asp-amide, β-L-Asp-amide, γ-L-Glu-amide and γ-D-Glu-amide.

35. Insulin derivative according to paragraph 2, 4 or 34, wherein $Q_1$ is a chain composed of two, three or four α-amino acid amide residues or amino acid residues with an uncharged side chain.

36. Insulin derivative according to paragraphs 2, 4 or 35, wherein $Q_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

37. Insulin derivative according to any of paragraphs 2, 4 or 32-36, wherein $Q_2$ is a bond.

38. Insulin derivative according to paragraphs 2, 4 or 32-36, where $Q_2$ is —CO—$CH_2$—$(CHCONH_2)$—NH—CO; —CO—$(CH_2)_2$—$(CHCONH_2)$—NH—CO— or —CO—$(CH_2)_3$—$(CHCONH_2)$—NH—CO)—.

39. Insulin derivative according to paragraph 2, 4 or 38, wherein $Q_1$ is a bond.

40. Insulin derivative according to paragraphs 32-39, wherein $Q_3$ is —$(CH_2)_s$—$Y_1$—$(Ar)_{v1}$—$Y_2$—$(CH_2)_w$—$Y_3$—$(Ar)_{v2}$—$Y_4$—$(CH_2)_t$—$Y_5$—$(Ar)_{v3}$—$Y_6$—$(CH_2)_z$—
wherein Ar is defined as above, $Y_1$-$Y_6$ independently of each other can be O, S, S═O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur.

41. Insulin derivative according to any of paragraph 40, wherein at least two of $v_1$, $v_2$, or $v_3$ are zero.

42. Insulin derivative according to any of paragraphs 40-41, wherein $Y_1$-$Y_6$ are bonds.

43. Insulin derivative according to any of paragraphs 40-41, wherein at least one of $Y_1$-$Y_6$ are O or S.

44. Insulin derivative according to any of paragraphs 40-41 or 43, wherein $Y_1$ is O or S and $v_1$ is one.

45. Insulin derivative according to any of paragraphs 40-44, wherein s is 6, 7, 8, 9 or 10.

46. Insulin derivative according to any of paragraphs 40-45, wherein $X_1$, $X_2$, $X_3$, $Q_4$, and $Q_5$ are bonds and Ar is $C_6H_4$.

47. Insulin derivative according to any of paragraphs 32-46, wherein n is zero.

48. Insulin derivative according to any of paragraphs 32-47, wherein Z is —COOH.

49. Insulin derivative according to any of paragraphs 32-47, wherein Z is —$CH(COOH)_2$.

50. An insulin derivative according to any of paragraphs 32-47, wherein Z is —$N(CH_2COOH)_2$.

51. An insulin derivative according to any of paragraphs 32-47, wherein Z is —SO$_3$H.

52. An insulin derivative according to any of paragraphs 32-47, wherein Z is —PO$_3$H.

53. An insulin derivative according to any of paragraphs 32-47, wherein Z is —O—W$_1$, where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^{13}$R$^{14}$ or —SO$_2$NR$^{13}$R$^{14}$ where R$^{13}$ and R$^{14}$, independently of each other can be H, —(CH$_2$)$_{1-6}$—SO$_3$H, or —(CH$_2$)$_{1-6}$—O—PO$_3$H$_2$.

54. Insulin derivative according to any of paragraphs 32-53 wherein the insulin derivative is N$^{\epsilon B29}$-10-(4-carboxyphenoxy)-decanoyl-γ-L-glutamylamide desB30 human insulin.

55. Insulin derivative according to paragraph 1, wherein Q$_1$ is an amino acid amide of an amino acid with a carboxylic acid in the side chain, or an amino acid with an uncharged side chain, the amino acid amide residue or amino acid residue having from 2 to 10 carbon atoms.

56. Insulin derivative according to any of paragraphs 1 or 55, wherein Q$_1$ is selected from the group consisting of β-D-Asp-amide, β-L-Asp-amide, γ-L-Glu-amide and γ-D-Glu-amide.

57. Insulin derivative according to paragraph 1, wherein Q$_1$ is a chain composed of two, three or four α-amino acid amide residues or amino acid residues with an uncharged side chain.

58. Insulin derivative according to paragraphs 1 or 57, wherein Q$_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

59. Insulin derivative according to any of paragraphs 1 or 55-58, wherein Q$_2$ is a bond.

60. Insulin derivative according to any of paragraphs 1 or 55-58, wherein Q$_2$ is selected from the group consisting of —CO—(CR$^5$R$^6$)$_{1-6}$—NH—CO— and —(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;

61. Insulin derivative according to paragraphs 1 or 60, where Q$_2$ is —CO—((CH$_2$)$_3$—NH—CO)—, —CO—CH$_2$—(CHCONH$_2$)—NH—CO; —CO—(CH$_2$)$_2$—(CHCONH$_2$)—NH—CO)— or —CO—(CH$_2$)$_3$—(CHCONH$_2$)—NH—CO)—

62. Insulin derivative according to paragraphs 1 or 60-61, wherein Q$_1$ is a bond.

63. Insulin derivative according to paragraph 55-62, wherein Q$_3$ is —(CH$_2$)$_s$—Y$_1$—(Ar)$_{v1}$—Y$_2$—(CH$_2$)$_w$—Y$_3$—(Ar)$_{v2}$—Y$_4$—(CH$_2$)$_t$—Y$_5$—(Ar)$_{v3}$—Y$_6$—(CH$_2$)$_z$— wherein Ar is defined as above, Y$_1$-Y$_6$ independently of each other can be O, S, S=O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other and that the structure —O—(CH$_2$)$_1$—O— does not occur.

64. Insulin derivative according to paragraph 63, wherein at least two of v$_1$, v$_2$, or v$_3$ are zero.

65. Insulin derivative according to any of paragraphs 63-64, wherein Y$_1$-Y$_6$ are bonds.

66. Insulin derivative according to any of paragraphs 63-64, wherein at least one of Y$_1$—Y$_6$ are O or S.

67. Insulin derivative according to any of paragraphs 63-64 or 66, wherein Y$_1$ is O or S and v$_1$ is one.

68. Insulin derivative according to any of paragraphs 63-67, wherein s is 6, 7, 8, 9 or 10.

69. Insulin derivative according to any of paragraphs 55-68, wherein X$_1$, X$_2$, X$_3$, Q$_4$, and Q$_5$ are bonds and Ar is C$_6$H$_4$.

70. Insulin derivative according to any of paragraphs 55-69, wherein n is zero.

71. Insulin derivative according to any of paragraphs 55-70, wherein Z is —COOH.

72. Insulin derivative according to any of paragraphs 55-70, wherein Z is —CH(COOH)$_2$.

73. An insulin derivative according to any of paragraphs 55-70, wherein Z is —N(CH$_2$COOH)$_2$.

74. An insulin derivative according to any of paragraphs 55-70, wherein Z is —SO$_3$H.

75. An insulin derivative according to any of paragraphs 55-70, wherein Z is —PO$_3$H.

76. An insulin derivative according to any of paragraphs 55-70, wherein Z is —O—W$_1$, where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^{13}$R$^{14}$ or —SO$_2$NR$^{13}$R$^{14}$ where R$^{13}$ and R$^{14}$, independently of each other can be H, —(CH$_2$)$_{1-6}$—SO$_3$H, or —(CH$_2$)$_{1-6}$—O—PO$_3$H$_2$.

77. Insulin derivative according to any of paragraphs 1 or 55-70 wherein the insulin derivative are selected from the group consisting of N$^{\epsilon B29}$-10-(4-carboxyphenoxy)-decanoyl-γ-L-glutamylamide desB30 human insulin, N$^{\epsilon B29}$-4-[11-(4-Carboxyphenyl)undecanoylamino]butyryl desB30 human insulin.

78. Insulin derivative according to paragraph 3, wherein Q$_1$ is an amino acid amide of an amino acid with a carboxylic acid in the side chain having from 2 to 10 carbon atoms.

79. Insulin derivative according to any of paragraphs 3 or 77, wherein Q$_1$ is selected from the group consisting of β-D-Asp-amide, β-L-Asp-amide, γ-L-Glu-amide and γ-D-Glu-amide.

80. Insulin derivative according to paragraphs 3, wherein Q$_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

81. Insulin derivative according to any of paragraphs 3 or 77-79, wherein Q$_2$ is a bond.

82. Insulin derivative according to paragraphs 3 or 77-80, wherein Q$_2$ is selected from the group consisting of
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—

—COCH$_2$CH$_2$N(CH$_2$CONH$_2$)—
—COCH$_2$OCH$_2$CONH—;
—CO—((CR$^5$R$^6$)$_{1-6}$—NH—CO)$_{1-4}$—; or
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$ provided that Q$_2$ comprises a non-linking amide if Q$_1$ is a bond.

83. Insulin derivative according to paragraphs 3 or 82, wherein Q$_1$ is a bond.

84. Insulin derivative according to paragraph 78-83, wherein Q$_3$ is —(CH$_2$)$_s$—Y$_1$—(Ar)$_{v1}$—Y$_2$—(CH$_2$)$_w$—Y$_3$—(Ar)$_{v2}$—Y$_4$—(CH$_2$)$_t$—Y$_5$—(Ar)$_{v3}$—Y$_6$—(CH$_2$)$_z$— wherein Ar is defined as above, Y$_1$-Y$_6$ independently of each other can be O, S, S=O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other and that the structure —O—(CH$_2$)$_1$—O— does not occur.

85. Insulin derivative according to paragraph 84, wherein at least two of v$_1$, v$_2$, or v$_3$ are zero.

86. Insulin derivative according to any of paragraphs 84-85, wherein Y$_1$-Y$_6$ are bonds.

87. Insulin derivative according to any of paragraphs 84-85, wherein at least one of Y$_1$—Y$_6$ are O or S.

88. Insulin derivative according to any of paragraphs 84-85 or 87, wherein Y$_1$ is O or S and v$_1$ is one.

89. Insulin derivative according to any of paragraphs 84-88, wherein s is 6, 7, 8, 9 or 10.

90. Insulin derivative according to any of paragraphs 78-89, wherein X$_1$, X$_2$, X$_3$, Q$_4$, and Q$_5$ are bonds and Ar is C$_6$H$_4$.

91. Insulin derivative according to any of paragraphs 78-90, wherein n is zero.

92. Insulin derivative according to any of paragraphs 78-91, wherein Z is —COOH.

93. Insulin derivative according to any of paragraphs 78-91, wherein Z is —CH(COOH)$_2$.

94. An insulin derivative according to any of paragraphs 78-91, wherein Z is —N(CH$_2$COOH)$_2$.

95. An insulin derivative according to any of paragraphs 78-91, wherein Z is —SO$_3$H.

96. An insulin derivative according to any of paragraphs 78-91, wherein Z is —PO$_3$H.

97. An insulin derivative according to any of paragraphs 78-91, wherein Z is —O—W$_1$, where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^{13}$R$^{14}$ or —SO$_2$NR$^{13}$R$^{14}$ where R$^{13}$ and R$^{14}$ independently of each other can be H, —(CH$_2$)$_{1-6}$—SO$_3$H, or —(CH$_2$)$_{1-6}$—O—PO$_3$H$_2$.

98. Insulin derivative according to any of paragraphs 3 or 78-97, wherein the insulin derivative are selected from the group consisting of:
N$^{\epsilon B29}$-10-(4-carboxyphenoxy)-decanoyl-γ-L-glutamylamide desB30 human insulin,
N$^{\epsilon B29}$-4-[11-(4-Carboxyphenyl)undecanoylamino]butyryl desB30 human insulin and
N$^{\epsilon B29}$-{4-[10-(4-Carboxy-phenoxy)-decanoylamino]-butyryl} desB30 insulin 99. Insulin derivative according to paragraphs 1 or 2, wherein Q$_1$ is an amino acid amide of an amino acid with a carboxylic acid in the side chain, or an amino acid with an uncharged side chain, the amino acid amide residue or amino acid residue having from 2 to 10 carbon atoms.

100. Insulin derivative according to any of paragraphs 1, 2 or 99, wherein Q$_1$ is selected from the group consisting of β-D-Asp-amide, β-L-Asp-amide, γ-L-Glu-amide and γ-D-Glu-amide.

101. Insulin derivative according to paragraph 1 or 2, wherein Q$_1$ is a chain composed of two, three or four α-amino acid amide or amino acid residues with uncharged side chains.

102. Insulin derivative according to paragraphs 1, 2 or 101, wherein Q$_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

103. Insulin derivative according to any of paragraphs 99-102, wherein Q$_2$ is a bond 104. Insulin derivative according to any of paragraphs 1, 2 or 99-102, wherein Q$_2$ is selected from the group consisting of —CO—((CR$^5$R$^6$)$_{1-6}$—NH—CO)— and —(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;

105. Insulin derivative according to any of paragraphs 1, 2 or 99-104, wherein Q$_2$ is —CO—CH$_2$—(CHCONH$_2$)—NH—CO; —CO—(CH$_2$)$_2$—(CHCONH$_2$)—NH—CO)— or —CO—(CH$_2$)$_3$—(CHCONH$_2$)—NH—CO)—

106. Insulin derivative according to paragraphs 1, 2 or 104-105, wherein Q$_1$ is a bond.

107. Insulin derivative according any of paragraphs 99-106, wherein one of Q$_3$, Q$_4$, or Q$_5$ is —(CH$_2$)$_m$— where m is an integer in the range of 1 to 32 or 1-12.

108. Insulin derivative according to paragraph 107, wherein m is 4, 5, 6, 8, 9, 10 or 11.

109. Insulin derivative according to any of paragraphs 99-108, wherein one of Q$_3$, Q$_4$, or Q$_5$ is (CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—; —(CH$_2$OCH$_2$)$_y$— where y is 1-20.

110. Insulin derivative according to paragraph 109, wherein one of Q$_3$, Q$_4$, or Q$_5$ is (CH$_2$CH$_2$O)$_y$— or (CH$_2$CH$_2$OCH$_2$CH$_2$CH$_2$O)$_y$ wherein y is in the range of 1-12, 2-4 or 2-3

111. Insulin derivative according to any of paragraphs 109-110, wherein y is 1.

112. Insulin derivative according to any of paragraphs 99-111, wherein X$_1$, X$_2$ and X$_3$ are independently of each other

O;

—C=O a bond;

NCOR$^1$, where R$^1$ can be H, —CH$_3$ or —(CH)$_{1-6}$—CH$_3$; or

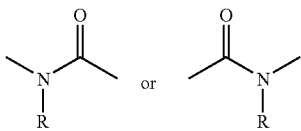

where R is hydrogen, $C_{1-3}$-alkyl, $C_{2-3}$-alkenyl or $C_{2-3}$-alkynyl;

113. Insulin derivative according to any of paragraphs 99-112, wherein $X_1$, $X_2$ and $X_3$ are:

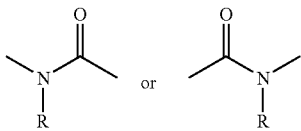

where R is hydrogen, $C_{1-3}$-alkyl, $C_{2-3}$-alkenyl or $C_{2-3}$-alkynyl;

114. Insulin derivative according to any of paragraphs 99-113, wherein $X_1$ is

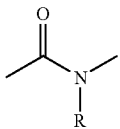

where R is H and wherein $X_2$ is

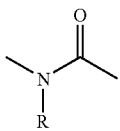

where R is H.

115. Insulin derivative according to any of paragraphs 99-114, wherein n is 0, 1, 2 or 3.
116. Insulin derivative according to any of paragraphs 99-115, wherein Z is —COOH.
117. Insulin derivative according to any of paragraphs 99-115, wherein Z is —CH(COOH)$_2$.
118. An insulin derivative according to any of paragraphs 99-115, wherein Z is —N(CH$_2$COOH)$_2$.
119. An insulin derivative according to any of paragraphs 99-115, wherein Z is —SO$_3$H.
120. An insulin derivative according to any of paragraphs 99-115, wherein Z is —PO$_3$H.
121. Insulin derivative according to any of paragraphs 1-2 or 99-120 wherein the insulin derivative is
N$^{\epsilon B29}$-(3-(3-{4-[3-(7-carboxyheptanoylamino)propoxy]butoxy}propylcarbamoyl)-propionyl-γ-glutamylamide) desB30 human Insulin.

In one aspect of the invention $Q_1$ is an amino acid amide of an amino acid with a carboxylic acid in the side chain, or an amino acid with an uncharged side chain, the amino acid amide residue or amino acid residue having from 2 to 10 carbon atoms.

$Q_1$ can also be a chain composed of two, three or four amino acid amide of an amino acid with a carboxylic acid in the side chain and/or an amino acid with an uncharged side chain The chain of amino acids may comprise at least one amino acid containing an amide. Thus, $Q_1$ can, for example, be selected from the group comprising β-L-Asp-amide, β-D-Asp-amide, γ-L-Glu-amide and γ-D-Glu-amide.

In one aspect $Q_1$ is a chain composed of two uncharged amino acid residues, which has from 4 to 10 carbon atoms. The amino acids can comprise an amide. Examples of such amino acid residues are β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide, In one aspect of the invention $Q_1$ is a chain composed of three amino acid residues, independently having from 4 to 10 carbon atoms, where at least one of the amino acid residues of the chain being selected from the group of residues having an amide. The combination of the three amino acid amides can be any combination of β-L-Asp-amide, β-D-Asp-amide, γ-L-Glu-amide and γ-D-Glu-amide, which means that 64 different combinations are possible.

In a further aspect, $Q_1$ is a chain composed of four amino acid residues, independently having from 4 to 10 carbon atoms, where at least one of the amino acid residues of the chain being selected from the group of residues having an amide. The combination of the four amino acid amides can be any combination of β-L-Asp-amide, β-D-Asp-amide, γ-L-Glu-amide and γ-D-Glu-amide, which means that 256 different combinations are possible.

122. An insulin derivative having a substituent attached to desB30 human insulin at either the α-amino group of the N-terminal amino acid residue of the B chain or at an ε-amino group of a Lys residue present in the A or B chain of desB30 human insulin, which substituent comprises at least one fatty difunctionalized moiety with about 6 to about 32 carbon atoms and an uncharged linker of the formula —CO—((CH$_2$)$_{1-6}$—NH—CO)$_{1-4}$ which links the fatty difunctionalized moiety to desB30 human insulin, wherein the fatty difunctionalized moiety comprises an aromatic group.
123. Insulin derivative according to paragraph 122, wherein the uncharged linker is selected from the group consisting of: —CO—CH$_2$—NH—CO, —CO—(CH$_2$)$_2$—NH—CO, —CO—(CH$_2$)$_3$—NH—CO and —CO—(CH$_2$)$_1$—NH—CO.
124. Insulin derivative according to paragraphs 122 or 123, wherein the fatty difunctionalized moiety is T-(CH$_2$)$_s$—Y$_1$—(Ar)$_{v1}$—Y$_2$—(CH$_2$)$_w$—Y$_3$—(Ar)$_{v2}$—Y$_4$—(CH$_2$)$_t$—Y$_5$—(Ar)$_{v3}$—Y$_6$—(CH$_2$)$_z$-T wherein Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$ where R$^1$ and R$^2$, independently of each other can be H, —CH$_3$ or —(CH)$_{1-6}$—CH$_3$;

Y$_1$-Y$_6$ independently of each other can be O, S, S═O, SO$_2$ or a bond;

s, w, t and z independently of each other are zero or an integer from 1 to 10 so that the sum of s, w, t and z is in the range from 4 to 30, v$_1$, v$_2$, and v$_3$ independently of each other can be zero or 1 with the proviso that Y$_1$-Y$_6$ do not link to each other and that the structure —O—(CH$_2$)$_1$—O— does not occur; and T is a functional group selected from carboxy, amino or hydroxyl groups.

125. Insulin derivative according to paragraphs 122-124, wherein the insulin derivative is $N^{\epsilon B29}$-4-[11-(4-Carboxyphenyl)undecanoylamino]butyryl desB30 human insulin.

126. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that the uncharged linker does not comprise —(CO—(CH$_2$)$_{1-6}$—NH—CO)$_{1-4}$— if the insulin substituent comprises an aromatic group and that the substituent does not comprise one or more residues selected from the group of —CO—(CH$_2$)$_2$—CO—NH—(CH$_2$CH$_2$O)$_2$—, —CO—(CH$_2$)$_2$—CO—NH—CH$_2$—(CH$_2$CH$_2$O)$_2$—, —CO—(CH$_2$)$_2$—CO—NH—(CH$_2$CH$_2$O)$_3$— and —CO—(CH$_2$)$_2$—CO—NH—CH$_2$—(CH$_2$CH$_2$OCH$_2$CH$_2$CH$_2$CH$_2$O)—.

127. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that the substituent does not comprise one or more residues selected from the group of —CO—(CH$_2$)$_2$—CO—NH—(CH$_2$CH$_2$O)$_2$—, —CO—(CH$_2$)$_2$—CO—NH—CH$_2$—(CH$_2$CH$_2$O)$_2$—, —CO—(CH$_2$)$_2$—CO—NH—(CH$_2$CH$_2$O)$_3$— and —CO—(CH$_2$)$_2$—CO—NH—CH$_2$—(CH$_2$CH$_2$OCH$_2$CH$_2$CH$_2$CH$_2$O)—.

128. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that the substituent does not comprise one or more residues selected from the group of —CO—(CH$_2$)$_2$—CO—NH—(CH$_2$CH$_2$O)$_2$—, —CO—(CH$_2$)$_2$—CO—NH—CH$_2$—(CH$_2$CH$_2$O)$_2$—, —CO—(CH$_2$)$_2$—CO—NH—(CH$_2$CH$_2$O)$_3$— and —CO—(CH$_2$)$_2$—CO—NH—CH$_2$—(CH$_2$CH$_2$OCH$_2$CH$_2$CH$_2$CH$_2$O)— characterized by the uncharged linker being selected from the group consisting of
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins
—COCH(CONH$_2$)—
—COCH$_2$N(CH$_2$CONH$_2$)—
—COCH$_2$N(CH$_2$CONH$_2$)COCH$_2$N(CH$_2$CONH$_2$)—
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—; or
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$ provided that if an amine in the uncharged linker forms a bond with the rest of the substituent, the amine must be bound to the rest of the substituent via a carbonyl group.

129. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that the uncharged linker does not comprise —(CO—(CH$_2$)$_{1-6}$—NH—CO)$_{1-4}$— if the insulin substituent comprises an aromatic group and that the substituent does not comprise one or more residues selected from the group of —CO—(CH$_2$)$_2$—CO—NH—(CH$_2$CH$_2$O)$_2$—, —CO—(CH$_2$)$_2$—CO—NH—CH$_2$—(CH$_2$CH$_2$O)$_2$—, —CO—(CH$_2$)$_2$—CO—NH—(CH$_2$CH$_2$O)$_3$— and —CO—(CH$_2$)$_2$—CO—NH—CH$_2$—(CH$_2$CH$_2$OCH$_2$CH$_2$CH$_2$CH$_2$O)— characterized by the uncharged linker being selected from the group consisting of
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins,
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—; or
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$, provided that if an amine in the uncharged linker forms a bond with the rest of the substituent, the amine must be bound to the rest of the substituent via a carbonyl group.

130. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that the substituent does not comprise one or more residues selected from the group of —CO—(CH$_2$)$_2$—CO—NH—(CH$_2$CH$_2$O)$_2$—, —CO—(CH$_2$)$_2$—CO—NH—CH$_2$—(CH$_2$CH$_2$O)$_2$—, —CO—(CH$_2$)$_2$—CO—NH—(CH$_2$CH$_2$O)$_3$— and —CO—(CH$_2$)$_2$—CO—NH—CH$_2$—(CH$_2$CH$_2$OCH$_2$CH$_2$CH$_2$CH$_2$O)— characterized by the uncharged linker being selected from the group consisting of an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, —COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—; or
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$ provided that if an amine in the uncharged linker forms a bond with the rest of the substituent, the amine must be bound to the rest of the substituent via a carbonyl group.

131. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that a non-linking amide is present in the linker if the substituent comprises an aromatic group and that the substituent does not comprise one or more residues selected from the group of —CO—(CH$_2$)$_2$—CO—NH—(CH$_2$CH$_2$O)$_2$—, —CO—(CH$_2$)$_2$—CO—NH—CH$_2$—(CH$_2$CH$_2$O)$_2$—, —CO—(CH$_2$)$_2$—CO—NH—(CH$_2$CH$_2$O)$_3$— and —CO—(CH$_2$)$_2$—CO—NH—CH$_2$—(CH$_2$CH$_2$OCH$_2$CH$_2$CH$_2$CH$_2$O)—.

132. An insulin derivative having a substituent attached to a parent insulin moiety at either the α-amino group of the N-terminal amino acid residue of the B chain or at an ε-amino group of a Lys residue present in the A or B chain of the parent insulin moiety, which substituent comprises at least one fatty difunctionalized moiety with about 6 to about 32 carbon atoms and an uncharged linker which links the fatty difunctionalized moiety to the parent insulin, provided that the fatty difunctionalized moiety is an aliphatic chain, an non-linking amide is present in the linker.

133. Insulin derivative according to paragraph 121-129, wherein the substituent is attached to the α-amino group of the N-terminal amino acid residue of the B chain of the parent insulin.

134. Insulin derivative according to paragraph 121-129, wherein the substituent is attached to the ε-amino group of a Lys residue present in the A or B chain of the parent insulin.

135. Insulin derivative according to paragraphs 121-129 or 131 wherein the substituent is attached to the ε-amino group of the Lys residue in position B29 present in the B chain of the parent insulin.

136. Insulin derivative according to paragraph 132, wherein the substituent is attached to the ε-amino group of the Lys residue in position B29 in desB30 human insulin 137. Insulin derivative according to any of paragraphs 121-129, wherein the linker comprises an amide or an N-substituted amide of the formula —CONR$^7$R$^8$ where R$^7$ and R$^8$, independently of each other can be hydrogen, methyl, ethyl, propyl or isopropyl.

138. Insulin derivative according to paragraph 134, where R$^7$ and R$^8$ are hydrogen.

139. Insulin derivative according to paragraph 121-129, wherein the linker comprises a non-linking amide.

140. Insulin derivative according to any of paragraphs 121-129, wherein the substituent comprises one or more residues of ethyleneglycol, propyleneglycol and/or butyleneglycol containing independently at each termini a group selected from —NH$_2$ and —COOH, which is used to connect the individual components of the substituent.

141. Insulin derivative according to paragraphs 121-129, wherein the substituent comprises at least one aromatic group.

142. Insulin derivative according to any of the paragraphs 1-141, wherein the parent insulin is human insulin or porcine insulin.

143. Insulin derivative according to any of the paragraphs 1-141, wherein the parent insulin is an insulin analogue.

144. Insulin derivative according to any of paragraphs 143, wherein the amino acid residue at position B30 of the parent insulin is Lys or has been deleted.

145. Insulin derivative according to paragraphs 143-44, wherein the parent insulin is desB30 human insulin.

146. Insulin derivative according to any of paragraphs 143-145, wherein the amino acid residue at position B1 of the parent insulin has been deleted.

147. Insulin derivative according to any of paragraphs 143-146, wherein the amino acid residue in position A21 of the parent insulin is Gly or Asn.

148. Insulin derivative according to any of paragraphs 143-147, wherein the amino acid residue at position B3 of the parent insulin is Lys.

149. Insulin derivative according to any of paragraphs 143-148, wherein the amino acid residue at position B28 of the parent insulin is Asp or Lys.

150. Insulin derivative according to any of paragraphs 143-149, wherein the amino acid residue at position B29 of the parent insulin is Pro or Thr.

151. Insulin derivative according to paragraph 149, wherein the parent insulin is AspB28 human insulin.

152. Insulin derivative according to paragraph 147, wherein the parent insulin is GlyA21 human insulin or GlyA21desB30 human insulin or GlyA21ArgB31ArgB32 human insulin.

153. Insulin derivative according to paragraph 148, wherein the parent insulin is LysB3GluB29 human insulin.

154. Insulin derivative according to paragraph 149-150, wherein the parent insulin is LysB28ProB29 human insulin.

155. Insulin derivative according to paragraph 144 and 150, wherein the parent insulin is ThrB29LysB30 human insulin.

156. A zinc complex of an insulin derivative according to any one of the preceding paragraphs wherein two zinc ions, three zinc ions, four zinc ions, five zinc ions, six zinc ions, seven zinc ions, eight zinc ions, nine zinc ions or ten six zinc ions are bound per six molecules of insulin derivative.

157. A pharmaceutical composition for the treatment of diabetes in a patient in need of such treatment, comprising a therapeutically effective amount of an insulin derivative according to paragraphs 1-155 or a zinc complex according to paragraph 156 together with a pharmaceutically acceptable carrier.

158. A pharmaceutical composition for the treatment of diabetes in a patient in need of such treatment, comprising a therapeutically effective amount of an insulin derivative according to paragraphs 1-155 or a zinc complex according to paragraph 156 in mixture with an insulin or an insulin analogue which has a rapid onset of action, together with a pharmaceutically acceptable carrier.

159. A method of treating diabetes in a patient in need of such a treatment, comprising administering to the patient a therapeutically effective amount of an insulin derivative according to paragraphs 1-155 or a zinc complex according to paragraph 156 together with a pharmaceutically acceptable carrier.

160. A method of treating diabetes in a patient in need of such a treatment, comprising administering to the patient a therapeutically effective amount of an insulin derivative according to paragraphs 1-155 or a zinc complex according to paragraph 156 in mixture with an insulin or an insulin analogue which has a rapid onset of action, together with a pharmaceutically acceptable carrier.

161. A method according to paragraphs 138 or 139 for pulmonary treatment of diabetes.

162. Use of an insulin derivative according to paragraphs 1-155 or a zinc complex according to paragraph 156 for the manufacture of a pharmaceutical composition for the use in the treatment of type 1 diabetes, type 2 diabetes and other states that cause hyperglycaemia.

163. Use of an insulin derivative according to paragraphs 1-155 or a zinc complex according to paragraph 156 in mixture with an insulin or an insulin analogue which has a rapid onset of action for the manufacture of a pharmaceutical composition for the use in the treatment of type 1 diabetes, type 2 diabetes and other states that cause hyperglycaemia.

164. A mixture of an insulin derivative according to paragraphs 1-155 or a zinc complex according to paragraph 156 and a rapid acting insulin analogue selected group consisting of AspB28 human insulin; LysB28ProB29 human insulin and LysB3GluB29 human insulin.

165. An insulin derivative, wherein the insulin derivative is selected from the group consisting of:

$N^{\epsilon B29}$-ω-carboxy-pentadecanoyl-γ-L-glutamylamide desB30 human insulin, $N^{\epsilon B29}$-ω-carboxy-pentadecanoyl-γ-amino-butanoyl desB30 human insulin, $N^{\epsilon B29}$-ω-carboxy-tetradecanoyl-γ-L-glutamylamide desB30 human insulin, $N^{\epsilon B29}$-ω-carboxy-tridecanoyl-γ-L-glutamylamide desB30 human insulin, $N^{\epsilon B29}$-ω-carboxy-pentadecanoyl-β-alanyl desB30 human insulin, $N^{\epsilon B29}$-ω-carboxy-pentadecanoyl-γ-L-aspartylamide desB30 human insulin, $N^{\epsilon B29}$-ω-carboxy-pentadecanoyl-ε-aminohexanoyl desB30 human insulin, $N^{\epsilon B29}$-ω-carboxy-pentadecanoyl-δ-aminopentanoyl desB30 human insulin, $N^{\epsilon B29}$-10-(4-carboxyphenoxy)-decanoyl-γ-L-glutamylamide desB30 human insulin, $N^{\epsilon B29}$-4-[11-(4-Carboxyphenyl)undecanoylamino]butyryl desB30 human insulin, $N^{\epsilon B29}$-(3-(3-{4-[3-(7-carboxyheptanoylamino)propoxy] butoxy}propylcarbamoyl)-propionyl-γ-glutamylamide) desB30 human Insulin, $N^{\epsilon B29}$-ω-carboxy-tridecanoyl-γ-amino-butanoyl desB30 human insulin, $N^{\epsilon B29}$-ω-carboxy-undecanoyl-γ-amino-butanoyl desB30 human insulin, $N^{\epsilon B29}$-ω-carboxy-tetradecanoyl-γ-amino-butanoyl desB30 human insulin, $N^{\epsilon B29}$-{4-[10-(4-Carboxy-phenoxy)-decanoylamino]-butyryl} desB30 insulin, $N^{\epsilon B29}$-{4-[(14-Carboxy-tetradecanoylamino)-methyl]-benzoyl} desB30 insulin, $N^{\epsilon B29}$-[16-(4-Carboxy-phenoxy)-hexadecanoyl] desB30 insulin, $N^{\epsilon B29}$-{4-[(15-carboxypentadecanoylamino)benzoyl]-desB30 human insulin and $N^{\epsilon B29}$-{4-[(15-Carboxy-pentadecanoylamino)-methyl]-benzoyl}-desB30 insulin 166. Insulin derivative as described in the examples.

The invention will further be summarized in the following paragraphs:

1a. Insulin derivative having a substituent attached to a parent insulin moiety at either the α-amino group of the N-terminal amino acid residue of the B chain or at an ε-amino group of a Lys residue present in the B chain of the parent insulin moiety, which substituent comprises at least one fatty difunctionalized moiety with about 6 to about 32 carbon atoms and an uncharged linker which link the fatty difunctionalized moiety to the parent insulin, provided that the uncharged linker does not comprise —(CO—(CH$_2$)$_{2-6}$—NH—CO)$_{1-4}$— if the insulin substituent comprises an aromatic group.

2a. Insulin derivative according to paragraphs 1a, wherein the substituent is attached to the α-amino group of the N-terminal amino acid residue of the B-chain of the parent insulin.

3a. Insulin derivative according to paragraphs 1a, wherein the substituent is attached to the ε-amino group of a Lys residue present in the B-chain of the parent insulin.

4a. Insulin derivative according to paragraphs 1a or 3a wherein the substituent is attached to the ε-amino group of the Lys residue in position B29 present in the B-chain of the parent insulin.

5a. Insulin derivative according to paragraphs 4a, wherein the substituent is attached to the ε-amino group of the Lys residue in position B29 in LysB29desB30 human insulin 6a. Insulin derivative according to any of paragraphs 1a-5a, wherein the linker comprises an amide or a N-substituted amide of the formula —CONR$_7$R$_8$, where R$_7$ and R$_8$, independently of each other can be hydrogen, methyl, ethyl, propyl or isopropyl.

7a. Insulin derivative according to paragraphs 6a, where R$_7$ and R$_8$ are hydrogen.

8a. Insulin derivative according to paragraphs 1, wherein the linker comprises an amide.

9a. Insulin derivative according to any of paragraphs 1a-7a, wherein the substituent comprises one or more residues of ethyleneglycol, propyleneglycol and/or butyleneglycol containing independently at each termini a group selected from —NH$_2$ and —COOH.

10a. Insulin derivative according to paragraphs 1a-7a, wherein the substituent comprises at least one aromatic group.

11a. Insulin derivatives according to paragraphs 1a having the formula

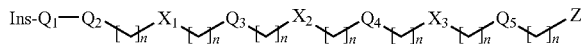

wherein Ins is the parent insulin moiety which via the α-amino group of the N-terminal amino acid residue of the B chain or an ε-amino group of a Lys residue present in the B chain of the insulin moiety is bound to is bound to $Q_1$ or $Q_2$ in the substituent;

each n is independently 0, 1, 2, 3, 4, 5 or 6;

$Q_1$ is:
- an α-amino acid amide residue having a carboxylic acid group in the substituent which residue forms, with one of its carboxylic acid groups, an amide group together with the α-amino group of the N-terminal amino acid residue of the B chain or together with the ε-amino group of a Lys residue present in the B chain of the parent insulin;
- a chain composed of two, three or four α-amino acid amide residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral substituent and amino acid residues having a carboxylic acid group in the substituent so that W has at least one amino acid residue which has a carboxylic acid group in the substituent; or
- a bond $Q_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—(CO—(CH$_2$)$_{2-6}$—NH—CO)$_{1-4}$—;
—(CO—(CH$_2$)$_{2-6}$—CO—NH)$_{1-4}$—;
—(CO—(CR$_9$R$_{10}$)$_{1-6}$—CO—NH)$_{1-4}$—, where R$_9$ and R$_{10}$, independently of each other can be H, —CH$_3$, —(CH$_2$)$_{1-6}$CH$_3$ or —CONH$_2$; or
a bond
provided that at least one of $Q_1$ or $Q_2$ is not a bond;

$Q_3$, $Q_4$, and $Q_5$ independently of each other can be
—(CH$_2$)$_m$— where m is an integer in the range of 1 to 32;
a divalent hydrocarbon chain comprising 1, 2 or 3 —CH=CH— groups and a number of —CH$_2$— groups sufficient to give a total number of carbon atoms in the chain in the range of 4 to 32;
(CH$_2$CH$_2$O)$_y$—; (CH$_2$CH$_2$CH$_2$O)$_y$—; (CH$_2$CH$_2$CH$_2$CH$_2$O)$_y$—;
(CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—;
—(CH$_2$OCH$_2$)$_y$— where y is 1-20;
—(CR$_3$R$_4$)$_{1-6}$—(NHCO—(CR$_3$R$_4$)$_{1-6}$—NHCO)$_{1-2}$—(CR$_3$R$_4$)$_{1-6}$ or —(CR$_3$R$_4$)$_{1-6}$—(CONH—(CR$_3$R$_4$)$_{1-6}$—CONH)$_{1-2}$—(CR$_3$R$_4$)$_{1-6}$—, —(CR$_3$R$_4$)$_{1-6}$—(NHCO—(CR$_3$R$_4$)$_{1-6}$—CONH)$_{1-2}$—(CR$_3$R$_4$)$_{1-6}$— or —(CR$_3$R$_4$)$_{1-6}$—(CONH—(CR$_3$R$_4$)$_{1-6}$—NHCO)$_{1-2}$—(CR$_3$R$_4$)$_{1-6}$ where R$_3$ and R$_4$ independently of each other and independently for each carbon can be H, —COOH or OH,
—(CR$_5$R$_6$)$_{1-6}$—, where R$_5$ and R$_6$ independently of each other and independently for each carbon can be H, —COOH, (CH$_2$)$_{1-6}$COOH;
—((CR$_1$R$_2$)$_{1-6}$—NR$_{15}$—CO)$_{1-4}$—, where R$_1$, R$_2$ and R$_{15}$ independently of each other can be H, —CH$_3$, —CH$_{1-6}$CH$_3$, —SO$_3$H, —(CH$_2$)$_{1-6}$—SO$_3$H, —(CH$_2$)$_{1-6}$—O—PO$_3$H$_2$ or CONH$_2$ and R$_{15}$ can be arylene which may be substituted with one or two groups of R$_1$, R$_2$ as defined above;

NR$_{15}$ where R$_{15}$ is defined as above;

arylene or heteroarylene, which may be substituted with one or two groups selected from the group consisting of —COOH, —CH$_3$, —CH$_{1-6}$CH$_3$, —SO$_3$H, —(CH$_2$)$_p$—SO$_3$H, —CONR$_1$R$_2$ or —SO$_2$NR$_1$R$_2$, where R$_1$ and R$_2$, independently of each other can be H, —CH$_3$, —(CH)$_{1-6}$—CH$_3$, —SO$_3$H, —(CH$_2$)$_{1-6}$—SO$_3$H, —(CH$_2$)$_{1-6}$—O—PO$_3$H$_2$ or CONH$_2$;

a divalent hydrocarbon chain of the formula

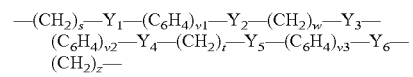

wherein $Y_1$-$Y_6$ independently of each other can be O; S or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other; or
a bond;
with the proviso that $Q_3$-$Q_5$ are different;

$X_1$, $X_2$ and $X_3$ are independently of each other:
O;
—C=O
a bond; or

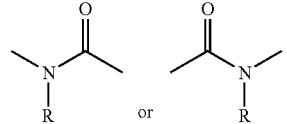

where R is hydrogen, $C_{1-3}$-alkyl, $C_{2-3}$-alkenyl or $C_{2-3}$-alkynyl;
and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—OSO$_3$H
—OPO3H$_2$
—PO$_3$H$_2$ or
-tetrazol-5-yl or
—O—W$_1$,
where W$_1$ is arylene or heteroarylene, which may be substituted with one or two groups selected from the group consisting of —COOH, —SO$_3$H, —(CH$_2$)$_{1-6}$—SO$_3$H, —CONR$_{13}$R$_{14}$ or —SO$_2$NR$_{12}$R$_{14}$, where R$_{13}$ and R$_{14}$, independently of each other can be H, —SO$_3$H, —(CH$_2$)$_{1-6}$—SO$_3$H, —(CH$_2$)$_{1-6}$—O—PO$_3$H$_2$, —CONH$_2$ or tetrazo-5-lyl; and any Zn$^{2+}$ complex thereof.

12a. Insulin derivative according to paragraphs 11a, wherein $Q_1$ is an amino acid amide residue having from 4 to 10 carbon atoms.

13a. Insulin derivative according to any of paragraphs 11a-12a, wherein $Q_1$ is selected from the group consisting of β-D-Asp-amide, β-L-Asp-amide, γ-L-Glu-amide and γ-D-Glu-amide.

14a. Insulin derivative according to paragraphs 11a, wherein $Q_1$ is a chain of amino acid amide residues.

15a. Insulin derivative according to paragraphs 11a or 14a, wherein $Q_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide, 16a. Insulin derivative according to any of paragraphs 11a-15a, wherein $Q_2$ is a bond 17a. Insulin derivative according to any of paragraphs 11a-15a, wherein $Q_2$ is selected from the group consisting of —(CO—$(CH_2)_{2-6}$—NH—CO)$_{1-4}$—; —(CO—$(CH_2)_{2-6}$—CO—NH)$_{1-4}$—;

18a. Insulin derivative according to paragraphs 17a, wherein $Q_2$ is selected from the group consisting of —(CO—$(CH_2)_2$—NH—CO)$_1$— or —(CO—$(CH_2)_3$—NH—CO)$_{1-4}$.

19a. Insulin derivative according to paragraphs 17a-18a, wherein $Q_1$ is a bond.

20a. Insulin derivative according to paragraphs 11a wherein
$Q_1$ is:
  an α-amino acid amide residue having a carboxylic acid group in the substituent which residue forms, with one of its carboxylic acid groups, an amide group together with the α-amino group of the N-terminal amino acid residue of the B chain or together with the ε-amino group of a Lys residue present in the B chain of the parent insulin;
  a chain composed of two, three or four α-amino acid amide residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral substituent and amino acid residues having a carboxylic acid group in the substituent so that W has at least one amino acid residue which has a carboxylic acid group in the substituent; or
  a bond
$Q_2$ is:
  —COCH($CONH_2$)—
  —$COCH_2N(CH_2CONH_2)$—
  —$COCH_2N(CH_2CONH_2)COCH_2N(CH_2CONH_2)$
  —$COCH_2CH_2N(CH_2CH_2CONH_2)$—
  —$COCH_2CH_2N(CH_2CH_2CONH_2)$—$COCH_2CH_2N(CH_2CH_2CONH_2)$—
  —$COCH_2N(CH_2CH_2CONH_2)$—
  —$COCH_2CH_2N(CH_2CONH_2)$—
  —(CO—$(CH_2)_{2-6}$—NH—CO)$_{1-4}$—;
  —(CO—$(CH_2)_{2-6}$—CO—NH)$_{1-4}$—;
  —(CO—$(CR_9R_{10})_{1-6}$—CO—NH)$_{1-4}$—, where $R_9$ and $R_{10}$, independently of each other can be H, —$CH_3$, —$(CH_2)_{1-6}CH_3$ or —$CONH_2$; or
  a bond
  provided that at least one of $Q_1$ or $Q_2$ is not a bond;
$Q_3$ is
  —$(CH_2)_m$— where m is an integer in the range of 6 to 32;
  a divalent hydrocarbon chain comprising 1, 2 or 3 —CH=CH— groups and a number of —$CH_2$— groups sufficient to give a total number of carbon atoms in the chain in the range of 4 to 32; or
  a divalent hydrocarbon chain of the formula —$(CH_2)_s$ $C_6H_4(CH_2)_w$— wherein v and w are integers or one of them is zero so that the sum of s and w is in the range of 6 to 30;
$X_1$, can be —C=O or a bond;
$Q_4$, $Q_5$, $X_2$ and $X_3$ are bonds;
All values of n are zero; and
Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H
  —OSO$_3$H
  —OPO3H$_2$
  —PO$_3$H$_2$ or
  -tetrazol-5-yl
and any $Zn^{2+}$ complex thereof 21a. Insulin derivative according to paragraphs 20a, wherein $Q_1$ is an amino acid amide residue having from 4 to 10 carbon atoms.

22a. Insulin derivative according to any of paragraphs 20a-21a, wherein $Q_1$ is selected from the group consisting of β-D-Asp-amide, β-L-Asp-amide, γ-L-Glu-amide and γ-D-Glu-amide.

23a. Insulin derivative according to paragraphs 20a, wherein $Q_1$ is a chain of amino acid amide residues.

24a. Insulin derivative according to paragraphs 20a or 23a, wherein $Q_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide, 25a. Insulin derivative according to any of paragraphs 20a-24a, wherein $Q_2$ is a bond 26a. Insulin derivative according to any of paragraphs 21a-25a, wherein $X_1$ is —C=O 27a. Insulin derivative according to any of paragraphs 20a-26a, wherein $Q_2$ is selected from the group consisting of CO(CONH$_2$)CH—; —(CO—$(CH_2)_{2-6}$—NH—CO)$_{1-4}$—; —(CO—$(CH_2)_{2-6}$—CO—NH)$_{1-4}$—;

28a. Insulin derivative according to any of paragraphs 20a or 27a, wherein $Q_2$ is selected from the group consisting of —(CO—$(CH_2)_2$—NH—CO)$_1$—-(CO—$(CH_2)_3$—NH—CO)$_1$—, —(CO—$(CH_2)_4$—NH—CO)$_1$— or —(CO—$(CH_2)_5$—NH—CO)$_1$—.

29a. Insulin derivative according to paragraphs 27a or 28a, wherein $Q_1$ is a bond.

30a. Insulin derivative according to any of paragraphs 20a-29a, wherein $Q_3$ is —$(CH_2)_m$— where m is an integer in the range of 6 to 32 or from 8 to 20.

31a. Insulin derivative according to paragraphs 30a, where m is 12, 13, 14, 15 or 16.

32a. Insulin derivative according to any of paragraphs 20a-31a, wherein Z is —COOH.

33a. Insulin derivative according to any of paragraphs 20a-31a, wherein Z is —CH(COOH)$_2$.

34a. An insulin derivative according to any of paragraphs 20a-31a, wherein Z is —N(CH$_2$COOH)$_2$.

35a. An insulin derivative according to any of paragraphs 20a-31a, wherein Z is —SO$_3$H.

36a. An insulin derivative according to any of paragraphs 20a-31a, wherein Z is —PO$_3$H.

37a. Insulin derivative according to any of the preceeding paragraphs selected from the group consisting of $N^{\epsilon B29}$-ω-carboxy-pentadecanoyl-γ-L-glutamylamide desB30 human insulin, $N^{\epsilon B29}$-ω-carboxy-pentadecanoyl-γ-amino-butanoyl desB30 human insulin, $N^{\epsilon B29}$-ω-carboxy-tetradecanoyl-γ-L-glutamylamide desB30 human insulin, $N^{\epsilon B29}$-ω-carboxy-tridecanoyl-γ-L-glutamylamide desB30 human insulin, $N^{\epsilon B29}$-ω-carboxy-pentadecanoyl-β-alanyl desB30 human insulin, $N^{\epsilon B29}$-ω-carboxy-pentadecanoyl-γ-L-aspartylamide desB30 human insulin, $N^{\epsilon B29}$-ω-carboxy-pentadecanoyl-ε-aminohexanoyl desB30 human insulin, $N^{\epsilon B29}$-ω-carboxy-pentadecanoyl-δ-aminopentanoyl desB30 human insulin.

38a. Insulin derivative according to paragraphs 11a, wherein $Q_1$ is:
  an α-amino acid amide residue having a carboxylic acid group in the substituent which residue forms, with one of its carboxylic acid groups, an amide group together with the α-amino group of the N-terminal amino acid residue of the B chain or together with the ε-amino group of a Lys residue present in the B chain of the parent insulin;
  a chain composed of two, three or four α-amino acid amide residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral substituent and amino acid residues having a carboxylic acid group in the substituent so that W has at least one amino acid residue which has a carboxylic acid group in the substituent; or
  a bond $Q_2$ is:
  —COCH(CONH$_2$)—
  —COCH$_2$N(CH$_2$CONH$_2$)—
  —COCH$_2$N(CH$_2$CONH$_2$)COCH$_2$N(CH$_2$CONH$_2$)—
  —COCH$_2$CH$_2$N(CH$_2$CH$_2$CONH$_2$)—
  —COCH$_2$CH$_2$N(CH$_2$CH$_2$CONH$_2$)—COCH$_2$CH$_2$N(CH$_2$CH$_2$CONH$_2$)—
  —COCH$_2$N(CH$_2$CH$_2$CONH$_2$)—
  —COCH$_2$CH$_2$N(CH$_2$CONH$_2$)—
  —(CO—(CH$_2$)$_{2-6}$—NH—CO)$_{1-4}$—;
  —(CO—(CH$_2$)$_{2-6}$—CO—NH)$_{1-4}$—;
  —(CO—(CR$_9$R$_{10}$)$_{1-6}$—CO—NH)$_{1-4}$—, where R$_9$ and R$_{10}$, independently of each other can be H, —CH$_3$, —(CH$_2$)$_{1-6}$CH$_3$ or —CONH$_2$; or
  a bond
  provided that at least one of $Q_1$ or $Q_2$ is not a bond;

$Q_3$ is
  —((CR$_1$R$_2$)$_{1-6}$—NR$_{15}$—CO)$_{1-4}$—, where R$_1$, R$_2$ and R$_{15}$ independently of each other can be H, —CH$_3$, —CH$_{1-6}$ CH$_3$, —SO$_3$H, —(CH$_2$)$_{1-6}$—SO$_3$H, —(CH$_2$)$_{1-6}$—O—PO$_3$H$_2$ or CONH$_2$ and R$_{15}$ can be arylene which may be substituted with one or two groups of R$_1$, R$_2$ as defined above;
  NR$_{15}$ where R$_{15}$ is defined as above,
  a bond $Q_4$ is
  —(CH$_2$)$_m$— where m is an integer from 4 to 22;
  a divalent hydrocarbon chain comprising 1, 2 or 3 —CH=CH— groups and a number of —CH$_2$— groups sufficient to give a total number of carbon atoms in the chain in the range of 4 to 22;
  arylene or heteroarylene, which may be substituted with one or two groups selected from the group consisting of —COOH, —CH$_3$, —CH$_p$CH$_3$, —SO$_3$H, —(CH$_2$)$_p$—SO$_3$H, —CONR$_1$R$_2$ or —SO$_2$NR$_1$R$_2$, where R$_1$ and R$_2$, independently of each other can be H, —CH$_3$, —(CH)$_{1-6}$—CH$_3$, —SO$_3$H, —(CH$_2$)$_{1-6}$—SO$_3$H, —(CH$_2$)$_p$—O—PO$_3$H$_2$ or CONH$_2$; or
  a divalent hydrocarbon chain of the formula

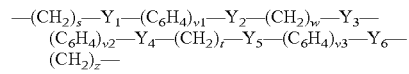

wherein Y$_1$-Y$_6$ independently of each other can be O; S or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other; or X$_1$ is O;
—C=O
a bond; or

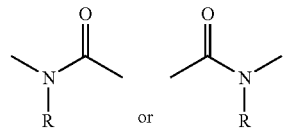

where R is hydrogen, $C_{1-3}$-alkyl, $C_{2-3}$-alkenyl or $C_{2-3}$-alkynyl; and X$_2$, X$_3$ and Q$_5$ are bonds;

All values of n are zero; and

Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—OSO$_3$H
—OPO3H$_2$
—PO$_3$H$_2$ or
-tetrazol-5-yl or
—O—W$_1$, where W$_1$ is arylene or heteroarylene, which may be substituted with one or two groups selected from the group consisting of —COOH, —SO$_3$H, —(CH$_2$)$_{1-6}$—SO$_3$H, —CONR$_{13}$R$_{14}$ or —SO$_2$NR$_{12}$R$_{14}$, where R$_{13}$ and R$_{14}$, independently of each other can be H, —SO$_3$H, —(CH$_2$)$_{1-6}$—SO$_3$H, —(CH$_2$)$_{1-6}$—O—PO$_3$H$_2$, —CONH$_2$ or tetrazo-5-lyl;

and any Zn$^{2+}$ complex thereof.

39a. Insulin derivative according to paragraphs 38a, wherein $Q_1$ is an amino acid amide residue having from 4 to 10 carbon atoms.

40a. Insulin derivative according to any of paragraphs 38a-39a, wherein $Q_1$ is selected from the group consisting of β-D-Asp-amide, β-L-Asp-amide, γ-L-Glu-amide and γ-D-Glu-amide.

41a. Insulin derivative according to paragraphs 38a, wherein $Q_1$ is a chain of amino acid amide residues.

42a. Insulin derivative according to paragraphs 38a or 41a, wherein $Q_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide, 43a Insulin derivative according to any of paragraphs 38a-42a, wherein $Q_2$ is a bond 44a. Insulin derivative according to any of paragraphs 38a-42a, wherein $Q_2$ is selected from the group consisting of $CO(CONH_2)CH-$; $-(CO-(CH_2)_{2-6}-NH-CO)_{1-4}-$ and $-(CO-(CH_2)_{2-6}-CO-NH)_{1-4}-$.

45a. Insulin derivative according to paragraphs 44a, wherein $Q_1$ is a bond.

46a. Insulin derivative according to any of paragraphs 38a, 44a or 45a, wherein $Q_2$ is selected from the group consisting of $-(CO-(CH_2)_2-NH-CO)_1-$ or $-(CO-(CH_2)_3-NH-CO)_{1-4}-$ 47a. Insulin derivative according to paragraphs 37a, wherein $Q_4$ is $-(CH_2)_s-Y_1-(C_6H_4)_{v1}-Y_2-(CH_2)_w-Y_3-(C_6H_4)_{v2}-Y_4-(CH_2)_t-Y_5-(C_6H_4)_{v3}-Y_6-(CH_2)_z-$
wherein $Y_1$-$Y_6$ independently of each other can be O; S or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other.

48a. Insulin derivative according to any of paragraphs 37a or 46a, wherein at least two of $v_1$, $v_2$, or $v_3$ are zero.

49a. Insulin derivative according to any of paragraphs 38a, 47a or 48a, wherein at $Y_1$—$Y_6$ are bonds.

50a. Insulin derivative according to any of paragraphs 38a, 47a or 48a, wherein at least one of $Y_1$-$Y_6$ are O or S.

51a. Insulin derivative according to any of paragraphs 38a or 47a-48a, wherein $Y_1$ is O or S and $v_1$ is one.

52a. Insulin derivative according to any of paragraphs 38a-51a, wherein Z is —COOH.

53a. Insulin derivative according to any of paragraphs 38a-51a, wherein Z is —CH(COOH)$_2$.

54a. An insulin derivative according to any of paragraphs 38a-51a, wherein Z is —N(CH$_2$COOH)$_2$.

55a. An insulin derivative according to any of paragraphs 38a-51a, wherein Z is —SO$_3$H.

56a. An insulin derivative according to any of paragraphs 38a-51a, wherein Z is —PO$_3$H.

57a. An insulin derivative according to any of paragraphs 38a-51a, wherein Z is —O—W$_1$,
where W$_1$ is arylene or heteroarylene, which may be substituted with one or two groups selected from the group consisting of —COOH, —SO$_3$H, —(CH$_2$)$_{1-6}$—SO$_3$H, —CONR$_{13}$R$_{14}$ or —SO$_2$NR$_{12}$R$_{14}$, where R$_{13}$ and R$_{14}$, independently of each other can be H, —SO$_3$H, —(CH$_2$)$_{1-6}$—SO$_3$H, —(CH$_2$)$_{1-6}$—O—PO$_3$H$_2$, —CONH$_2$ or tetrazo-5-lyl.

58a. Insulin derivative according to any of paragraphs 1a-19a or 38a-57a wherein the insulin derivative are selected from the group consisting of $N^{\epsilon B29}$-10-(4-carboxyphenoxy)-decanoyl-γ-L-glutamylamide desB30 human insulin, $N^{\epsilon B29}$-4-[11-(4-Carboxyphenyl)undecanoylamino]butyryl desB30 human insulin.

59a. Insulin derivative according to paragraphs 11a, wherein
$Q_1$ is:
an α-amino acid amide residue having a carboxylic acid group in the substituent which residue forms, with one of its carboxylic acid groups, an amide group together with the α-amino group of the N-terminal amino acid residue of the B chain or together with the ε-amino group of a Lys residue present in the B chain of the parent insulin;
a chain composed of two, three or four α-amino acid amide residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral substituent and amino acid residues having a carboxylic acid group in the substituent so that W has at least one amino acid residue which has a carboxylic acid group in the substituent; or
a bond $Q_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—(CO—(CH$_2$)$_{2-6}$—NH—CO)$_{1-4}$—;
—(CO—(CH$_2$)$_{2-6}$—CO—NH)$_{1-4}$—;
—(CO—(CR$_9$R$_{10}$)$_{1-6}$—CO—NH)$_{1-4}$—, where R$_9$ and R$_{10}$, independently of each other can be H, —CH$_3$, —(CH$_2$)$_{1-6}$CH$_3$ or —CONH$_2$; or
a bond
provided that at least one of $Q_1$ or $Q_2$ is not a bond;
n is independently 2 or 3;
$Q_3$, $Q_4$, and $Q_5$ independently of each other can be
(CH$_2$CH$_2$O)$_y$—; (CH$_2$CH$_2$CH$_2$O)$_y$—;
(CH$_2$CH$_2$CH$_2$CH$_2$O)$_y$—;
(CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—;
—(CH$_2$OCH$_2$)$_y$— where y is 1-20;
—(CH$_2$)$_m$— where m is an integer in the range of 1 to 32;
a divalent hydrocarbon chain comprising 1, 2 or 3 —CH=CH— groups and a number of —CH$_2$— groups sufficient to give a total number of carbon atoms in the chain in the range of 4 to 32;
—(CR$_3$R$_4$)$_{1-6}$—(NHCO—(CR$_3$R$_4$)$_{1-6}$—NHCO)$_{1-2}$—(CR$_3$R$_4$)$_{1-6}$ or —(CR$_3$R$_4$)$_{1-6}$—(CONH—(CR$_3$R$_4$)$_{1-6}$—CONH)$_{1-2}$—(CR$_3$R$_4$)$_{1-6}$—, —(CR$_3$R$_4$)$_{1-6}$—(NHCO—(CR$_3$R$_4$)$_{1-6}$—CONH)$_{1-2}$—(CR$_3$R$_4$)$_{1-6}$— or —(CR$_3$R$_4$)$_{1-6}$—(CONH—(CR$_3$R$_4$)$_{1-6}$—NHCO)$_{1-2}$—(CR$_3$R$_4$)$_{1-6}$ where R$_3$ and R$_4$ independently of each other and independently for each carbon can be H, —COOH or OH, —(CR₅R₆)₁₋₆—, where R₅ and R₆ independently of each other and independently for each carbon can be H, —COOH, (CH₂)₁₋₆COOH; or a bond;

with the proviso that $Q_3$-$Q_5$ are different;

$X_1$, $X_2$ and $X_3$ are independently

O;

—C=O;

a bond; or

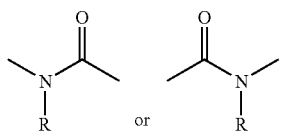

where R is hydrogen, $C_{1-3}$-alkyl, $C_{2-3}$-alkenyl or $C_{2-3}$-alkynyl; and Z is:

—COOH;
—CO-Asp;
—CO-Glu;
—CO-Gly;
—CO-Sar;
—CH(COOH)₂;
—N(CH₂COOH)₂;
—SO₃H
—OSO₃H
—OPO3H₂
—PO₃H₂ or
-tetrazol-5-yl and any $Zn^{2+}$ complex thereof.

60a. Insulin derivative according to paragraphs 59a, wherein $Q_1$ is an amino acid amide residue having from 4 to 10 carbon atoms.

61a. Insulin derivative according to any of paragraphs 59a-60a, wherein $Q_1$ is selected from the group consisting of β-D-Asp-amide, β-L-Asp-amide, γ-L-Glu-amide and γ-D-Glu-amide.

62a. Insulin derivative according to paragraphs 59a, wherein $Q_1$ is a chain of amino acid amide residues.

63a. Insulin derivative according to paragraphs 59a or 62a, wherein $Q_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide-γ-D-Glu-amide-γ-D-Glu-amide, γ-D-Glu-amide-β-D-Asp-amide, 64a. Insulin derivative according to any of paragraphs 59a-63a, wherein $Q_2$ is a bond 65a. Insulin derivative according to any of paragraphs 59a-63a, wherein $Q_2$ is selected from the group consisting of CO(CONH₂)CH—; —(CO—(CH₂)₂₋₆—NH—CO)₁₋₄—; —(CO—(CH₂)₂₋₆—CO—NH)₁₋₄—;

66a. Insulin derivative according to any of paragraphs 59a or 65a, wherein $Q_2$ is selected from the group consisting of —(CO—(CH₂)₂—NH—CO)₁— or —(CO—(CH₂)₃—NH—CO)₁₋₄—

67a. Insulin derivative according to paragraphs 65a or 66a, wherein $Q_1$ is a bond.

68a. Insulin derivative according any of paragraphs 59a-67a, wherein one of $Q_3$, $Q_4$, or $Q_5$ is —(CH₂)ₘ— where m is an integer in the range of 1 to 32 or 1-12.

69a. Insulin derivative according to any of paragraphs 59a-67a, wherein one of $Q_3$, $Q_4$, or $Q_5$ is (CH₂CH₂O)ᵧ—; (CH₂CH₂CH₂O)ᵧ—; (CH₂CH₂CH₂CH₂O)ᵧ—; (CH₂CH₂OCH₂CH₂CH₂CH₂O)ᵧ— or (CH₂CH₂CH₂OCH₂CH₂CH₂CH₂O)ᵧ—; —(CH₂OCH₂)ᵧ— where y is 1-20;

70a. Insulin derivative according to paragraphs 69a, wherein one of $Q_3$, $Q_4$, or $Q_5$ is (CH₂CH₂O)ᵧ— or (CH₂CH₂OCH₂CH₂CH₂CH₂O) wherein y is in the range of 2-12, 2-4 or 2-3

71a. Insulin derivative according to any of paragraphs 59a, 69a or 70a, wherein y is 1.

72a. Insulin derivative according to any of paragraphs 59a-71a, wherein Z is —COOH.

73a. Insulin derivative according to any of paragraphs 59a-71a, wherein Z is —CH(COOH)₂.

74a. An insulin derivative according to any of paragraphs 59a-71a, wherein Z is —N(CH₂COOH)₂.

75a. An insulin derivative according to any of paragraphs 59a-71a, wherein Z is —SO₃H.

76a. An insulin derivative according to any of paragraphs 59a-71a, wherein Z is —PO₃H.

77a. Insulin derivative according to any of paragraphs 1a-19a or 59a-76a selected from the group consisting of $N^{\epsilon B29}$-(3-(3-{4-[3-(7-carboxyheptanoylamino)propoxy]butoxy}propylcarbamoyl)-propionyl-γ-glutamylamide) desB30 human Insulin 78a. Insulin derivative according to any of the paragraphs 1a-77a, wherein the parent insulin is human insulin or porcine insulin 79a Insulin derivative according to any of the paragraphs 1a77a, wherein the parent insulin is an insulin analogue.

80a. Insulin derivative according to any of paragraphs 78a-79a, wherein the amino acid residue at position B30 of the parent insulin is Lys or has been deleted.

81a. Insulin derivative according to paragraphs 80a, wherein the parent insulin is desB30 human insulin.

82a. Insulin derivative according to any of paragraphs 78a-81a, wherein the amino acid residue at position B1 of the parent insulin has been deleted.

83a. Insulin derivative according to any of paragraphs 78a-82a, wherein the amino acid residue in position A21 of the parent insulin is Gly or Asn.

84a. Insulin derivative according to any of paragraphs 78a-83a, wherein the amino acid residue at position B3 of the parent insulin is Lys 85a. Insulin derivative according to any of paragraphs 78a-84a, wherein the amino acid residue at position B28 of the parent insulin is Asp or Lys.

86a. Insulin derivative according to any of paragraphs 78a-85a, wherein the amino acid residue at position B29 of the parent insulin is Pro or Thr.

87a. Insulin derivative according to paragraphs 85a, wherein the parent insulin is AspB28 human insulin 88a. Insulin derivative according to paragraphs 83a, wherein the parent insulin is GlyA21 human insulin or GlyA21desB30 human insulin or GlyA21ArgB31ArgB32 human insulin.

89a. Insulin derivative according to paragraphs 84a, wherein the parent insulin is LysB3GluB29 human insulin.

90a. Insulin derivative according to paragraphs 85a-86a, wherein the parent insulin is LysB28ProB29 human insulin 91a. Insulin derivative according to paragraphs 80a and 86a, wherein the parent insulin is ThrB29LysB30 human insulin 92a. A zinc complex of an insulin derivative according to any of the preceding paragraphs wherein each insulin hexamer binds two zinc ions, three zinc ions or four zinc ions.

93a. A pharmaceutical composition for the treatment of diabetes in a patient in need of such treatment, comprising a therapeutically effective amount of an insulin derivative according to any of the preceding paragraphs together with a pharmaceutically acceptable carrier.

94a. A pharmaceutical composition for the treatment of diabetes in a patient in need of such treatment, comprising a therapeutically effective amount of an insulin derivative according to any of the preceding paragraphs in mixture with an insulin or an insulin analogue which has a rapid onset of action, together with a pharmaceutically acceptable carrier.

95a. A method of treating diabetes in a patient in need of such a treatment, comprising administering to the patient a therapeutically effective amount of an insulin derivative according to paragraphs 1a-94a together with a pharmaceutically acceptable carrier.

94a. A method of treating diabetes in a patient in need of such a treatment, comprising administering to the patient a therapeutically effective amount of an insulin derivative according to paragraphs 1a-94a in mixture with an insulin or an insulin analogue which has a rapid onset of action, together with a pharmaceutically acceptable carrier.

97a. A method according to paragraphs 95a or 96a for pulmonary treatment of diabetes 98a. A mixture of an insulin derivative according to any of paragraphs 1a-92a and a rapid acting insulin analogue selected group consisting of AspB28 human insulin; LysB28ProB29 human insulin and LysB3GluB29 human insulin.

99a. Insulin derivative as described in the examples.

The starting product for the acylation, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent insulin may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J.

Fritsch, E F and Maniatis, T. *Molecular Cloning: A Laboratory Manual*, Cold Spring Harbor Laboratory Press, New York, 1989). The DNA sequence encoding the parent insulin may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is for example an expression vector in which the DNA sequence encoding the parent insulin is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the parent insulin in a variety of host cells are well known in the art, cf. for instance Sambrook et al., supra.

The DNA sequence encoding the parent insulin may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the parent insulin, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The parent insulin molecule is then converted into the insulin derivatives of the invention by introducing of the relevant substituent in either the B1 position or in the chosen Lys position in the B-chain. The substituent can be introduced by any convenient method and many methods are disclosed in the prior art for acylation of an amino group. More details will appear from the following examples.

Insulin derivatives according to the invention may be provided in the form of essentially zinc free compounds or in the form of zinc complexes. When zinc complexes of an insulin derivative according to the invention are provided, two $Zn^{2+}$ ions, three $Zn^{2+}$ ions, four $Zn^{2+}$ ions, five $Zn^{2+}$ ions, six $Zn^{2+}$ ions, seven $Zn^{2+}$ ions, eight $Zn^{2+}$ ions, nine $Zn^{2+}$ ions or ten $Zn^{2+}$ ions can be bound per six molecules of insulin derivative. Solutions of zinc complexes of the insulin derivatives will contain mixtures of such species.

In one aspect the invention is related to a pharmaceutical composition comprising a therapeutically effective amount of an insulin derivative or a zinc complex of the insulin derivative according to the invention optionally together with a pharmaceutically acceptable carrier and/or a pharmaceutically acceptable additive, which composition can be provided for the treatment of type 1 diabetes, type 2 diabetes and other states that cause hyperglycaemia in patients in need of such a treatment.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising the insulin derivative or a zinc complex of the insulin derivative according to the invention optionally together with a pharmaceutically acceptable carrier and/or pharmaceutical acceptable additives.

In one aspect of the invention, there is provided a method for the manufacture of a pharmaceutical composition for the use in the treatment of type 1 diabetes, type 2 diabetes and other states that cause hyperglycaemia, the composition comprising an insulin derivative or a zinc complex of the insulin derivative according to the invention optionally together with a pharmaceutically acceptable carrier and/or pharmaceutical acceptable additives.

In one aspect of the invention, there is provided a pharmaceutical composition for treating type 1 diabetes, type 2 diabetes and other states that cause hyperglycaemia in a patient in need of such a treatment, the composition comprising a therapeutically effective amount of an insulin derivative or a zinc complex of the insulin derivative according to the invention in mixture with an insulin or an insulin analogue which has a rapid onset of action, optionally together with pharmaceutically acceptable carriers and/or additives.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising the insulin derivative or a zinc complex of the insulin derivative according to the invention in mixture with an insulin or an insulin analogue which has a rapid onset of action, optionally together with a pharmaceutically acceptable carrier and/or pharmaceutical acceptable additives.

In one aspect of the invention, there is provided a method for the manufacture of a pharmaceutical composition for the use in the treatment of type 1 diabetes, type 2 diabetes and other states that cause hyperglycaemia, the composition comprising a therapeutically effective amount of an insulin derivative or a zinc complex of the insulin derivative according to the invention in mixture with an insulin or an insulin analogue which has a rapid onset of action, optionally together with a pharmaceutically acceptable carrier and/or pharmaceutical acceptable additives.

In one aspect the invention provides a pharmaceutical composition being a mixture of an insulin derivative or a zinc complex of the insulin derivative according to the invention and a rapid acting insulin analogue selected group consisting of AspB28 human insulin; LysB28ProB29 human insulin and LysB3GluB29 human insulin.

One aspect of the invention is related to a pharmaceutical composition comprising a therapeutically effective amount of an insulin derivative or a zinc complex of the insulin derivative according to the invention optionally together with a pharmaceutically acceptable carrier and/or a pharmaceutically acceptable additive, which can be provided for pulmonary treatment of type 1 diabetes, type 2 diabetes and other states that cause hyperglycaemia in patients in need of such a treatment.

In one aspect the invention is related to application of a pharmaceutical composition for pulmonary treatment of type 1 diabetes, type 2 diabetes and other states that cause hyperglycaemia in a patient in need of such a treatment, the pharmaceutical composition comprising a therapeutically effective amount of an insulin derivative or a zinc complex of the insulin derivative according to the invention optionally in mixture with an insulin or an insulin analogue which has a rapid onset of action, and optionally together with pharmaceutically acceptable carriers and/or additives.

In one aspect of the invention, there is provided a method for the manufacture of a pharmaceutical composition for the use in the treatment of type 1 diabetes, type 2 diabetes and other states that cause hyperglycaemia, the composition being used pulmonary and comprising a therapeutically effective amount of an insulin derivative or a zinc complex of the insulin derivative according to the invention optionally in mixture with an insulin or an insulin analogue which has a rapid onset of action, and optionally together with a pharmaceutically acceptable carrier and/or pharmaceutical acceptable additives.

The insulin derivative according to the invention and the rapid acting insulin analogue can be mixed in a ratio from about 90/10%; about 70/30% or about 50/50%.

In one aspect, the invention relates to a pharmaceutical composition comprising an insulin derivative according to the invention which is soluble at physiological pH values.

In one aspect, the invention relates to a pharmaceutical composition comprising an insulin derivative according to the invention which is soluble at pH values in the interval from about 6.5 to about 8.5.

In one aspect, the invention relates to a pharmaceutical composition with a prolonged profile of action which comprises an insulin derivative according to the invention.

In one aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

Pharmaceutical Compositions

The insulin derivatives of this invention of the claimed formula can, for example, be administered subcutaneously, orally, or pulmonary.

For subcutaneous administration, the compounds of the formula are formulated analogously with the formulation of known insulins. Furthermore, for subcutaneous administration, the compounds of the formula are administered analogously with the administration of known insulins and, generally, the physicians are familiar with this procedure.

The insulin derivatives of this invention may be administered by inhalation in a dose effective manner to increase circulating insulin levels and/or to lower circulating glucose levels. Such administration can be effective for treating disorders such as diabetes or hyperglycemia. Achieving effective doses of insulin requires administration of an inhaled dose of insulin derivative of this invention of more than about 0.5 µg/kg to about 50 µg/kg. A therapeutically effective amount can be determined by a knowledgeable practitioner, who will take into account factors including insulin level, blood glucose levels, the physical condition of the patient, the patient's pulmonary status, or the like.

Administration by inhalation can result in pharmacokinetics comparable to subcutaneous administration of insulins. Different inhalation devices typically provide similar pharmacokinetics when similar particle sizes and similar levels of lung deposition are compared.

According to the invention, insulin derivative of this invention may be delivered by any of a variety of inhalation devices known in the art for administration of a therapeutic agent by inhalation. These devices include metered dose inhalers, nebulizers, dry powder generators, sprayers, and the like. Insulin derivative of this invention is delivered by a dry powder inhaler or a sprayer. There are a several desirable features of an inhalation device for administering insulin derivative of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of insulin derivative of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and into the lower airways or alveoli. The insulin derivative of this invention can be formulated so that at least about 10% of the insulin conjugate delivered is deposited in the lung, for example about 10 to about 20%, or more. It is known that the maximum efficiency of pulmonary deposition for mouth breathing humans is obtained with particle sizes of about 2 µm to about 3 µm. When particle sizes are above about 5 µm pulmonary deposition decreases substantially. Particle sizes below about 1 µm cause pulmonary deposition to decrease, and it becomes difficult to deliver particles with sufficient mass to be therapeutically effective. Thus, particles of the insulin derivative delivered by inhalation have a particle size less than about 10 µm, for example in the range of about 1 µm to about 5 µm. The formulation of the insulin derivative is selected to yield the desired particle size in the chosen inhalation device.

Advantageously for administration as a dry powder, an insulin derivative of this invention is prepared in a particulate form with a particle size of less than about 10 µm, for example about 1 to about 5 µm. The particle size is effective for delivery to the alveoli of the patient's lung. The dry powder is largely composed of particles produced so that a majority of the particles have a size in the desired range. Advantageously, at least about 50% of the dry powder is made of particles having a diameter less than about 10 µm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of insulin derivatives of this invention for administration from a dry powder inhaler typically include a finely divided dry powder containing the derivative, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The insulin derivative can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the insulin derivatives of this invention can be produced by forcing a suspension or solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 μm, for example in the range of about 1 μm to about 5 μm.

Formulations of insulin derivatives of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, for example zinc. The formulation can also include an excipient or agent for stabilization of the insulin derivative, such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The insulin derivative formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an insulin derivative according to the present invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, for example in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy*, $19^{th}$ edition, 1995.

In a further aspect of the invention the formulation further comprises an isotonic agent which may be selected from the group consisting of a salt (e.g. sodium chloride), a sugar or sugar alcohol, an amino acid (e.g. glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one—OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy*, $19^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulin derivatives of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

The present invention is further illustrated by the following examples which, however, are not to be construed as limiting the scope of protection.

DESCRIPTION OF DRAWINGS

FIG. 1: Size-exclusion chromatography of the insulin derivative in example 2 in mixture with insulin aspart (B28Asp human insulin). Insulin content in each individual peak is quantified by HLPC. The insulin derivative and Aspart in formulations with either 2.1 Zn(II) per hexamer or 6 Zn(II) per hexamer elutes as two separate fractions (high-molecular weight insulin and medium molecular weight insulin, respectively). The SEC experiments are performed in accordance with example 20.

FIG. 2: Clamp action profile after subcutaneous injection of the insulin derivative described in example 2 in different concentrations and with different Zn(II) concentrations demonstrating that the action profile of the insulin derivative is similar whether the insulin derivative is administered with 2.3 or 6 Zn(II) per six insulin or as 600 μM or 1200 μM formulations. The clamp experiment is performed in accordance with example 21.

EXAMPLES

Example 1

Figure 3:
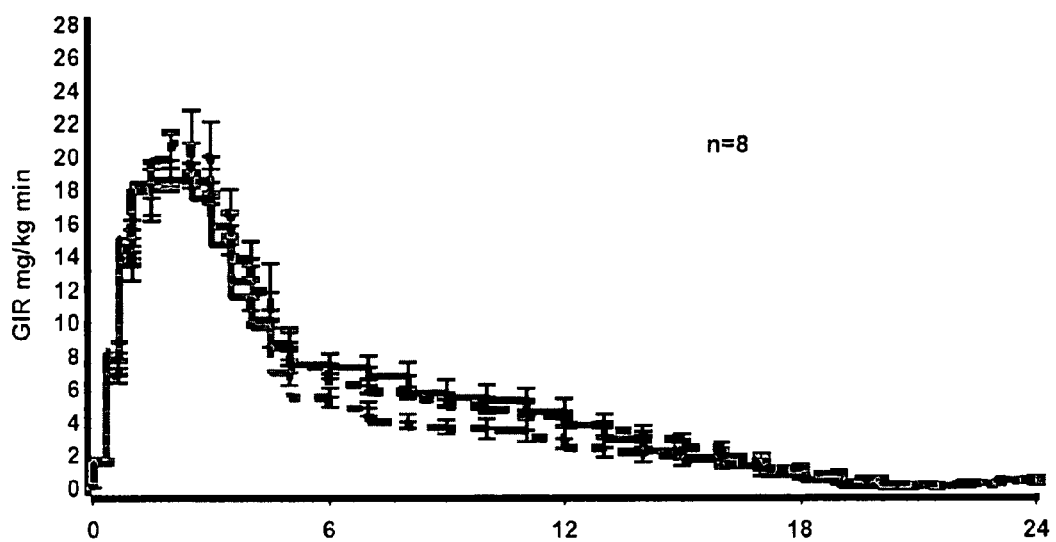
FIG. 3: Clamp action profile after subcutaneous injection of the insulin derivative described in example 2 in mixture with insulin Aspart, or as individual injections, demonstrating that there is no significant blunting of the individual insulin action profiles. The clamp experiment is performed in accordance with example 21.

Synthesis of $N^{\epsilon B29}$-ω-carboxy-pentadecanoyl-γ-L-glutamylamide desB30 human insulin

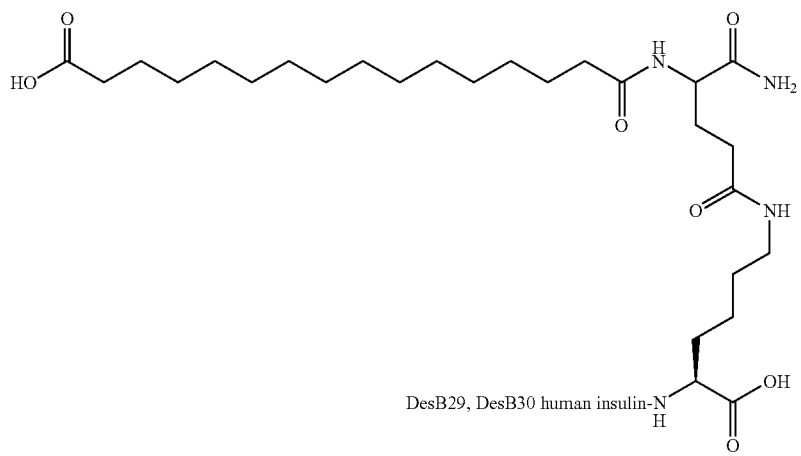

Step 1: Mono-tert-butyl hexadecandioate

Hexadecadioic acid (40.0 g, 140 mmol) was suspended in toluene (250 ml) and the mixture was heated to reflux. N,N-dimethylformamide di-tert-butyl acetal (76.3 g, 375 mmol) was added drop-wise over 4 hours. The mixture was refluxed overnight. The solvent was removed in vacuo at 50° C., and the crude material was suspended in DCM/AcOEt (500 ml, 1:1) and stirred for 15 mins. The solids were collected by filtration and triturated with DCM (200 ml). The filtrated were evaporated in vacuo to give crude mono-tert-butyl hexadecandioate, 30 grams. This material was suspended in DCM (50 ml), cooled with ice for 10 mins, and filtered. The solvent was removed in vacuo to leave 25 gram crude mono-tert-butyl hexadecandioate, which was recrystallized from heptane (200 ml) to give mono-tert-butyl hexadecandioate, 15.9 g (33%).

$^1$H-NMR (CDCl$_3$) δ: 2.35 (t, 2H), 2.20 (t, 2H), 1.65-1.55 (m, 4H), 1.44 (s, 9H), 1.34-1.20 (m, 20H).

Step 2: Succinimidyl tert-butyl hexadecandioate

The mono tert-butyl ester (2 g, 5.8 mmol) was dissolved in THF (20 ml) and treated with TSTU (2.1 g, 7.0 mmol) and DIEA (1.2 ml, 7.0 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave succinimidyl tert-butyl hexadecandioate, 2.02 g (79%).

$^1$H-NMR (CDCl$_3$) δ: 2.84 (s, 4H), 2.60 (t, 2H), 2.20 (t, 2H), 1.74 (p, 2H), 1.56 (m, 2H), 1.44 (s, 9H), 1.40 (m, 2H), 1.30-1.20 (m, 18H).

Step 3: ω-tert-butyl-carboxy-pentadecanoyl-L-glutamylamide

Succinimidyl tert-butyl hexadecandioate (100 mg, 0.227 mmol) was dissolved in DMF (2 ml) and treated with L-glutamylamide (37 mg, 0.25 mmol) and DIEA (58 µl, 0.34 mmol) and the mixture was stirred overnight. The solvent was evaporated in vacuo, and the crude product was dissolved in AcOEt, and washed twice with 0.2M HCl, with water and brine. Drying over MgSO$_4$ and evaporation in vacuo gave ω-tert-butyl-carboxy-pentadecanoyl-L-glutamyl amide, 85 mg (80%).

$^1$H-NMR (CDCl$_3$) δ: 6.98 (s, 1H), 6.60 (d, 1H), 5.88 (s, 1H), 4.69 (m, 1H), 2.55-2.41 (m, 2H), 2.25-2.18 (m, 2H), 2.14 (m, 1H), 1.93 (m, 1H), 1.65-1.54 (m, 4H) 1.44 (s, 9H), 1.27 (br, 20H).

Step 4: ω-tert-butyl-carboxy-pentadecanoyl-L-glutamylamide γ-succinimidyl ester ω-tert-butyl-carboxy-pentadecanoyl-L-glutamylamide (85 g, 0.181 mmol) was dissolved in THF (1 ml) and treated with TSTU (65 g, 0.217 mmol) and DIEA (37 µl, 0.217 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave ω-tert-butyl-carboxy-pentadecanoyl-L-glutamyl amide γ-succinimidyl ester, 91 mg (89%).

$^1$H-NMR (CDCl$_3$) δ: 6.59 (s, 1H), 6.41 (d, 1H), 5.56 (s, 1H), 4.62 (m, 1H), 3.02-2.94 (dd, 2H), 2.84 (s, 4H), 2.71-2.58 (m, 2H), 1.76 (m, 1H), 1.53-1.63 (m, 4H), 1.44 (s, 9H), 1.25 (br, 20H).

Step 5: N$^{εB29}$-ω-carboxy-pentadecanoyl-γ-L-glutamylamide desB30 human insulin DesB30 human insulin (500 mg, 0.088 mmol) was dissolved in 100 mM Na$_2$CO$_3$ (5 ml, pH 10.2) at room temperature. ω-Tert-butyl-carboxy-pentadecanoyl-L-glutamyl amide γ-succinimidyl ester (57 mg, 0.105 mmol), was dissolved in acetonitrile (5 ml) and subsequently added to the insulin solution. After 30 mins, 0.2 M methylamine (0.5 ml) was added. pH was adjusted by HCl to 5.5, and the isoelectric precipitate was collected by centrifugation and dried in vacuo to give 423 mg. The coupling yield was 42% (RP-HPLC, C4 column; Buffer A: 10% MeCN in 0.1% TFA-water, Buffer B: 80% MeCN in 0.1% TFA-water; gradient 20% to 90% B in 16 minutes). The protected product was dissolved in 95% TFA (12 ml), left 30 mins, and evaporated in vacuo. The crude product was dissolved in water and lyophilized.

N$^{εB29}$-ω-carboxy-pentadecanoyl-γ-L-glutamylamide desB30 human insulin was purified by RP-HPLC on C4-column, buffer A: 20% EtOH+0.1% TFA, buffer B: 80% EtOH+0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 50 mg, 12%. The purity as evaluated by HPLC was >98%. LCMS 6102.8; C$_{274}$H$_{412}$N$_{66}$O$_{80}$S$_6$ requires 6103.1.

Example 2

Synthesis of N$^{εB29}$-ω-carboxy-pentadecanoyl-γ-amino-butanoyl desB30 human insulin

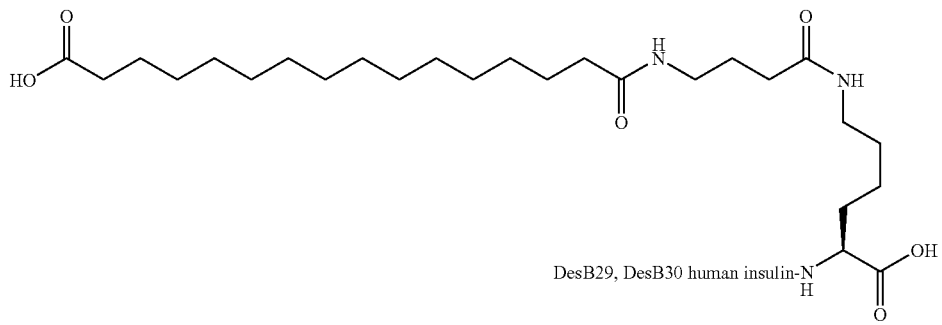

This compound was prepared from hexadecandioic acid and γ-aminobutyric acid, in analogy with example 1.

ω-tert-butyl-carboxy-pentadecanoyl-γ-amino-butyric acid succinimidyl ester $^1$H-NMR (CDCl$_3$) δ: 5.80 (m, 1H), 3.36 (dd, 2H), 2.84 (s, 4H), 2.65 (t, 2H), 2.21-2.13 (m, 4H), 1.99 (p, 2H), 1.44 (s, 9H), 1.66-1.51 (m, 6H), 1.25 (br, 20H).

N$^{εB29}$-ω-carboxy-pentadecanoyl-γ-amino-butanoyl desB30 human insulin

LCMS 6059.9; C$_{273}$H$_{411}$N$_{65}$O$_{79}$S$_6$ requires 6060.1.

Example 3

Synthesis of $N^{\epsilon B29}$-ω-carboxy-tetradecanoyl-γ-L-glutamylamide desB30 human insulin

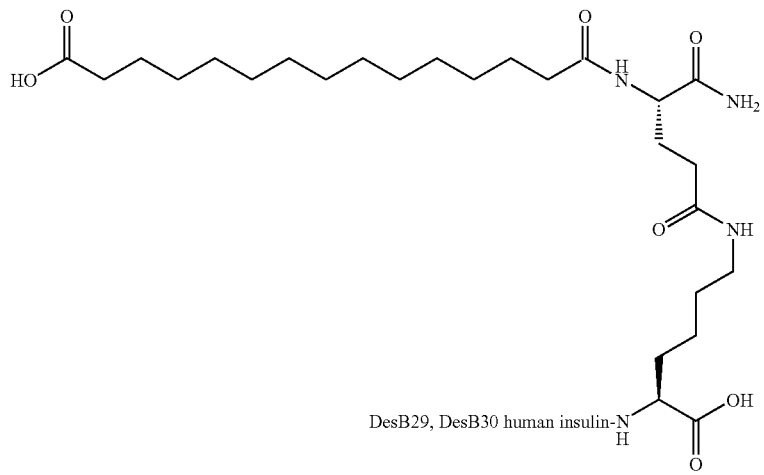

This compound was prepared from pentadecandioic acid and L-glutamylamide in analogy with example 1.

LCMS 6088.2; $C_{273}H_{410}N_{66}O_{80}S_6$ requires 6089.1.

Example 4

Synthesis of $N^{\epsilon B29}$-ω-carboxy-tridecanoyl-γ-L-glutamylamide desB30 human insulin

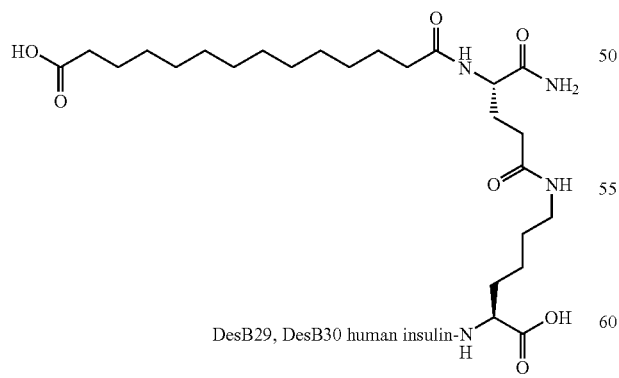

This compound was prepared from tetradecandioic acid and L-glutamylamide in analogy with example 1.

LCMS 6075.3; $C_{272}H_{408}N_{66}O_{80}S_6$ requires 6075.1.

Example 5

Synthesis of $N^{\epsilon B29}$-ω-carboxy-pentadecanoyl-β-alanyl desB30 human insulin

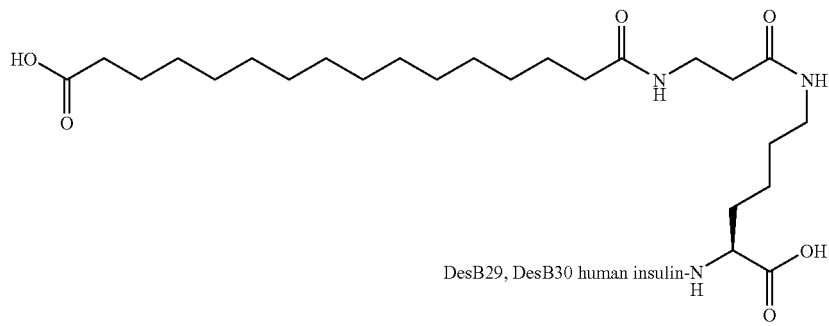

This compound was prepared from hexadecandioic acid and β-alanine in analogy with example 1.

LCMS 6044.8; $C_{272}H_{409}N_{65}O_{79}S_6$ requires 6046.1.

Example 6

Synthesis of $N^{\epsilon B29}$-ω-carboxy-pentadecanoyl-γ-L-aspartylamide desB30 human insulin

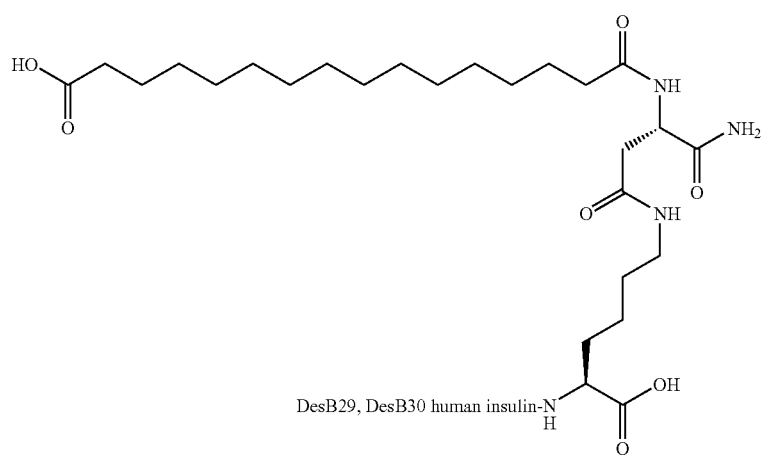

This compound was prepared from hexadecandioic acid and L-aspartylamide in analogy with example 1.

LCMS 6088.8; $C_{273}H_{410}N_{66}O_{80}S_6$ requires 6089.1.

Example 7

Synthesis of $N^{\epsilon B29}$-ω-carboxy-pentadecanoyl-ε-aminohexanoyl desB30 human insulin

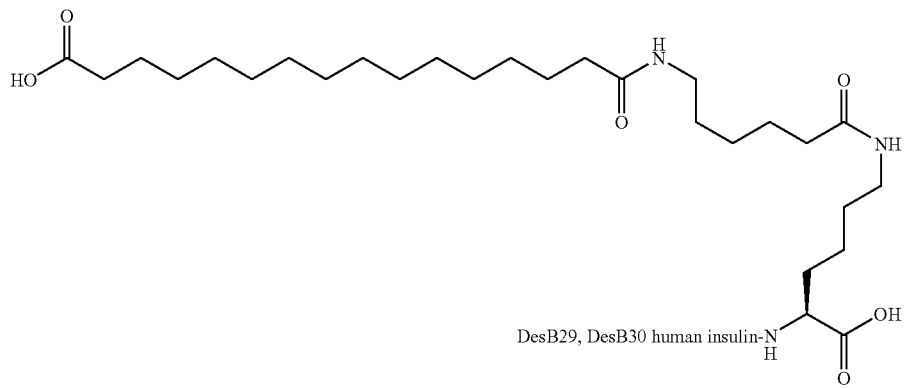

This compound was prepared from hexadecandioic acid and ε-amino-hexanoic acid in analogy with example 1.
LCMS 6086.1; $C_{275}H_{415}N_{65}O_{79}S_6$ requires 6088.1.

Example 8

Synthesis of $N^{\epsilon B29}$-ω-carboxy-pentadecanoyl-δ-aminopentanoyl desB30 human insulin

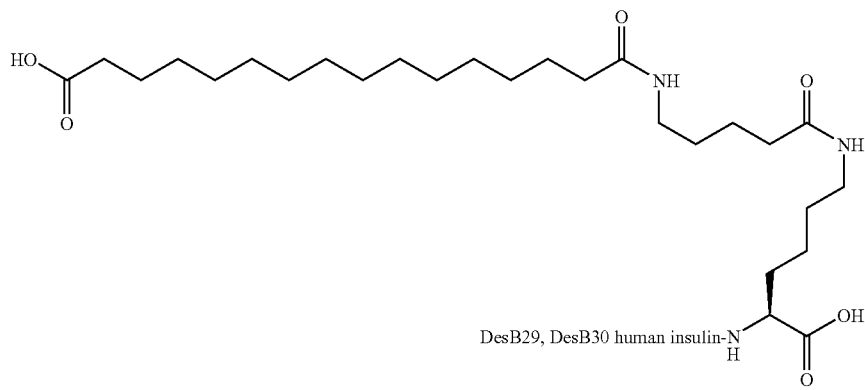

This compound was prepared from hexadecandioic acid and δ-amino-pentanoic acid in analogy with example 1.
LCMS 6074.2, $C_{274}H_{413}N_{65}O_{79}S_6$ requires 6074.1.

Example 9

Synthesis of N$^{\epsilon B29}$-10-(4-carboxyphenoxy)-decanoyl-γ-L-glutamylamide desB30 human insulin

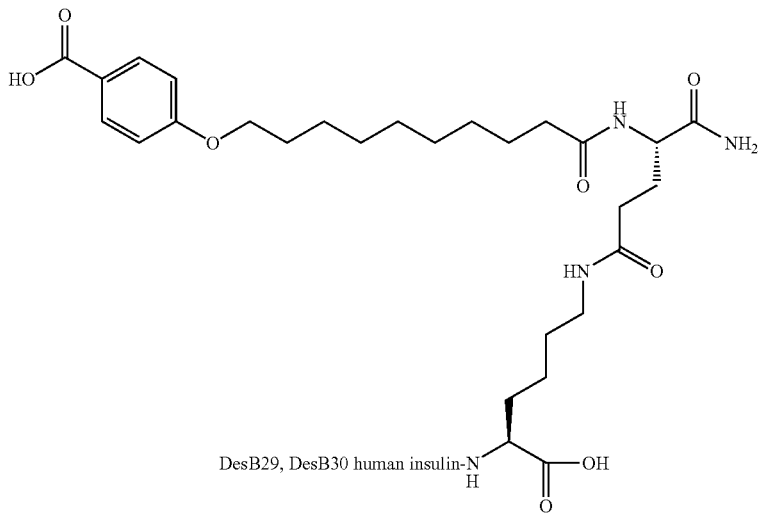

Step 1: 4-Hydroxy-benzoic acid tert-butyl ester

4-Hydroxy-benzoic acid (3 g, 21.7 mmol) was stirred in toluene (35 ml, dried over mol. sieves). The solution was heated to 80° C. under N$_2$, and N,N'-dimethylformamide di-tert-butyl acetal (10.42 mL, 43.4 mmol) was added over ca. 5 min. The mixture was stirred at 80° C. for 1 h 10 min., and cooled to rt. The solution was washed with water, twice with sat. NaHCO$_3$ and sat. NaCl (15 mL each), dried over MgSO$_4$, and concentrated to yield a yellow oil (2.77 g). The product was purified by flash chromatography (380 g silica, eluant: 4:6 AcOEt/heptane (2 L) and 1:1 AcOEt/heptane 700 mL) to yield white crystals (2.07 g, 49% yield).

HPLC-MS m/z: 217 (M+23).
$^1$H-NMR (CDCl$_3$, 400 MHz) 7.90 (d, 2H), 6.85 (d, 2H), 6.10 (s, 1H), 1.59 (s, 9H).

Step 2: 4-(9-Methoxycarbonylnonyloxy)benzoic acid tert-butyl ester

4-Hydroxy-benzoic acid tert-butyl ester (500 mg, 2.57 mmol) and 10-bromodecanoic acid methyl ester (683 mg, 2.57 mmol) were dissolved in acetonitrile, and K$_2$CO$_3$ (712 mg, 5.15 mmol) was added. The mixture was refluxed under nitrogen for 16 h, and cooled to rt. The solids were filtered off, and the filtrate concentrated under vacuum. The resulting residue was dissolved in AcOEt (50 ml) and water (25 mL). The phases were separated and the organic phase was dried over MgSO$_4$ and concentrated to yield a colorless oil (874 mg, 90% yield).

HPLC-MS m/z: 402 (M+23).
$^1$H-NMR (CDCl$_3$, 400 MHz) 7.92 (d, 2H), 6.87 (d, 2H), 3.99 (t, 2H), 3.67 (s, 3H), 2.31 (t, 2H), 1.72-1.83 (m, 2H), 1.59-1.69 (m, 2H), 1.58 (s, 9H), 1.40-1.50 (m, 2H), 1.23-1.40 (br, 8H).

Step 3: 4-(9-Carboxynonyloxy)benzoic acid tert-butyl ester 4-(9-Methoxycarbonylnonyloxy)benzoic acid tert-butyl ester (858 mg, 2.27 mmol) was dissolved in THF (5 ml), and 1N NaOH (2.27 mmol) was added. The mixture was stirred for 16 h. AcOEt (40 mL) and 1N HCl (2.38 ml) in water (25 ml) were added. The phases were separated, and the organic phase was dried over MgSO$_4$, and concentrated under vacuum to yield a white solid (781 mg, 95% yield).

HPLC-MS m/z: 387 (M+23).
$^1$H-NMR (CDCl$_3$, 400 MHz) 7.92 (d, 2H), 6.87 (d, 2H), 3.99 (t, 2H), 2.35 (t, 2H), 1.73-1.84 (m, 2H), 1.60-1.69 (m, 2H), 1.58 (s, 9H), 1.39-1.51 (m, 2H), 1.24-1.39 (br, 8H).

Step 4: 4-[9-(2,5-Dioxopyrrolidin-1-yloxycarbonyl)nonyloxy]benzoic acid tert-butyl ester 4-(9-Carboxynonyloxy)benzoic acid tert-butyl ester (779 mg, 2.14 mmol) was dissolved in THF (15 mL), and DIEA (366 µl, 2.14 mmol) was added. The mixture was cooled to 0° C., and placed under nitrogen, and HSTU was added. The mixture was stirred at 0° C. for 30 min and at RT for 16 h. The sample was concentrated under vacuum and AcOEt (40 ml) was added. The mixture was washed with 0.2 N HCl (2×25 ml), dried over MgSO$_4$, and concentrated under vacuum to yield a slightly yellow solid. The solid was recrystallized from AcOEt to yield a white powder (276 mg, 28% yield). The mother liquor was concentrated to yield crystalline residue (430 mg, 43% yield). Data for the white powder:

HPLC-MS m/z: 484 (M+23).
$^1$H-NMR (CDCl$_3$, 300 MHz) 7.93 (d, 2H), 6.88 (d, 2H), 3.99 (t, 2H), 2.83 (s, 4H), 2.61 (t, 2H), 1.67-1.88 (m, 4H), 1.58 (s, 11H, theoret. 9H+ water), 1.27-1.52 (m, 10H).

Step 5: 4-[9-((S)-1-Carbamoyl-3-carboxypropylcarbamoyl)nonyloxy]benzoic acid tert-butyl ester 4-[9-(2,5-Dioxopyrrolidin-1-yloxycarbonyl)nonyloxy]benzoic acid tert-butyl ester (200 mg, 0.433 mmol) was stirred in DMF (2 mL) and H-Glu-NH$_2$ (63 mg) was added. The non-homogeneous mixture was stirred at rt for 16 h. LC/MS analysis indicated the reaction had not gone to completion. H-Glu-NH$_2$ (20 mg) and more DMF (2 mL) were added and the mixture was stirred for 2 d at rt. The sample was concentrated under vacuum and AcOEt (50 mL) was added. The solution was washed with 0.2 N HCl (2×25 mL) and water (25 mL), dried over MgSO$_4$, and concentrated under vacuum to yield a white solid (180 mg, 86% yield).

HPLC-MS m/z: 493 (M+1).

Step 6: 4-{9-[(S)-1-Carbamoyl-3-(2,5-dioxopyrrolidin-1-yloxycarbonyl)propylcarbamoyl]nonyloxy}benzoic acid tert-butyl ester The HSTU activation was performed in manner similar to that described for 4-[9-(2,5-Dioxopyrrolidin-1-yloxycarbonyl)nonyloxy]benzoic acid tert-butyl ester. The product was purified by flash chromatography (1:1 AcOEt:heptane and AcOEt) to yield 18 mg.
HPLC-MS m/z: 590 (M+1).

Step 7: $N^{\epsilon B29}$-10-(4-carboxyphenoxy)decanoyl-γ-L-glutamylamide desB30 insulin DesB30 insulin (126 mg, 0.022 mmol) was dissolved by adding 100 mM $Na_2CO_3$ (1.5 mL) and acetonitrile (1.5 mL) in a 10 ml round bottom-flask. 4-{9-[(S)-1-Carbamoyl-3-(2,5-dioxopyrrolidin-1-yloxycarbonyl)propylcarbamoyl]nonyloxy}benzoic acid tert-butyl ester (14 mg, 0.022 mmol) was added in acetonitrile (750 uL) and $Na_2CO_3$ (750 uL) was added so the final solution was 50:50 100 mM $Na_2CO_3$/acetonitrile. The solution was stirred at RT for 1 h. The solution was transferred to a 15 ml centrifuge tube, washing with Milli-Q water (6 ml). The solution was cooled on ice, and the pH was adjusted to 5.1 by adding 1N HCl, which lead to precipitation. The tube was centrifuged at 5000 rpm for 10 min at 10° C. The solvent was decanted from the solid. 95:5 TFA/water (2.5 ml) was added to the solid. The solution was poured into a round bottom flask, washing with more 95:5 TFA/water (2.5 ml). The solution was stirred for 30 min at RT, and concentrated under vacuum. DCM was added and removed twice, and the flask was placed under vacuum at RT. The product was purified by preparative HPLC (C18 column, acetonitrile/water/0.05% TFA). The relevant fractions were pooled (two batches) and diluted 1:1 with water. The solutions were cooled on ice, and the precipitation was induced by adjusting the pH to ca. 5 with 1 N NaOH. The samples were centrifuged (5000 rpm, 10 min, 5° C.). The liquid was decanted off and the pellets were lyophilized to yield a white solid (22 mg+12 mg).
MALDI-MS (alpha-cyano-4-hydroxycinnamic acid) m/z: 6128.7 (M=6125.1).
HPLC-MS m/z: 1532.8 ((M+4)/4=1532.2).

Example 10

Synthesis of $N^{\epsilon B29}$-4-[11-(4-Carboxyphenyl)undecanoylamino]butyryl desB30 human insulin Step 1: 4-Iodobenzoic acid tert-butyl ester 4-Iodobenzoic acid (10 g, 40.3 mmol) was dissolved in dry toluene (100 ml, dried over mol. sieves). The solution was heated to 70° C. under a flow of nitrogen. A solution of N,N'-dimethylformamide di-tert-butyl acetal (24.6 g, 121 mmol) in toluene (25 mL) was added over ca. 30 min. The reaction was mixed for 16 h. At some point the heating unit failed, so the reaction cooled from 70° C. to rt. The solution was heated to 70° C. for and mixed for 5 h. The sample was concentrated under vacuum, and AcOEt (400 ml) was added. The solution was then washed with 1:1 sat. $NaHCO_3$/water (150 ml), and sat. $NaHCO_3$, water and sat. NaCl (75 mL each). The organic phase was dried ($MgSO_4$) and concentrated under vacuum to yield light brown oil.
HPLC-MS m/z: 327 (M+23).
$^1$H-NMR ($CDCl_3$, 400 MHz) δ 7.77 (d, 2H), 7.69 (d, 2H), 1.58 (s, 9H).

Step 2: 11-Iodo undecanoic acid methyl ester

11-Bromo undecanoic acid methyl ester (20.2 g, 72.3 mmol) was dissolved in acetone (200 ml). Sodium iodide (54 g, 361 mmol) was added and reaction was refluxed under nitrogen for 16 h. After cooling to RT the salts were filtered off. The filtrate was concentrated under vacuum and water (200 ml) was added. The solution was extracted with AcOEt (2×100 ml) adding some sat. NaCl to aid phase separation. The organic extracts were pooled and washed with water (100 ml) plus a little sat. NaCl, and sat. NaCl (50 mL). Dry over $MgSO_4$. The solution was a red-orange color. Three teaspoons of activated charcoal were added. After mixing, the solution was filtered through a bed of celite. The filtrate was concentrated under vacuum to yield a light yellow oil (20.96 g, 89%).
HPLC-MS m/z: 327 (M+1).
$^1$H-NMR ($CDCl_3$, 300 MHz) δ 3.67 (s, 3H), 3.19 (t, 2H), 2.30 (t, 2H), 1.74-1.89 (m, 2H), 1.53-1.70 (m, 2H), 1.34-1.46 (m, 2H), 1.28 (br, 10H).

Step 3: 4-(10-Methoxycarbonyldecyl)benzoic acid tert-butyl ester

All glassware was dried prior to use. THF was dried over molecular sieves. LiCl was dried at 150° C. for 1 h, then stored in a closed bottle. All reaction solutions were made under nitrogen, and the solutions were transferred via syringe. 4-Iodobenzoic acid tert-butyl ester (1.2 g, 3.95 mmol) was dissolved in THF (3 ml) and cooled to −30° C.

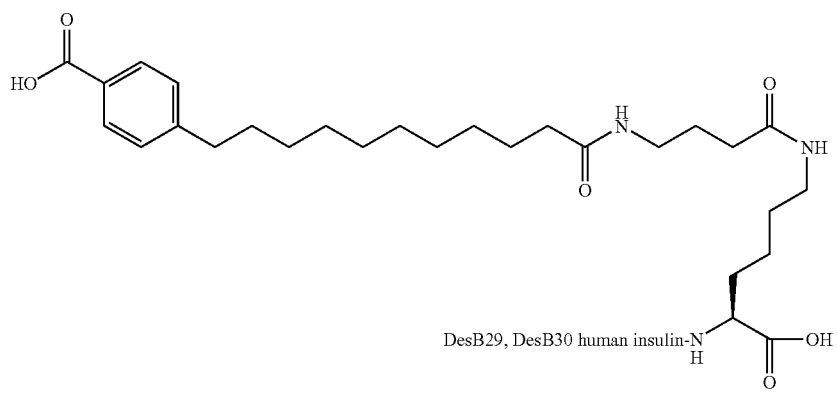

Isopropyl magnesium chloride (4.34 mmol, 2M in THF) was added over 5 minutes, and the solution was stirred for 1 hr at a temperature between −18° C. to −25° C. The solution was cooled to −22° C., and a mixture of CuCN (0.389 g, 4.34 mmol) and LiCl (0.368 g, 8.68 mmol) in THF (4.2 ml) was then added. The reaction vessel was removed from cooling and allowed to warm to RT (ca. 10 min). Trimethylphosphite (0.95 mL) was added, and after stirring for 5 min at rt, a solution of 11-iodo-undecanoic acid methyl ester (1.0 g, 3.16 mmol) in THF (3 ml) was added. The solution was mixed at rt for 16 h. Sat. $NH_4Cl$ (3 ml) was added, and the solution was poured into water (60 mL). The solution was extracted with AcOEt (3×35 ml). The organic extracts were pooled and washed with water (30 mL) using some Sat. NaCl to aid phase separation. The solvent was removed under vacuum to yield a biphasic residue. AcOEt (ca 2 ml) was added and the flask was swirled gently. Not all of the thick white residue dissolved. The portion which dissolved was added to a column of silica (50 g) and eluted with AcOEt: heptane 1:11. The appropriate fractions were concentration under vacuum to yield an oil (1.25 g). The oil was dissolved in acetone (30 mL), and piperidine (1 mL) was added. NaI (0.8 g) was added and the mixture was stirred and refluxed for 16 h. The mixture was concentrated under vacuum and partitioned between AcOEt (50 mL) and 1 N HCl (25 mL). The organic phase was washed with 1 N HCl (2×25 mL), dried over $MgSO_4$, and concentrated under vacuum to yield a colorless oil (1.1 g). The product was purified by flash chromatography (eluant: AcOEt:heptane 1:11, 150 g silica) to yield a colorless oil (0.72 g, 61%).

HPLC-MS m/z: 399 (M+23).

$^1$H-NMR ($CDCl_3$, 300 MHz) δ 7.90 (d, 2H), 7.21 (d, 2H), 3.66 (s, 3H), 2.64 (t, 2H), 2.30 (t, 2H), 1.48-1.70 (m, 13H), 1.27 (br, 12H).

Step 4: 4-(10-Carboxydecyl)benzoic acid tert-butyl ester

The compound was prepared in analogous fashion to the procedure used in the preparation of 4-(9-Carboxynonyloxy) benzoic acid tert-butyl ester to yield a white solid (0.68 g).

HPLC-MS m/z: 385 (M+23).

$^1$H-NMR ($CDCl_3$, 300 MHz) δ 7.90 (d, 2H), 7.21 (d, 2H), 2.64 (t, 2H), 2.34 (t, 2H), 1.53-1.71 (m, 13H), 1.28 (br, 12H).

Step 5: 4-[10-(2,5-Dioxopyrrolidin-1-yloxycarbonyl) decyl]benzoic acid tert-butyl ester The compound was prepared in analogous fashion to the procedure used in the preparation of 4-[9-(2,5-Dioxopyrrolidin-1-yloxycarbonyl)nonyloxy]benzoic acid tert-butyl ester.

HPLC-MS m/z: 482 (M+23).

$^1$H-NMR ($CDCl_3$, 400 MHz) δ 7.89 (d, 2H), 7.21 (d, 2H), 2.76-2.93 (m, 4H), 2.54-2.68 (m, 2H), 1.67-1.81 (M, 2H), 1.52-1.66 (m, 11H), 1.35-1.43 (M, 2H), 1.19-1.35 (br, 10H).

Step 6: 4-[10-(3-Carboxy-propylcarbamoyl)decyl]benzoic acid tert-butyl ester 4-[10-(2,5-Dioxopyrrolidin-1-yloxycarbonyl)decyl]benzoic acid tert-butyl ester (300 mg, 0.65 mmol) was dissolved in DMF (3 ml) and 4-amino butyric acid (67 mg, 0.65 mmol). The mixture was stirred for 16 h under nitrogen. The solvent was removed under vacuum and AcOEt (35 ml) was added. The solution was washed with 0.2 N HCl and water (15 ml each). Sat. $NaHCO_3$ was added (not intended) to the organic phase. DCM (50 ml) was added. Some of the organic phase was removed and DCM (100 ml) was added to the aqueous phase and allowed to stand overnight. The mixture was cooled on ice and the pH was adjusted to 1.9 with 4N HCl. The organic phase was isolated, dried over $MgSO_4$ and concentrated under vacuum to yield on oil (220 mg, 76% yield).

HPLC-MS m/z: 470 (M+23).

$^1$H-NMR ($CDCl_3$, 400 MHz) δ 7.89 (d, 2H), 7.21 (d, 2H), 5.79 (br, 1H), 3.27-3.40 (m, 2H), 2.64 (t, 2H), 2.40 (t, 2H), 2.18 (t, 2H), 1.78-1.91 (m, 2H), 1.51-1.61 (m, 13H), 1.35-1.43 (M, 2H), 1.17-1.36 (br, 12H).

Step 7: 4-{10-[3-(2,5-Dioxo-pyrrolidin-1-yloxycarbonyl)propylcarbamoyl]decyl}benzoic acid tert-butyl ester The compound was prepared in analogous fashion to the procedure used in the preparation of 4-[9-(2,5-Dioxopyrrolidin-1-yloxycarbonyl)nonyloxy]benzoic acid tert-butyl ester, but TSTU was used instead of HSTU. Precipitation (DCM/Heptane) yielded white crystals (180 mg, 70% yield).

HPLC-MS m/z: 568 (M+23).

$^1$H-NMR ($CDCl_3$, 400 MHz) δ 7.89 (d, 2H), 7.21 (d, 2H), 5.83 (br, 1H), 3.30-3.43 (m, 2H), 2.85 (br, 4H), 2.57-2.73 (m, 4H), 2.15 (t, 2H), 1.92-2.07 (m, 2H), 1.56-1.64 (m, 13H), 1.18-1.36 (br, 12H).

Step 8: $N^{εB29}$-4-[11-(4-carboxyphenyl)undecanoylamino]butyryl desB30 human insulin The compound was prepared in analogous fashion to the procedure used in the preparation of example 9 to yield 30 mg.

MALDI-MS (alpha-cyano-4-hydroxycinnamic acid) m/z: 6067 (M=6080, reference standard (M=5706) showed M−13).

HPLC-MS m/z: 1520.9 ((M+4)/4=1521).

Example 11

Synthesis of N^{εB29}-(3-(3-{4-[3-(7-carboxyheptanoy-lamino)propoxy]butoxy}propylcarbamoyl)-propionyl-γ-glutamylamide) desB30 human Insulin

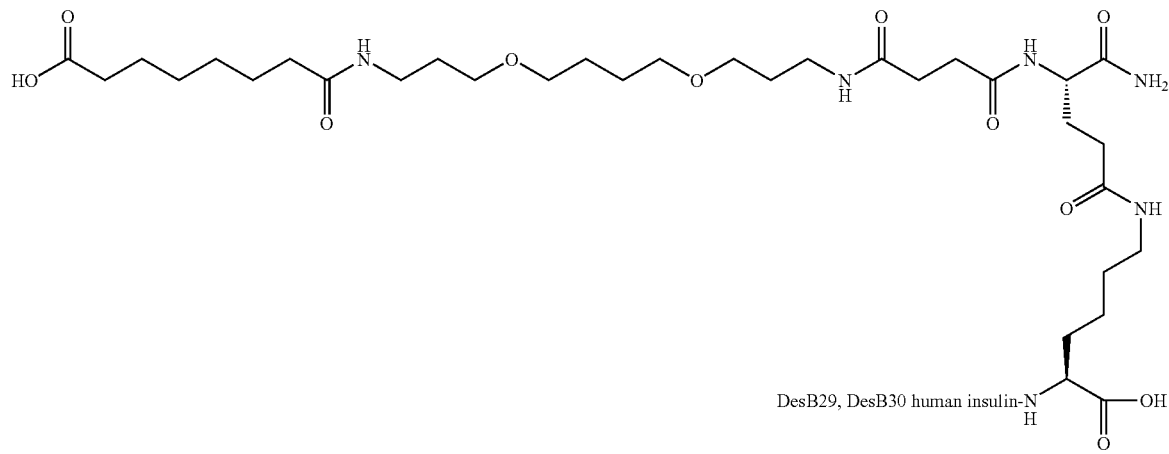

Step 1: N-{3-[4-(3-tert-Butoxycarbonylaminopropoxy)-butoxy]-propyl}succinamic acid 123-0000-3007

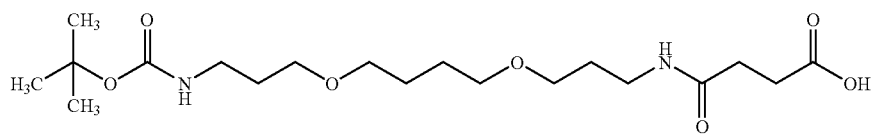 [SMILES: CC(C)(C)OC(=O)NCCCOCCCCOCCCNC(=O)CCC(=O)O]

1-(tert-Butoxycarbonylamino)-4,9-dioxa-12-dodecanamine (5.0 g, 16.45 mmol) was dissolved in THF (30 mL), succinic anhydride (1.81 g, 18.1 mmol) in acetonitrile (10 mL) was added and the mixture was heated to 60 C for 4 h, and subsequently stirred at RT overnight.

The mixture was evaporated to dryness and EtAc (50 mL) was added.

The EtAc phase was washed with HCl (0.1 M) 3 times, dried with MgSO$_4$ and subsequently the organic phase was evaporated to dryness which gave 5.86 g (88%) of thick oil.

LCMS: Rt 2.86 min; m/z (M+1) 405. Calcd: 405.

This product was used without further purification.

Step 2: Octanedioic acid tert-butyl ester 2,5-dioxo-pyrrolidin-1-yl ester

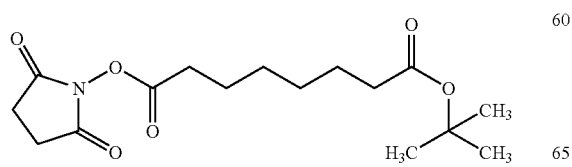

Octanedioic acid mono-tert-butyl ester (3.14 g, 13.63 mmol) was dissolved in THF (100 mL). TSTU (4.9 g, 16.3 mmol) was added and pH was adjusted to 8.5 with DIPEA (2.85 mL).

The mixture was stirred under nitrogen overnight, evaporated to dryness, dissolved in EtAc (50 mL) which subsequently was extracted 2 times with HCL (0.1 M). The organic phase was dried with MgSO$_4$, filtered and evaporated resulting in an slightly yellow oil (5 g, containing small amounts of solvent).

LCMS: Rt 6.56 min; m/z (M+1) 328. Calcd: 328.

Step 3: 7-(3-{4-[3-(3-carboxypropionylamino)propoxy]butoxy}propylcarbamoyl)heptanoic acid tert-butyl ester 123-0000-3012

DMF (10 mL), pH was adjusted to 8.2 with DIPEA (0.8 mL). The mixture was stirred overnight under nitrogen.

The mixture was evaporated and the residue dissolved in EtOAc which was extracted with HCl (0.1 M) 3 times. The organic layer was dried with magnesium sulphate, filtered and the filtrate evaporated to give 3.2 g oil.

LCMS: Rt 4.57 min; m/z 614, corresponding to the activated acid.

This crude product was dissolved in acetonitrile (40 mL) and L-glutamic acid amide (0.6 g, 4.1 mmol) was added together with DMF (5 mL), pH was adjusted to 8.2 with DIPEA (1.4 mL).

The mixture was stirred at RT for overnight; filtration followed by evaporation afforded thick yellow oil.

This was extracted between EtOAc and HCl (0.1 M) as reported above, and the resulting dried EtOAc layer gave 1.66 g crude product on evaporation.

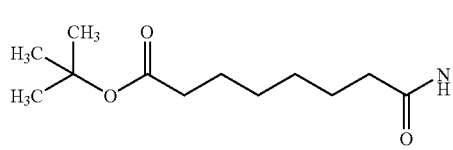

N-{3-[4-(3-tert-Butoxycarbonylaminopropoxy)-butoxy]-propyl}succinamic acid (4.60 g, 11.37 mmol) was stirred with TFA (20 mL) at RT for 60 min, after evaporation the residue was stripped with DCM (30 mL×2) and evaporated to dryness.

The resulting oil was dissolved in acetonitrile (30 mL) and octanedioic acid tert-butyl ester 2,5-dioxo-pyrrolidin-1-yl ester (4.46 g, 13.6 mmol) in DMF (20 mL) was added.

pH was adjusted to 8.5 with DIPEA and the mixture was stirred overnight under nitrogen. The mixture was subsequently evaporated to dryness and redissolved in EtOAc (50 mL). The EtOAc phase was extracted ×3 with HCl (0.1 M), the organic layer dried over magnesium sulphate, filtered and evaporated resulting in a slightly yellow crystalline oil (6.5 g, content of solvent residues).

LCMS: Rt 4.31 min; m/z (M+1) 517. Calcd: 517.

The crude product was used for further reaction without further purification.

Step 4: 7-[3-(4-{3-[3-((S)-1-carbamoyl-3-carboxypropylcarbamoyl)propionylamino]propoxy}butoxy) propylcarbamoyl]heptanoic acid tert-butyl ester 0123-0000-3078

LCMS: Rt 3.62 min; m/z (M+1) 645. The crude product was purified by preparative HPLC using acetonitrile/water/ 0.1% TFA as eluent on C18 column (Jones, Kromasil RP18 5 μm 15×225 mm). Gradient: 0.0-10.0 min 35% acetonitrile A; 10.0-30.0 min 35-90% A; The product was collected in fractions from 16-18 min. The combined fractions were evaporated yielding the wanted product (1.0 g). LCMS: Rt 3.59 min; m/z (M+1) 645, calcd. 645.

Step 5: N$^{\epsilon B29}$-(3-(3-{4-[3-(7 carboxyheptanoylamino)propoxy]butoxy}propylcarbamoyl)propionyl-γ-L-glutamylamide) desB30 human insulin 7-[3-(4-{3-[3-((S)-1-Carbamoyl-3-carboxypropylcarbamoyl)propionylamino]propoxy}butoxy)-propylcarbamoyl]heptanoic acid tert-butyl ester from step 4 (1.0 g, 1.55 mmol) was dissolved in THF (20 mL), TSTU (0.51 g, 1.7 mmol) was added and pH adjusted to >8 with DIPEA (0.27 mL).

The mixture was stirred overnight under nitrogen. Evaporation followed by extraction between EtOAc and HCl (0.1 M), drying of the organic phase (MgSO$_4$) followed by evaporation to dryness gave 21 mg oil, LCMS: Rt. 4.34 min, m/z 742.

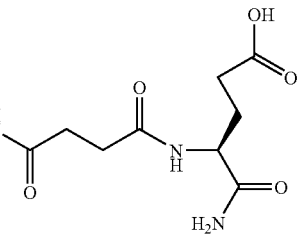

7-(3-{4-[3-(3-Carboxypropionylamino)propoxy] butoxy}propylcarbamoyl)heptanoic acid tert-butyl ester (2.4 g), the crude product from step 3, was dissolved in THF (60 mL), TSTU (2.11 g, 6.97 mmol) was added together with This crude product was dissolved in acetonitrile (10 mL), pH was adjusted to 8 with Na$_2$CO$_3$ (0.1 M) and added to a solution of desB30 human insulin (1 g) dissolved in Na$_2$CO$_3$ solution (15 mL, pH 10.2).

The mixture was stirred under nitrogen at RT for 1 h. Then pH was adjusted to 5.4 by means of HCl (2M) resulting in precipitation. The mixture was filtered, the filtrate freeze dried, and the precipitate dried in vacuum overnight.

Both fractions were purified on Gilson using acetonitrile/water/0.1% TFA as eluent on C18 column (Jones, Kromasil RP18 5 μm 15×225 mm).

Gradient: 0.0-5.0 min 35% acetonitrile (A); 5.0-25.0 min 35-90% A; The product was collected in fractions from 12-15 min. The combined fractions were evaporated, redissolved in water and freeze-dried yielding 27 mg of the wanted product.

LCMS: Rt. 7.76 min, m/z 1570

MALDI-MS (sinnapinic acid): 6277; $C_{280}H_{422}N_{68}O_{84}S_6$ requires 6277.

Example 12

Synthesis of $N^{\epsilon B29}$-ω-carboxy-tridecanoyl-γ-amino-butanoyl desB30 human insulin

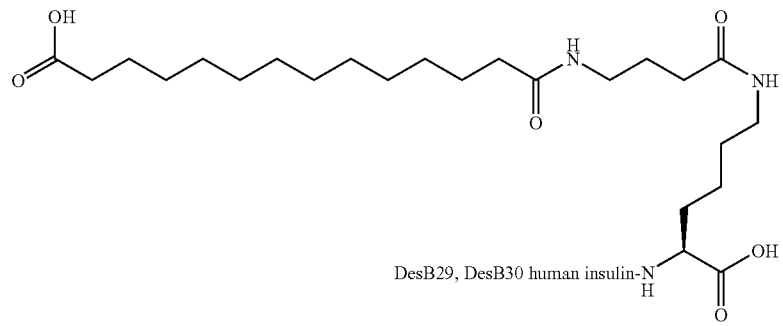

This compound was prepared from tetradecandioic acid and γ-amino-butyric acid in analogy with example 1.

LCMS 6032.1, $C_{271}H_{407}N_{65}O_{79}S_6$ requires 6032.0.

Example 13

Synthesis of $N^{\epsilon B29}$-ω-carboxy-undecanoyl-δ-amino-butanoyl desB30 human insulin

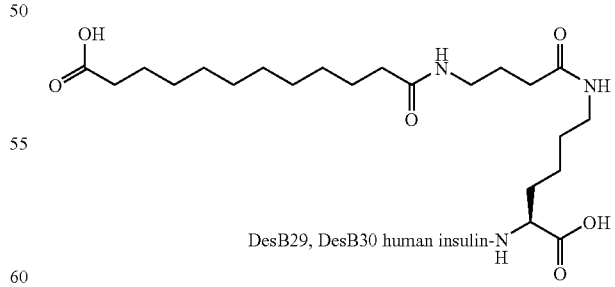

This compound was prepared from dodecandioic acid and γ-amino-butyric acid in analogy with example 1.

LCMS 6003.8, $C_{269}H_{403}N_{65}O_{79}S_6$ requires 6004.0.

Example 14

Synthesis of $N^{\epsilon B29}$-ω-carboxy-tetradecanoyl-γ-amino-butanoyl desB30 human insulin

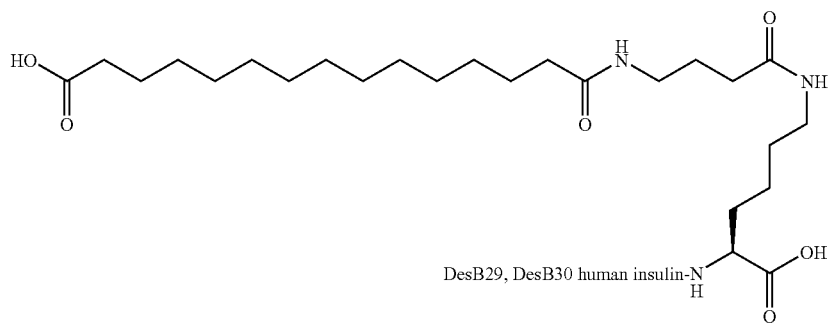

This compound was prepared from pentadecandioic acid and γ-aminobutyric acid in analogy with example 1.

LCMS 6045.6, $C_{272}H_{409}N_{65}O_{79}S_6$ requires 6046.1.

Example 15

Synthesis of $N^{\epsilon B29}$-{4-[10-(4-Carboxy-phenoxy)-decanoylamino]-butyryl} desB30 insulin

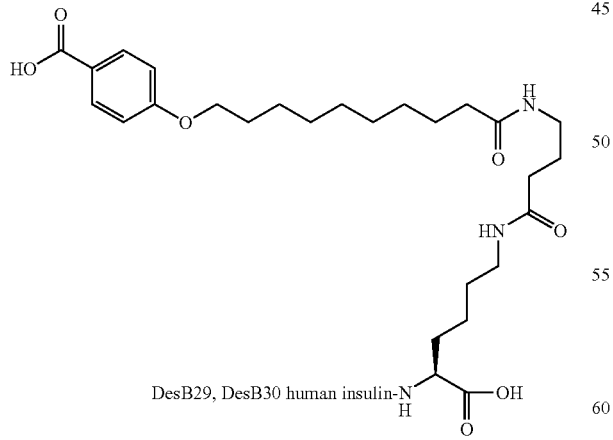

This compound was prepared from 4-(9-methoxycarbonylnonyloxy)benzoic acid tert-butyl ester in analogy with examples 9 and 10.

LCMS: 6095.6, $C_{276}H_{409}N_{65}O_{79}S_6$ requires 6094.1.

Example 16

Synthesis of N$^{\epsilon B29}$-{4-[(14-Carboxy-tetradecanoy- lamino)-methyl]-benzoyl} desB30 insulin

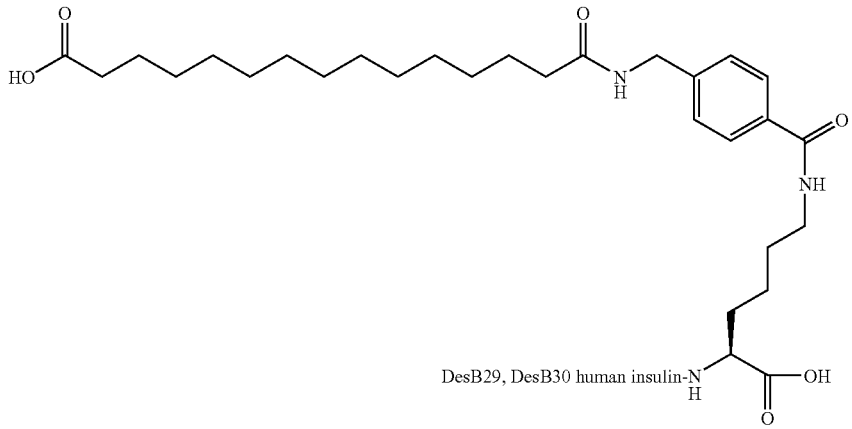

This compound was prepared from 4-aminomethyl benzoic acid in analogy with example 1.

LCMS: 6082.0, $C_{275}H_{406}N_{66}O_{81}S_6$ requires 6082.1.

Example 17

Synthesis of N$^{\epsilon B29}$-[16-(4-Carboxy-phenoxy)-hexadecanoyl] desB30 insulin

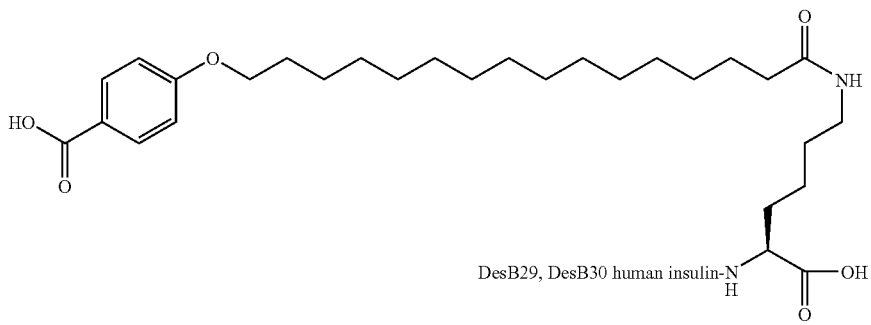

Step 1: 16-Bromohexadecanoic acid methyl ester

16-Bromohexadecanoic acid (6 g, 17.9 mmol) was dissolved in methanol (35 mL), toluene (100 mL) and trimethylorthoformate (20 mL). Amberlyst 15 was added and the mixture was stirred under nitrogen for 16 h at 55° C. The mixture was concentrated, and dissolved in methanol (ca. 50 mL) and DCM (30 mL). The resin was filtered off, and the filtrate was concentrated. The volume was increased to ca. 40 mL with methanol. Cooling produced crystals which were filtered off, washed with cold methanol and dried to yield white crystals (5.61 g, 90% yield).

$^1$H-NMR (DMSO, 300 MHz) 3.57 (s, 3H), 3.52 (t, 2H), 2.28 (t, 2H), 1.78 (m, 2H), 1.50 (m, 2H), 1.37 (m, 2H).

The remainder of the steps were performed in analogy with example 9.

LCMS: 6081.2, $C_{276}H_{410}N_{64}O_{79}S_6$ requires 6081.1.

Example 18

Synthesis of $N^{\epsilon B29}$-{4-[(15-carboxypentadecanoylamino)benzoyl]-desB30 human insulin

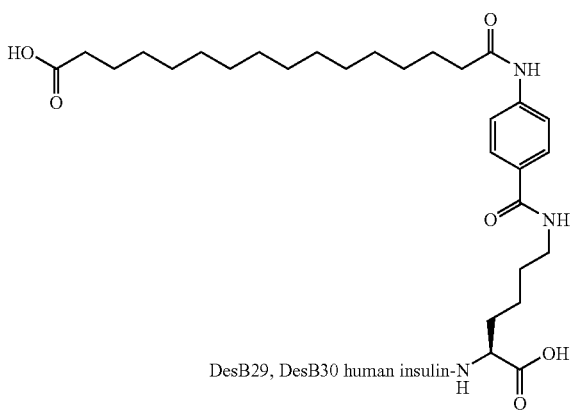

Step 1: 4-(15-tert-Butoxycarbonylpentadecanoylamino)-benzoic acid

Mono-tert-butyl hexadecandioate hexadecadioic acid (400 mg, 1.17 mmol) was dissolved in NMP (6 ml). 1-(3-dimethylaminopropyl)-3-ethylcarbodiimide hydrochloride (223 mg, 1.17 mmol) and 1-hydroxy-7-azabenzotriazole (156 mg, 1.17 mmol) was added and the mixture was heated to 50 degrees celcius for 90 min. 4-aminobenzoic acid (320 mg, 2.34 mmol) and DIEA (0.6 mL, 3.51 mmol) was added and the mixture was stirred under nitrogen flow overnight. The mixture is transferred is separated between saturated aqueous $NaHCO_3$ (50 mL) and diethyl ether (100 mL). $NaHSO_4$ (50 mL, 10% in water) was added and the organic phase isolated, dried ($MgSO_4$) and solvent removed in vacuo. The crude product was recrystallized from ethanol to give 4-(15-tert-butoxycarbonylpentadecanoylamino)-benzoic acid.

$^1$H-NMR (DMSO-$d_6$) δ: 10.18 (s, 1H), 7.87 (d, 2H), 7.69 (d, 2H), 2.33 (t, 2H), 2.15 (t, 2H), 1.58 (t, 2H), 1.46 (t, 2H), 1.38 (s, 9H)$_m$ 1.31-1.20 (m, 20H).

Step 2: 4-(15-tert-Butoxycarbonyl-pentadecanoylamino)-benzoic acid 2,5-dioxo-Pyrrolidin-1-yl ester 4-(15-tert-Butoxycarbonylpentadecanoylamino)-benzoic acid (29 mg, 0.063 mmol) was converted to the succinimidyl ester using TSTU similar to described above.
HPLC-MS, m/z=559 (M+23, M+Na).

Step 3: $N^{\epsilon B29}$-{4-[(15-carboxypentadecanoylamino)benzoyl]-desB30 human insulin DesB30 human insulin (355 mg, 0.062 mmol) was dissolved in DMSO (3.5 mL), triethylamin (0.622 mmol, 0.087 mL) was added. 4-(15-tert-Butoxycarbonyl-pentadecanoylamino)-benzoic acid 2,5-dioxo-pyrrolidin-1-yl ester (28.3 mg, 0.051 mmol) was dissolved in DMSO (0.5 mL and added). The mixture was carefully stirred for 30 minutes at room temperature. The mixture was frozen by cooling with an icebath and water (7 mL) was added and the mixture left standing at room temperature until the frozen mixture had dissolved. pH was adjusted to pH=5.3 using 1 N HCl and precipitate isolated by centrifuge, washed once with water followed by centrifuge. Trifluoroacetic acid (15 mL) was added and the mixture was stirred for 30 minutes, poured into diethyl ether (50 mL) while maintaining cooling on an icebath. The crude product was isolated by centrifuge and dissolved in 10 mM TRIS+15 mM $(NH_4)_2SO_4$ in 20% EtOH, pH 7.3 and subjected to purification on an ÄKTA purifier employing a reversed phase HPLC, Jupiter 5269, C4 250/20 mm, 15 μM, 300 Å. The buffer consisted of A-buffer 10 mM TRIS+15 mM $(NH_4)_2SO_4$ in 20% EtOH, pH 7.3 and a B-buffer 80% EtOH. The product was eluted with a gradient 15-60% B with 8 ml/min. Fractions containing product were collected an pH adjusted to pH=5.2. $N^{\epsilon B29}$-{4-[(15-carboxypentadecanoylamino)benzoyl]-desB30 human insulin was isolated by centrifuges and lyophilized.

LCMS: 6092.0, $C_{276}H_{409}N_{65}O_{79}S_6$ requires 6094.1.

Example 19

Synthesis of $N^{\epsilon B29}$-{4-[(15-Carboxy-pentadecanoylamino)-methyl]-benzoyl}-desB30 insulin

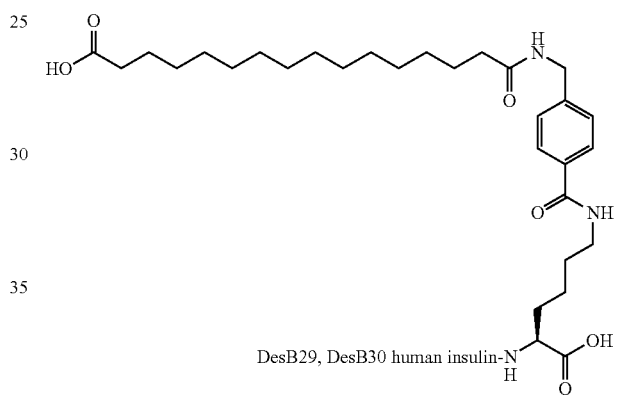

Step 1: 4-[(15-tert-Butoxycarbonylpentadecanoylamino)methyl]benzoic acid

Hexadecanedioic acid tert-butyl ester 2,5-dioxo-pyrrolidin-1-yl ester (370 mg, 0.842 mmol) was dissolved in NMP (8 mL), 4 aminomethyl benzoic acid (127.2 mg, 0.842 mmol) was added, the mixture was stirred at room temperature overnight, followed by heating at for 2 hours at 50 degrees celcius. After cooling to room temperature the mixture was poured into water. Product isolated by filtration dried and used for the next step without any further purification.

$^1$H-NMR (DMSO-$d_6$) (selected signals) δ: 7.88 (d, 2H), 7.34 (d, 2H), 4.31 (d, 2H), 2.15 (m, 4H), 1.47 (m, 4H), 1.38 (s, 9H), 1.23 (br s, 2H), 1.38 (s, 9H).
HPLC-MS: m/z=498 (M+Na)

Step 2: $N^{\epsilon B29}$-{4-[(15-Carboxy-pentadecanoylamino)-methyl]-benzoyl}-desB30 insulin The 4-[(15-tert-Butoxycarbonyl pentadecanoylamino)methyl]benzoic acid was converted to converted to the succinimidyl ester and reacted with DesB30 human insulin similar to described above. The product was purified on an ÄKTA purifier employing a reversed phase HPLC, Jupiter 5269, C4 250/20 mm, 15 μM, 300 Å. The buffer consisted of A-buffer 10 mM TRIS+15 mM $(NH_4)_2SO_4$ in 20% EtOH, pH 7.3 and a B-buffer 80% EtOH. The product was eluted with a gradient 15-60% B with 8 ml/min. Followed by purification with RP-HPLC on a Waters Prep LC2000, on C18, 5 cm×20 cm, flow 20 ml/min using acetonitrile/water 36-42% gradient containing 0.1% TFA. Fractions containing product was collected and lyophilized. To the lyophilized material was added water (7.2 mL) and pH adjusted to 8.98 with 1 N+0.1 N NaOH. The pH was adjusted back to 5.2-5.5 with 0.1 N HCl. The product precipitated, isolated by centrifuge and lyophilized to give the title compound.

LCMS: 6108.0, $C_{277}H_{411}N_{65}O_{79}S_6$ 6108.1

Example 20

Hydrophobicity Albumin Affinity Self-Association and Mixability of Long.Acting and Short-Acting Insulins Analysis of Selv-Associating Properties of the Insulin Derivatives of the Invention The ability of the insulin derivatives of the invention to self-associate into large, but soluble complexes is analysed using SEC (size exclusion chromatography):

| Column: | Superose ™ 6 PC 3.2/30, CV = 2.4 ml (Amerham Biosciences) |
| --- | --- |
| Temperature: | 37° C. |
| SEC buffer: | 140 mM NaCl, 10 mM TrisHCl, 0.01% NaN$_3$, pH 7.5 |
| Injection volume: | 20 µl |
| Flow: | 0.05 ml/min |
| Runtime: | 60 min and equillibration of additional 100 min |

For this analysis the insulin derivatives of the invention are in a solution consisting of 0.6 mM derivative, 2.1 $Zn^{2+}$/hexamer, 16 mM phenol, 7 mM phosphate pH 7.8. The retention time of the derivative is then compared to the retention times of the following standard molecules: Blue dextran (>5 MDa, $K_{AV}$ 0.0), Thyroglobulin (669 kDa, $K_{AV}$ 0.28), Ferritin (440 kDa, $K_{AV}$ 0.39), Ovalbumin (44.5 kDa, $K_{AV}$ 0.56), Ribonuclease (13.7 kDa, $K_{AV}$ 0.69) and a second reference of Albumin (66 kDa, $K_{AV}$ 0.53), Co(III)insulin-hexamer (35 kDa, $K_{AV}$ 0.61), and monomeric insulin X2 (6 kDa, $K_{AV}$ 0.73).

The following equation is used to determine the $K_{av}$ for the derivative:

$$K_{av} = (t-t_0)/(V_t/(f+t_d-t_0))$$

Where t is the retention time for a given peak, $t_0$ is the retention time for Blue dextran, $V_t$ is the total column volume (here 2.4 ml), f is the flow (here 0.04 ml/min), and $t_d$ is the retention time for Blue dextran without the column in the system.

The $K_{av}$ value indicates the degree of selv-association of a derivative, i.e. a large $K_{av}$ similar to the $K_{av}$ for the Co(III) insulin hexamer and X2 insulin monomer shows low or no propensity of the derivative to form large, selv-associated complexes, while very small $K_{av}$ close to zero or even negative shows great propensity of the derivative for selv-association into large, soluble complexes.

Hydrophobicity Data on Insulin Derivatives According to the Invention.

The hydrophobicity (hydrophobic index) of the insulin derivatives of the invention relative to human insulin, $k'_{rel}$, was measured on a LiChrosorb RP18 (5 µm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel} = (t_{derivative} - t_0)/(t_{human} - t_0)$. $k'_{rel}$ found for a number of insulin derivatives according to the invention are given in Table 1.

Human Serum Albumin Affinity Assay

Relative binding constant of 125I-TyrA14-analogue to human serum albumin immobilised on Minileak particles and measured at 23° C. (detemir=1 in saline buffer).

Mixability of Long-Acting and Short-Acting Insulins as Analyzed by Size-Exclusion Chromatography of Insulin Mixtures SEC: Mixability of Insulin Aspart (3 Zn/6 insulin, glycerol 1.6%, 16 mM phenol and 16 mM m-cresol, sodium chloride 10 mM, phosphate 7 mM, pH 7.4) and prolonged acting insulin (2.1 or 6 Zn/6 insulin) 30:70, as measured by collecting fractions from SEC (as described above) and quantifying by HPLC the presence of prolonged-acting and fast-acting insulins in the high molecular weight fraction (fraction 2, MW>HSA) and in the low molecular weight fraction (fraction 3, MW=HSA), respectively.

Four fractions are collected at size of 16 min after delay, of which fraction 2 [16-32 min] (peak 1) contain associated form larger than albumin (32 min correspond to $K_{AV}$ 0.46) and fraction 3 (peak 2) contain dihexameric, hexameric, dimeric and monomeric forms of insulin.

HPLC: Reverse phase chromatography on a Zorbax Eclipse XDB-C18 2.1*15 mm (1.8 µm) gradient eluted with buffer A: 0.2 M sodium sulphate, 0.04 M sodium phosphate, 10% acetonitrile, pH 7.2 and buffer B: 70% acetonitrile at 30° C., 19-34% B in 4.5 min. linear, sudden initial condition at 5 min., run time of 7 min., flow of 0.5 ml/min., injection volume of 14 µL and UV detection at 276 nm using Insulin Aspart reference of 609 µM for both analogues.

| Compound | Hydrophobicity relative to human insulin | Insulin receptor affinity relative to human insulin | Human serum albumin affinity relative to insulin detemir | Self-association: $K_{av}$ (% area of peak) |
| --- | --- | --- | --- | --- |
| Example 1 | ++ 1.366 | ++ 37% | ++ 1.9 | +++ 0.0 (87%) 0.74 (13%) |
| Example 2 | ++ 1.933 | ++ 35% | ++ 2.2 | +++ 0.0 (94%) 0.75 (6%) |
| Example 3 | ++ 1.095 | ++ 30% | + 0.37 | +++ 0.08 (76%) 0.74 (24%) |
| Example 4 | +++ 0.716 | +++ 52% | + 0.069 | ++ 0.15 (77%) 0.74 (23%) |
| Example 5 | ++ 1.75 | ++ 30% | ++ 1.93 | +++ 0.02 (93%) 0.76 (7%) |
| Example 6 | ++ 1.617 | ++ 33% | ++ 1.36 | +++ 0.01 (90%) |

-continued

| Compound | Hydrophobicity relative to human insulin | Insulin receptor affinity relative to human insulin | Human serum albumin affinity relative to insulin detemir | Self-association: $K_{av}$ (% area of peak) |
|---|---|---|---|---|
| Example 7 | ++ 2.936 | ++ 37% | +++ 2.62 | +++ 0.01 (90%). |
| Example 8 | ++ 2.461 | ++ 38% | ++ 1.95 | n.a. |
| Example 9 | +++ 0.738 | ++ 58% | + 0.06 | +++ 0.05 (90%) 0.75 (10%) |
| Example 10 | ++ 1.803 | ++ 43% | + 0.33 | ++ 0.26 (48%) |
| Example 11 | +++ 0.435 | ++ 43% | n.a. | n.a. |
| Example 12 | +++ 0.989 | +++ 49% | + 0.25 | ++ 0.17 (44%) 0.7 (56%) |
| Example 13 | +++ 0.552 | +++ 59% | + 0.03 | + 0.69 (100%) |
| Example 14 | ++ 1.61 | ++ 48% | n.a. | n.a. |
| Example 15 | ++ 1.09 | ++ 47% | + 0.14 | ++ 0.28 (42%) 0.72 (58%) |
| Example 16 | ++ 2.21 | +++ 88% | ++ 1.9 | ++ 0.3 (28%) 0.52 (72%) |
| Example 17 | + 15.9 | ++ 12% | +++ 2.97 | ++ 0.12 (87%) 0.79 (13%) |
| Example 18 | ++ 4.16 | ++ 36% | +++ 5.83 | ++ 0.33 (24%) 0.5 (76%) |
| Example 19 | ++ 3.73 | ++ 42% | +++ 5.27 | ++ 0.33 (24%) 0.51 (76%) |

Table legend:
Hydrophobicity relative to human insulin: k'rel < 1: +++, 1-10: ++, >10: + (HI = 1)
Insulin receptor affinity relative to human insulin: <5%: +, 5-50%: ++, >50%: +++
Human serum albumin affinity relative to insulin detemir: <0.5: +, 0.5-2: ++, >2: +++
Self-association: $K_{av}$ < 0.1: +++, $K_{av}$ < 0.55: ++ and $K_{av}$ ≥ 0.55: +
$K_{av}$ = 0.55 for human serum albumin, $K_{av}$ = 0.63 for human insulin Co(III)hexamer,
$K_{av}$ = 0.72 for the monomeric insulin analogue X2.
n.a. = not analyzed.

Example 21

Figure 4:
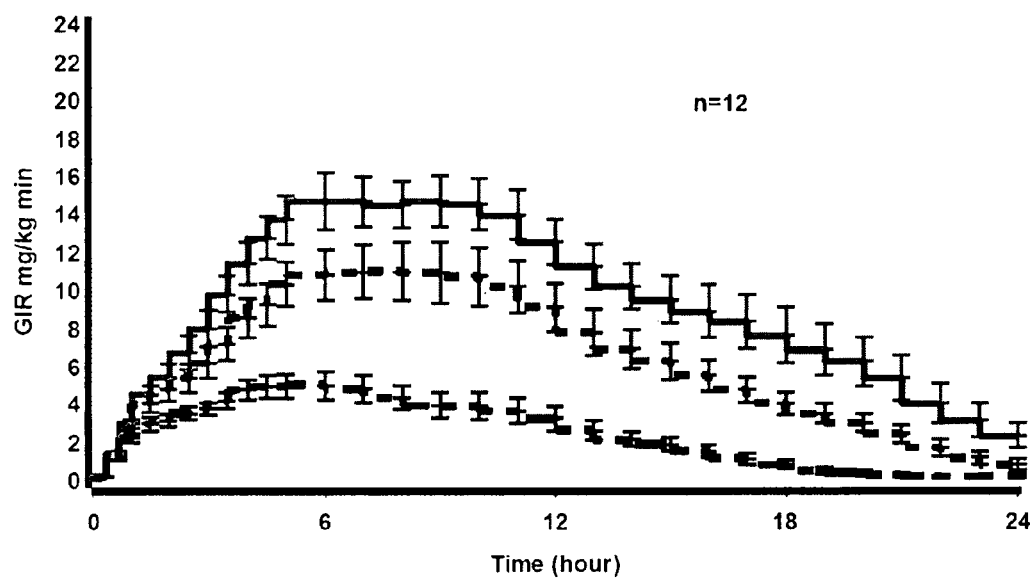
FIG. 4: Clamp action profile after subcutaneous injection of the insulin derivative in example 2 in three doses demonstrating long effect of insulin action. The clamp experiment is performed in accordance with example 21.

Euglycaemic Glucose Clamp after s.c. Administration of Insulin Preparations to Pigs Female pigs, 60-90 kg, fasted for 18 h. During the experiments the pigs are free to move in their pens. An insulin dose is administered s.c., depending of dose size often divided in two depots. Each pig is kept euglycaemic at its individual fasting glucose levels for up to 24 h by a variable rate intravenous infusion of a 20% glucose solution. The infusion is given through a catheter inserted in the jugular vein. Depending on changes in plasma glucose concentrations observed during frequent plasma glucose monitoring, the necessary adjustments of the glucose infusion are made empirically. Blood samples are collected in EDTA glass tubes every 15-30 min, plasma separated for glucose and insulin measurements. Glucose is determined within 1.5 min of blood sampling with an YSI (Yellow Springs Instruments) glucose analyser (glucose oxidase method). Mean glucose infusion rate (GIR) profiles and mean plasma insulin profiles are made for each insulin preparation. (FIGS. 2-4 show mean±SEM).

Pharmacological Methods

Assay (I)

Insulin Receptor Binding of the Insulin Derivatives of the Invention

The affinity of the insulin analogues of the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 μl of a 1:5000 diluted purified recombinant human insulin receptor-exon 11, an amount of a stock solution of A14 Tyr[$^{125}$I]-human insulin corresponding to 5000 cpm per 100 μl of reagent mix, 12 μl of a 1:1000 dilution of F12 antibody, 3 ml of SPA-beads and binding buffer to a total of 12 ml. A total of 100 μl was then added and a dilution series is made from appropriate samples. To the dilution series was then added 100 μl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Assay (II)

Potency of the Insulin Derivatives of the Invention Relative to Human Insulin

Sprague Dawley male rats weighing 238-383 g on the experimental day are used for the clamp experiment. The rats has free access to feed under controlled ambient conditions and fast overnight (from 3 pm) prior to the clamp experiment.

Experimental Protocol

The rats are acclimatized in the animal facilities for at least 1 week prior to the surgical procedure. Approximately 1 week prior to the clamp experiment Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

The clamp technique employed is adapted from (1). At 7 am on the experimental day overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels are measured at 10 min intervals throughout and infusion of 20% aqueous glucose is adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides were confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

Test Compounds and Doses:

Insulins to be tested are diluted from a stock solution containing 97 µM of the insulin derivative in 5 mM phosphate pH 7.7. The final concentration in the solution ready for use is 0.45 µM of the insulin derivative, 5 mM of phosphate, 100 mM of sodium chloride, 0.007% of polysorbate 20. The pH was 7.7 and the i.v. infusion rate was 15 and 20 pmol·min$^{-1}$·kg$^{-1}$.

A stock solution of human insulin that is used as reference compound was formulated in a similar medium and infused i.v. at 6, 15 or 30 pmol·min$^{-1}$·kg$^{-1}$.

Both stock solutions are stored at −20° C. and thawed overnight at 4° C. before use. The solutions are gently turned upside down several times 15 min before they are transferred to the infusion syringes.

Assay (III)

Determination in Pigs of T$_{50\%}$ of the Insulin Derivatives of the Invention

T$_{50\%}$ is the time when 50% of an injected amount of the A14 Tyr[$^{125}$I] labelled derivative of an insulin to be tested has disappeared from the injection site as measured with an external γ-counter.

The principles of laboratory animal care are followed, Specific pathogen-free LYYD, non-diabetic female pigs, crossbreed of Danish Landrace, Yorkshire and Duroc, are used (Holmenlund, Haarloev, Denmark) for pharmacokinetic and pharmacodynamic studies. The pigs are conscious, 4-5 months of age and weighing 70-95 kg. The animals fast overnight for 18 h before the experiment.

Formulated preparations of insulin derivatives labelled in TyrA$^{14}$ with $^{125}$I are injected sc. in pigs as previously described (Ribel, U., Jørgensen, K, Brange, J, and Henriksen, U. The pig as a model for subcutaneous insulin absorption in man. Serrano-Rios, M and Lefèbvre, P. J. 891-896.1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin detemir (both $^{125}$I labelled in Tyr A14) are injected at two separate sites in the neck of each pig.

The disappearance of the radioactive label from the site of sc. injection is monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it is possible to measure continuously the disappearance of radio-activity from a subcutaneous depot for several days using cordless portable device (Scancys Laboratorieteknik, Værløse, DK-3500, Denmark). The measurements are performed at 1-min intervals, and the counted values are corrected for background activity.

The invention claimed is:

1. An insulin derivative having a formula

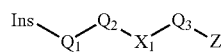

wherein Ins is a parent insulin moiety and $Q_1$-$Q_2$-$X_1$-$Q_3$-Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

$Q_1$ is:

an amino acid amide of an amino acid with a carboxylic acid in the side chain, or an amino acid with an uncharged side chain, which residue forms, with its α-carboxylic acid group, an amide group together with the α-amino group of the N-terminal amino acid residue of the B chain of Ins or together with the ε-amino group of a Lys residue present in the A or B chain of Ins, or a chain composed of two, three or four residues, where each residue is, independently, an α-carboxy amino acid amide with a carboxylic acid in the side chain, or an amino acid residue with an uncharged side chain, where each residue forms, with its a-carboxylic acid group, an amide group together with either (i) one of the remaining residues forming the chain or (ii) the α-amino group of the N-terminal amino acid residue of the B chain of Ins or to the ε-amino group of a Lys residue present in the A or B chain of Ins, or a bond;

$Q_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$— or
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, or —(CH$_2$)$_{1-6}$CH$_3$;

provided that if an amine in $Q_2$ forms a bond with the rest of the substituent, the amine must be bound to the rest of the substituent via a carbonyl group;

$Q_3$ is —(CH$_2$)$_m$— where m is an integer in the range of 6 to 32;

a divalent hydrocarbon chain comprising 1, 2 or 3 —CH═CH— groups and a number of —CH$_2$— groups sufficient to give a total number of carbon atoms in the chain in the range of 4 to 32; or a divalent hydrocarbon chain of the formula —(CH$_2$)$_s$C$_6$H$_4$(CH$_2$)$_w$— wherein s and w are integers or one of them is zero so that the sum of s and w is in the range of 6-30;

X$_1$ can be —C=O or a bond;

Z is:
- —COOH;
- —CO-Asp;
- —CO-Glu;
- —CO-Gly;
- —CO-Sar;
- —CH(COOH)$_2$;
- —N(CH$_2$COOH)$_2$;
- —SO$_3$H;
- —OSO$_3$H;
- —OPO3H$_2$,
- —PO$_3$H$_2$ or
- tetrazol-5-yl;

and any Zn$^2$ complex thereof wherein the insulin derivative is mixable with a fast-acting insulin with no blunting.

2. The insulin derivative according to claim 1, wherein Z is —COOH.

3. The insulin derivative according to claim 1, wherein the parent insulin is an insulin analogue.

4. The insulin derivative according to claim 3, wherein the parent insulin is selected from the group consisting of: desB30 human insulin, GlyA21 human insulin, GlyA21desB30 human insulin, GlyA21ArgB31ArgB32 human insulin, LysB3GluB29 human insulin, LysB28ProB29 human insulin and ThrB29LysB30 human insulin.

5. A pharmaceutical composition for the treatment of diabetes in a patient in need of such treatment, comprising a therapeutically effective amount of an insulin derivative according to claim 1 together with a pharmaceutically acceptable carrier.

6. A method for producing a pharmaceutical composition comprising adding up to about 10 zinc atoms per 6 molecules of insulin derivative to an insulin derivative of claim 1.

7. A method of treating diabetes in a patient in need of such a treatment, comprising administering to the patient a therapeutically effective amount of an insulin derivative according to claim 1.

8. The method according to claim 7 for pulmonary treatment of diabetes.

9. A mixture of an insulin derivative according to claim 1 and a rapid acting insulin analogue selected from the group consisting of AspB28 human insulin; LysB28ProB29 human insulin and LysB3GluB29 human insulin.

10. An insulin derivative, wherein the insulin derivative is selected from the group consisting of:
- N$^{\epsilon B29}$-ω-carboxy-pentadecanoyl-γ-L-glutamylamide desB30 human insulin,
- N$^{\epsilon B29}$-ω-carboxy-pentadecanoyl-γ-amino-butanoyl desB30 human insulin,
- N$^{\epsilon B29}$-ω-carboxy-tetradecanoyl-γ-L-glutamylamide desB30 human insulin,
- N$^{\epsilon B29}$-ω-carboxy-tridecanoyl-γ-L-glutamylamide desB30 human insulin,
- N$^{\epsilon B29}$-ω-carboxy-pentadecanoyl-β-alanyl desB30 human insulin,
- N$^{\epsilon B29}$-ω-carboxy-pentadecanoyl-β-L-aspartylamide desB30 human insulin,
- N$^{\epsilon B29}$-ω-carboxy-pentadecanoyl-ε-aminohexanoyl desB30 human insulin,
- N$^{\epsilon B29}$-ω-carboxy-pentadecanoyl-δ-aminopentanoyl desB30 human insulin,
- N$^{\epsilon B29}$-ω-carboxy-tridecanoyl-γ-amino-butanoyl desB30 human insulin,
- N$^{\epsilon B29}$-ω-carboxy-undecanoyl-γ-amino-butanoyl desB30 human insulin, and
- N$^{\epsilon B29}$-ω-carboxy-tetradecanoyl-γ-amino-butanoyl desB30 human insulin.

11. The insulin derivative according to claim 1, wherein Z is —CH(COOH)$_2$.

12. The insulin derivative according to claim 1, wherein Z is —N(CH$_2$COOH)$_2$.

13. The insulin derivative according to claim 1, wherein Z is —SO$_3$H.

14. The insulin derivative according to claim 1, wherein Z is —PO$_3$H$_2$.

* * * * *